US009211328B2

(12) United States Patent
Lanier et al.

(10) Patent No.: US 9,211,328 B2
(45) Date of Patent: *Dec. 15, 2015

(54) MODULATION OF NKG2D FOR PROLONGING SURVIVAL OF A HEMATOPOIETIC GRAFT

(71) Applicant: The Regents of the University of California, Oakland, CA (US)

(72) Inventors: Lewis L. Lanier, San Francisco, CA (US); Koetsu Ogasawara, Tokyo (JP); Jeffrey A. Bluestone, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/797,921

(22) Filed: Mar. 12, 2013

(65) Prior Publication Data

US 2014/0120082 A1 May 1, 2014

Related U.S. Application Data

(63) Continuation of application No. 13/177,480, filed on Jul. 6, 2011, now abandoned, which is a continuation of application No. 11/429,354, filed on May 5, 2006, now Pat. No. 7,998,481, which is a continuation-in-part of application No. PCT/US2005/011487, filed on Apr. 5, 2005.

(60) Provisional application No. 60/659,678, filed on Mar. 7, 2005, provisional application No. 60/576,242, filed on Jun. 1, 2004, provisional application No. 60/559,919, filed on Apr. 5, 2004.

(51) Int. Cl.
 A61K 39/40 (2006.01)
 A61K 35/28 (2015.01)
 A01N 25/00 (2006.01)
 A61K 39/395 (2006.01)
 C07K 16/28 (2006.01)
 A61K 39/00 (2006.01)

(52) U.S. Cl.
 CPC ....... *A61K 39/39541* (2013.01); *C07K 16/2851* (2013.01); *A61K 2039/505* (2013.01); *C07K 2316/96* (2013.01); *C07K 2317/73* (2013.01); *Y10S 514/885* (2013.01)

(58) Field of Classification Search
 None
 See application file for complete search history.

(56) References Cited

U.S. PATENT DOCUMENTS

| | | | |
|---|---|---|---|
| 6,262,244 B1 | 7/2001 | Houchins et al. | |
| 6,458,350 B1 | 10/2002 | Cosman et al. | |
| 6,541,610 B1 | 4/2003 | Smith | |
| 6,653,447 B1 | 11/2003 | Cosman et al. | |
| 6,821,522 B2 | 11/2004 | Raulet et al. | |
| 7,666,417 B2 | 2/2010 | Spies et al. | |
| 8,637,011 B2 | 1/2014 | Baron et al. | |
| 2002/0187151 A1 | 12/2002 | Raulet et al. | |
| 2003/0044410 A1 | 3/2003 | Skurkovich et al. | |
| 2003/0095965 A1 | 5/2003 | Van Beneden et al. | |
| 2003/0165835 A1 | 9/2003 | Spies et al. | |
| 2003/0171280 A1 | 9/2003 | Soderstrom | |
| 2004/0115198 A1 | 6/2004 | Spies et al. | |
| 2005/0158307 A1 | 7/2005 | Spies et al. | |
| 2005/0233391 A1 | 10/2005 | Spies et al. | |
| 2006/0280755 A1 | 12/2006 | Baron et al. | |
| 2007/0077241 A1 | 4/2007 | Spies et al. | |
| 2008/0260727 A1 | 10/2008 | Lanier et al. | |

FOREIGN PATENT DOCUMENTS

| | | |
|---|---|---|
| WO | 99/52877 A1 | 10/1999 |
| WO | 01/71005 A2 | 9/2001 |
| WO | 02/068615 A2 | 9/2002 |
| WO | 03/029436 A2 | 4/2003 |
| WO | 03/089616 A2 | 10/2003 |
| WO | 2004/087739 A2 | 10/2004 |
| WO | 2005/097160 A2 | 10/2005 |
| WO | 2005/097160 A3 | 3/2006 |

OTHER PUBLICATIONS

Kim et al ., J of Immunol, 2007, v.179, pp. 6416-6420.*
Rehermann, Barbara, "Intrahepatic T Cells in Hepatitis B: Viral Control versus Liver Cell Injury", The Journal of Experimental Medicine, vol. 191, No. 8, Apr. 17, 2000, pp. 1263-1268.
Roberts et al., "Cutting Edge: NKG2D Receptors Induced by IL-15 Costimulate CD28-Negative Effector CTL in the Tissue Microenvironment", J. Immunol., vol. 167, 2001, pp. 5527-5530.
Rollier et al., "Control of Heterologous Hepatitis C Virus Infection in Chimpanzees is Associated with the Quality of Vaccine-Induced Peripheral T-Helper Immune Response", Journal of Virology, vol. 78, Jan. 2004, pp. 187-196.
Saikali et al., "NKG2D-Mediated Cytotoxicity toward Oligodendrocytes Suggests a Mechanism for Tissue Injury in Multiple Sclerosis", Journal of neuroscience, vol. 27, No. 5, Jan. 31, 2007, pp. 1220-1228.
Schrambach et al., "In vivo Expression Pattern of MICA and MICB and its Relevance to Auto-Immunity and Cancer", PLoS One, vol. 2, 2007, p. e528.
Seiler et al., "Elevated mRNA Expression of the NK Cell Receptor NKG2D is Associated with Acute Rejection in Renal Transplantation", Immunobiology, vol. 210, No. 6-8, Sep. 15, 2005, p. 506.
Sherer et al., "Atherosclerosis", Annals of the Rheumatic Diseases, vol. 61, 2002, pp. 97-99.
Shirai et al., "An Epitope in Hepatitis C Virus Core Region Recognized by Cytotoxic T Cells in Mice and Humans", Journal of Virology, vol. 68, No. 5, May 1994, pp. 3334-3342.

(Continued)

*Primary Examiner* — Michail Belyavskyi
(74) *Attorney, Agent, or Firm* — Morrison & Foerster LLP

(57) ABSTRACT

The present invention relates to methods and compositions for treating and/or preventing autoimmune and/or inflammatory disease. In particular, the present invention provides therapeutics for impairing the expansion and function of autoreactive T cells, NK cells and/or NKT cells, by modulating NKG2D.

17 Claims, 34 Drawing Sheets

(56) References Cited

OTHER PUBLICATIONS

Snyder et al., "The Double Life of NK Receptors: Stimulation or Co-Stimulation?", Trends in Immunology, vol. 25, No. 1, Jan. 2004, pp. 25-32.

Sollid, Ludvig M., "Intraepithelial Lymphocytes in Celiac Disease: License to Kill Revealed", Immunity, vol. 21, 2004, pp. 303-304.

Steinle et al., "Interactions of Human NKG2D with its Ligands MICA, MICB, and Homologs of the Mouse RAE-1 Protein Family", Immunogenetics, vol. 53, Feb. 19, 2001, pp. 279-287.

Sutherland et al., "The UL16-Binding Proteins, A Novel Family of MHC Class I-Related Ligands for NKG2D, Activate Natural Killer Cell Functions", Immunol Rev, vol. 181, 2001, pp. 185-192.

Sutherland et al., "UL16-Binding Proteins, Novel MHC Class I-Related Proteins, Bind to NKG2D and Activate Multiple Signaling Pathways in Primary NK Cells", J Immunol, vol. 168, 2002, pp. 671-679.

Takeda et al., "Critical Contribution of Liver Natural Killer T Cells to a Murine Model of Hepatitis", Proc. Natl. Acad. Sci., vol. 97, 2000, pp. 5498-5503.

Tan et al., "Strategies for Hepatitis C Therapeutic Intervention: Now and Next", Current Opinion in Pharmacology, vol. 4, No. 5, Oct. 2004, pp. 465-470.

Tufveson et al., "New Immunosuppressants: Testing and Development in Animal Models and the Clinic: with Special Reference to DSG", Immunological Reviews, vol. 136, No. 1, 1993, pp. 99-109.

Verdaguer et al., "Spontaneous Autoimmune Diabetes in Monoclonal T Cell Nonobese Diabetic Mice", J Exp Med, vol. 186, 1997, pp. 1663-1676.

Wang et al., "Detection of Serum TNF-alpha,IFN-beta,IL-6 and IL-8 in Patients with Hepatitis B", World Journal of Gastroenterology, vol. 5, No. 1, Feb. 1999, pp. 38-40.

Warrington et al., "CD4+,CD28- T Cells in Rheumatoid Arthritis Patients Combine Features of the Innate and Adaptive Immune Systems", Arthritis Rheum, vol. 44, 2001, pp. 13-20.

Wu et al., "An Activating Immunoreceptor Complex Formed by NKG2D and DAP10", Science, vol. 285, 1999, p. 730.

Yen et al., "Major Histocompatibility Complex Class I-Recognizing Receptors are Disease Risk Genes in Rheumatoid Arthritis", J Exp Med, vol. 193, 2001, pp. 1159-1167.

Zhang et al., "The Inhibitory Effects of Synthetic Short Peptides, Mimicking MICA and Targeting at NKG2D Receptors, on Function of NK Cells", Peptides, vol. 26, 2005, pp. 405-412.

Verneris et al., "Role of NKG2D Signaling in the Cytotoxicity of Activated and Expanded CD8+T Cells", Blood, vol. 103, No. 8, Apr. 15, 2004, pp. 3065-3072.

Hue et al., "A Direct Role for NKG2D/MICA Interaction in Villous Atrophy During Celiac Disease", Immunity, vol. 21, 2004, pp. 367-377.

Ito et al., "Blockade of NKG2D Signaling Prevents the Development of Murine CD4+T Cell-Mediated Colitis", Am. J. Physiol Gastrointest Liver Physiol., vol. 294, 2008, pp. G199-G207.

Jamieson et al., "The Role of the NKG2D Immunoreceptor in Immune Cell Activation and Natural Killing", Immunity, vol. 17, 2002, pp. 19-29.

Jaruga et al., "Crucial Role of IL-4/STAT6 in T Cell-Mediated Hepatitis: Up-Regulating Eotaxins and IL-5 and Recruiting Leukocytes", The Journal of Immunology, vol. 171, 2003, pp. 3233-3244.

Jaruga et al., "IFN- γ/STAT1 Acts as a Proinflammatory Signal in T Cell-Mediated Hepatitis Via Induction of Multiple Chemokines and Adhesion Molecules: a Critical Role of IRF-1", American Journal of Physiology—Gastrointestinal and Liver Physiology, vol. 287, 2004, pp. G1044-G1052.

Jinushi et al., "Autocrine IL-15 is Required for MHC Class I-Related Chain A and B Expression on Monocyte-Derived Dendritic Cells in Response to Interferon A/B: Impairment of Interferon-Induced IL-15 Production in Hepatitis C Virus Infection", Hepatology, vol. 38, No. 4, Oct. 2003, p. 343A.

Jinushi et al., "Autocrine/Paracrine IL-15 that is Required for Type I IFN-Mediated Dendritic Cell Expression of MHC Class I-Related Chain A and B is Impaired in Hepatitis C Virus Infection", Immunol., vol. 171, 2003, pp. 5423-5429.

Jinushi et al., "Critical Role of MHC Class I-Related Chain A and B Expression on IFN-Alpha-Stimulated Dendritic Cells in NK Cell Activation: Impairment in Chronic Hepatitis C Virus Infection", J, Immunol., vol. 170, 2003, pp. 1249-1256.

Jinushi et al., "Expression and Role of MICA and MICB in Human Hepatocellular Carcinomas and their Regulation by Retinoic Acid", Int. J. Cancer, vol. 104, 2003, pp. 354-361.

Kakimi et al., "Natural Killer T Cell Activation Inhibits Hepatitis B Virus Replication In Vivo", J. Exp. Med., vol. 192, 2000, pp. 921-930.

Karacki et al., "MICA and Recovery from Hepatitis C Virus and Hepatitis B Virus Infections", Genes and Immunity, vol. 5, 2004, pp. 261-266.

Kiessling et al., "Evidence for a Similar or Common Mechanism for Natural Killer Cell Activity and Resistance to Hemopoietic Grafts", Eur J Immunol, vol. 7, 1977, pp. 655-663.

Kim et al., "The Activating Immunoreceptor NKG2D and its Ligands are Involved in Allograft Transplant Rejection", Journal of Immunology, vol. 179, 2007, pp. 6416-6420.

Koziel et al., "Hepatitis C Virus (HCV)—Specific Cytotoxic T Lymphocytes Recognize Epitopes in the Core and Envelope Proteins of HCV", Journal of Virology, vol. 67, No. 12, Dec. 1993, pp. 7522-7532.

Lagget et al., "Current Pharmacotherapy for the Treatment of Chronic Hepatitis B", Expert Opinion in Pharmacotherapy, vol. 4, No. 10, 2003, pp. 1821-1827.

Lanier, "NKG2D in immunity and autoimmunity", Oral presentation made at the Juan March Meeting in Madrid, Spain, Jan. 20, 2004.

Lanier et al., "On Guard—Activating NK Cell Receptors", Nat Immunol, vol. 2, 2001, pp. 23-27.

Lanier et al., "Turning on Natural Killer Cells", J Exp Med, vol. 191, 2000, pp. 1259-1262.

Lauer et al., "Hepatitis C Virus Infection", N Engl J Med, vol. 345, 2001, pp. 41-52.

Li et al., "Complex Structure of the Activating Immunoreceptor NKG2D and its MHC Class I-Like Ligand MICA ", Nature Immunology, vol. 2, No. 5, May 2001, pp. 443-451.

Li et al., "Innate Immunity in the Liver", Current Opinion in Gastroenterology, vol. 19, No. 6, Nov. 2003, pp. 565-571.

Lodoen et al., "NKG2D-Mediated Natural Killer Cell Protection against Cytomegalovirus is Impaired by Viral Gp40 Modulation of Retinoic Acid Early Inducible 1 Gene Molecules", Journal of Experimental Medicine, vol. 197, No. 10, May 19, 2003, pp. 1245-1253.

Lodoen et al., "The Cytomegalovirus m155 Gene Product Subverts Natural Killer Cell Antiviral Protection by Disruption of H60-NKG2D Interactions", J Exp Med, vol. 200, 2004, pp. 1075-1108.

Lotzova et al., "Prevention of Rejection of Allogeneic Bone Marrow Transplants by NK 1.1 Antiserum1", Transplantation, vol. 35, No. 5, May 1983, pp. 490-494.

Maasho et al., "NKG2D is a Costimulatory Receptor for Human Naive CD8+T Cells", The Journal of Immunology, vol. 174, 2005, pp. 4480-4484.

Maier et al., "Inhibition of Natural Killer Cells Results in Acceptance of Cardiac Allografts in CD28-/- Mice", Nat Med, vol. 7, 2001, pp. 557-562.

Malarkannan et al., "The Molecular and Functional Characterization of a Dominant Minor H Antigen, H60", J Immunol, vol. 161, 1998, 3501-3509.

McNerney et al., "Role of Natural Killer Cell Subsets in Cardiac Allograft Rejection", Am J Transplant, vol. 6, 2006, pp. 505-513.

Meresse et al., "Coordinated Induction by IL15 of a TCR-Independent NKG2D Signaling Pathway Converts CTL into Lymphokine-Activated Killer Cells in Celiac Disease", Immunity, vol. 21, 2004, pp. 357-366.

Mestas et al., "Of Mice and Not Men: Differences between Mouse and Human Immunology", J. of Immunology, vol. 172, 2004, pp. 2731-2738.

Moser et al., "CD94-NKG2A Receptors Regulate Antiviral CD8(+) T Cell Responses", Nat Immunol, vol. 3, 2002, pp. 189-195.

Murphy et al., "Acute Rejection of Murine Bone Marrow Allografts by Natural Killer Cells and T Cells. Differences in Kinetics and Target Antigens Recognized", J Exp Med, vol. 166, 1987, pp. 1499-1509.

(56) References Cited

OTHER PUBLICATIONS

Murphy et al., "Natural Killer Cells Activated with Interleukin 2 In Vitro can be Adoptively Transferred and Mediate Hematopoietic Histocompatibility-1 Antigen-Specific Bone Marrow Rejection In Vivo", EurJ Immunol, vol. 20, 1990, pp. 1729-1734.
Murphy et al., "Rejection of Bone Marrow Allografts by Mice with Severe Combined Immune Deficiency (SCID). Evidence that Natural Killer Cell Scan Mediate the Specificity of Marrow Graft Rejection", J Exp Med, vol. 165, 1987, pp. 1212-1217.
Nowbakht et al., "Ligands for Natural Killer Cell-Activating Receptors are Expressed Upon the Maturation of Normal Myelomonocytic Cells but at Low Levels in Acute Myeloid Leukemias", Blood, vol. 105, 2005, pp. 3615-3622.
O'Callaghan et al., "Molecular Competition for NKG2D: H60 and RAE1 Compete Unequally for NKG2D with Dominance of H60", Immunity, vol. 15, 2001, pp. 201-211.
Ogasawara et al., "NKG2D in NK and T Cell-Mediated Immunity", Journal of Clinical immunology, vol. 25, No. 6, 2005, pp. 534-540.
Ogasawara et al., "A Role for NKG2D in NK Cell-Mediated Rejection of Mouse Bone Marrow Grafts", Nat. Immunol., vol. 6, 2005, pp. 938-945.
Ogasawara et al., "Impairment of NK Cell Function by NKG2D Modulation in NOD Mice", Immunity, vol. 18, No. 1, Jan. 2003, pp. 41-51.
Ogasawara et al., "Inducible Costimulator Costimulates Cytotoxic Activity and IFN-Gamma Production in Activated Murine NK Cells", J Immunol, vol. 169, 2002, pp. 3676-3685.
Ogasawara et al., "NKG2D blockade prevents autoimmune diabetes in NOD mice", Immunity vol. 20, No. 6, Jun. 2004, pp. 757-767.
Papatriantafyllou, Maria, "Antiviral Immunity: IL-21 Comes with Age", Nature Reviews Immunology, vol. 11, Apr. 2011, 1 page.
Par et al., "Increased TGF Beta 1 Secretion via Down-Regulating NKG2D Killer Activator Receptor Expression Results in Impaired Natural Killer Cell Activity in Patients with Chronic HCV Hepatitis", Journal of Hepatology, vol. 44, Suppl. 2, Apr. 2006, pp. S164-S165.
Park et al., "MICA Polymorphism is Associated with Type I Diabetes in the Korean Population", Diabetes Care, vol. 24, 2001, pp. 33-38.
Publicover et al., "Hepatitis B Virus Infection: A Strong Case Against Ageism", Hepatology, vol. 54, No. 4, 2011, pp. 1477-1479.
Publicover et al., "IL-21 is Pivotal in Determining Age-Dependent Effectiveness of Immune Responses in a Mouse Model of Human Hepatitis B", The Journal of Clinical Investigation, vol. 121, No. 3, Mar. 2011, pp. 1154-1162.
Racanelli et al., "Presentation of HCV Antigens to Naive CD8+T Cells: Why the Where, When, What and How are Important for Virus Control and Infection Outcome", Clinical Immunology, vol. 124, Jul. 2007, pp. 5-12.
Radaeva et al., "Natural Killer Cells Ameliorate Liver Fibrosis by Killing Activated Stellate Cells in NKG2D-Dependent and Tumor Necrosis Factor-Related Apoptosis-Inducing Ligand-Dependent Manners", Gastroenterology, vol. 130, No. 2, Feb. 2006, pp. 435-452.
Raulet, DH., "Roles of the NKG2D Immunoreceptor and Its Ligands", Nature Reviews Immunology, vol. 3, 2003, pp. 781-790.
Ravetch et al., "Immune Inhibitory Receptors", Science, vol. 290, 2000, pp. 84-89.
International Search Report and Written Opinion received for PCT Application No. PCT/US2005/011487, mailed on Jan. 2, 2006, 13 pages.
International Search Report and Written Opinion received for PCT Application No. PCT/US2007/10945, mailed on Jan. 23, 2008, 6 pages.
International Preliminary Report on Patentability received for PCT Patent Application No. PCT/US2005/011487, issued on Oct. 11, 2006, 9 pages.
International Preliminary Report on Patentability received for PCT Patent Application No. PCT/US2007/010945, issued on Nov. 11, 2008, 4 pages.
Extended European Search Report received for European Patent Application No. 09008665.3, mailed on Oct. 7, 2010, 4 pages.
Extended European Search Report received for European Patent Application No. 07776799.4, mailed on Dec. 2, 2010, 7 pages.
Extended European Search Report received for European Patent Application No. 10183329.1, mailed on Jan. 28, 2011, 4 pages.
"Autoimmune Diseases Coordinating Committee", National Institute of Health, Autoimmune Diseases Research Plan, U.S. Department of Health and Human Services, Dec. 2002, 83 pages.
Allez et al., "CD4 NKG2D T Cells in Chron's Disease Mediate Inflammatory and Cytotoxic Responses Through MICA Interactions", Gastroenterology, vol. 132, 2007, pp. 2346-2358.
Armeau et al., "Natural Killer Cell-Mediated Lysis of Hepatoma Cells via Specific Induction of NKG2D Ligands by the Histone Deacetylase Inhibitor Sodium Valproate", Cancer Res., vol. 65, 2005, pp. 6321-6329.
Atkinson et al., "The NOD Mouse Model of Type I Diabetes: As Good as it Gets?", Nature Medicine, vol. 5, Jun. 1999, pp. 601-604.
Azimi et al., "Immunostimulation by induced expression of NKG2D and its MIC ligands in HTLV-1-associated neurologic disease", Immunogenetics, vol. 58, 2006, pp. 252-258.
Bakker et al., "DAP12-Deficient Mice Fail to Develop Autoimmunity due to Impaired Antigen Priming", Immunity, vol. 13, 2000, pp. 345-353.
Baron et al., "Activation of a Nonclassical NKT Cell Subset in a Transgenic Mouse Model of Hepatitis B Virus Infection", Immunity, vol. 16, 2002, pp. 583-594.
Bauer et al., "Activation of NK cells and T cells by NKG2D, a receptor for stress-inducible MICA," Science, vol. 285, 1999, pp. 727-729.
Berzofsky et al., "Progress on New Vaccine Strategies against Chronic Viral Infections", The Journal of Clinical Investigation, vol. 114, No. 4, Aug. 2004, pp. 450-462.
Carayannopoulos et al., "Cutting Edge: Murine UL16-Binding Protein-Like Transcript I : A Newly Described Transcript Encoding a High-Affinity Ligand for Murine NKG2D", J Immunol, vol. 169, 2002, pp. 4079-4083.
Carayannopoulos et al., "Ligands for Murine NKG2D Display Heterogeneous Binding Behavior", Eur J Immunol, vol. 32, 2002, pp. 597-605.
Cerwenka et al., "Ectopic expression of retinoic acid early inducible-1 gene (RAE-1) permits natural killer cell-mediated rejection of a MHC class I bearing tumor in vivo", Proc. Natl. Acad. Sci. USA, vol. 98, 2001, pp. 11521-11526.
Cerwenka et al., "Retinoic Acid Early Inducible Genes Define a Ligand Family for the Activating NKG2D Receptor in Mice", Immunity, vol. 12, 2000, pp. 721-727.
Chisari et al., "Hepatitis B Virus Irnmunopathogenesis", Annu Rev Immunol, vol. 13, 1995, pp. 29-60.
Chisari et al., "Structural and Pathological Effects of Synthesis of Hepatitis B Virus Large Envelope Polypeptide in Transgenic Mice", Proc Natl Acad Sci USA, vol. 84, 1987, pp. 6909-6913.
Cosman et al., "ULBPs, Novel MHC Class I-Related Molecules, Bind to CMV Glycoprotein UL16 and Stimulate NK Cytotoxicity Through the NKG2D Receptor", Immunity, vol. 14, 2001, pp. 123-133.
Dandekar et al., "Important Roles for Gamma Interferon and NKG2D in Gamma-Delta T-Cell-Induced Demyelination in T-Cell Receptor Beta-Deficient Mice Infected with a Coronavirus", J. Virol., vol. 79, 2005, pp. 9388-9396.
De Lalla et al., "Production of Profibrotic Cytokines by Invariant NKT Cells Characterizes Cirrhosis Progression in Chronic Viral Hepatitis", The Journal of Immunology, vol. 173, 2004, pp. 1417-1425.
Diefenbach et al., "Selective Associations with Signaling Proteins Determine Stimulatory Versus Costimulatory Activity of NKG2D", Nat Immunol, vol. 3, 2002, pp. 1142-1149.
Ehrlich et al., "Engagement of NKG2D by Cognate Ligand or Antibody Alone is Insufficient to Mediate Costimulation of Human and Mouse CD8+ T Cells", J, Immunol., vol. 174, 2005, pp. 1922-1931.
Feld et al., "Antiviral Therapy for Hepatitis B Virus Infections: New Targets and Technical Challenges", Journal of Clinical Virology, vol. 25, No. 3, Dec. 2002, pp. 267-283.
Ferrari et al., "Immunopathogenesis of Hepatitis B", B J Hepatol, vol. 39, 2003, pp. S36-S43.

(56) References Cited

OTHER PUBLICATIONS

Franks, Isobel, "Viral Hepatitis: Interleukin 21 has a Key Role in Age-Dependent Response to HBV", Nature Reviews Gastroenterology & Hepatology, Advance online publication on Mar. 29, 2011, 1 page.

Geissmann et al., "Intravascular Immune Surveillance by CXCR6+ NKT Cells Patrolling Liver Sinusoids", PLOS Biology, vol. 3, 2005, pp. 650-661.

Genbank Accession No. AF285448, retrieved from Internet on Sep. 26, 2007, <http://www .ncbi.nlm.nih.gov/entrez/viewer.fcgi?db=nuccore&qty= 1 &c start= 1 &list_uids . . . >, 1 page.

Genbank Accession No. AF470403, retrieved from Internet on Sep. 26, 2007, <http://www.ncbi.nlm.nih.gov/entrez/viewer.fcgi?db=nuccore&qty=l&c_start=l&list_uids . . . >, 1 page.

Genbank Accession No. AJ554302, retrieved from Internet on Sep. 26, 2007, <http://www .ncbi .n lm.nih.gov/entrezlviewer.fcgi?db=muccore&qty= 1 &c _start= 1 &list_uids . . . >, 2 pages.

Genbank Accession No. NM_007360, retrieved from Internet on Sep. 26, 2007, <http ://www.ncbi.nlm.nih.gov/entrez/viewer.fcgi?db=nuccore&qty= 1 &c _start= 1 &list_uids . . . >, 5 pages.

Genbank Accession No. NM 033078, retrieved from Internet on Sep. 26, 2007, <http://www.ncbi.nlm.nih.gov/entrez/viewer.fcgi?db=nucleotide&qty=l&c_start=l&list_ui . . . >, 4 pages.

Genbank Accession No. NM 133512, retrieved from Internet on Sep. 26, 2007, <http://www.ncbi.nlm.nih.gov/entrez/viewer.fcgi?db=nucleotide&qty= 1 &c _start= 1 &list_ui . . . >, 3 pages.

George et al., "Tolerance and Alloreactivity of the Ly49D Subset of Murine NK Cells", J Immunol, vol. 163, 1999, pp. 1859-1867.

Goronzy et al., "T-Cell Regulation in Rheumatoid Arthritis", Curr Opin Rheumatol, vol. 16, 2004, pp. 212-217.

Grainger et al., "High Titres of Serum Antiuclear Antibodies, Mostly Directed Against Nucleolar Antigens, are Associated with the Presence of Coronary Atherosclerosis", Annals of the Rheumatic Diseases, vol. 61, 2002, pp. 110-114.

Groh et al., "Broad Tumor-Associated Expression and Recognition by Tumor-Derived Gamma Delta T Cells of MICA and MICB", Proc Natl Acad Sci, vol. 96, 1999, 6879-6884.

Groh et al., "Cell Stress-Regulated Human Major Histocompatibility Complex Class I Gene Expressed in Gastrointestinal Epithelium", Proc Natl Acad Sci., vol. 93, 1996, pp. 12445-12450.

Groh et al., "Costimulation of CD8alphabeta T Cells by NKG2D via Engagement by MIC Induced on Virus-Infected Cells", Nat. Immunol., vol. 2, 2001, pp. 255-260.

Groh et al., "Recognition of Stress-Induced MHC Molecules by Intestinal Epithelial Gammadelta T Cells", Science, vol. 279, 1998, pp. 1737-1740.

Groh et al., "Stimulation of T Cell Autoreactivity by Anomalous Expression of NKG2D and its MIC Ligands in Rheumatoid Arthritis", Proc Natl Acad Sci., vol. 100, 2003, pp. 9452-9457.

Groh et al., "Tumour-Derived Soluble MIC Ligands Impair Expression of NKG2D and T-Cell Activation", Nature, vol. 419, 2002, pp. 734-738.

Guidotti et al., "High-Level Hepatitis B Virus Replication in Transgenic Mice", J Virology, vol. 69, 1995, pp. 6158-6169.

Hamerman et al., "Cutting Edge: Toll-Like Receptor Signaling in Macrophages Induces Ligands for the NKG2D Receptor", J. Immunol., vol. 172, 2004, pp. 2001-2005.

Houchins et al., "DNA Sequence Analysis of NKG2, a Family of Related cDNA Clones Encoding Type II Integral Membrane Proteins on Human Natural Killer Cells," J. Exp. Med., vol. 173, Apr. 1991, pp. 1017-1020.

Huang et al., "Recent Development of Therapeutics for Chronic HCV Infection", Antiviral Research, vol. 71, Sep. 2006, pp. 351-362.

\* cited by examiner

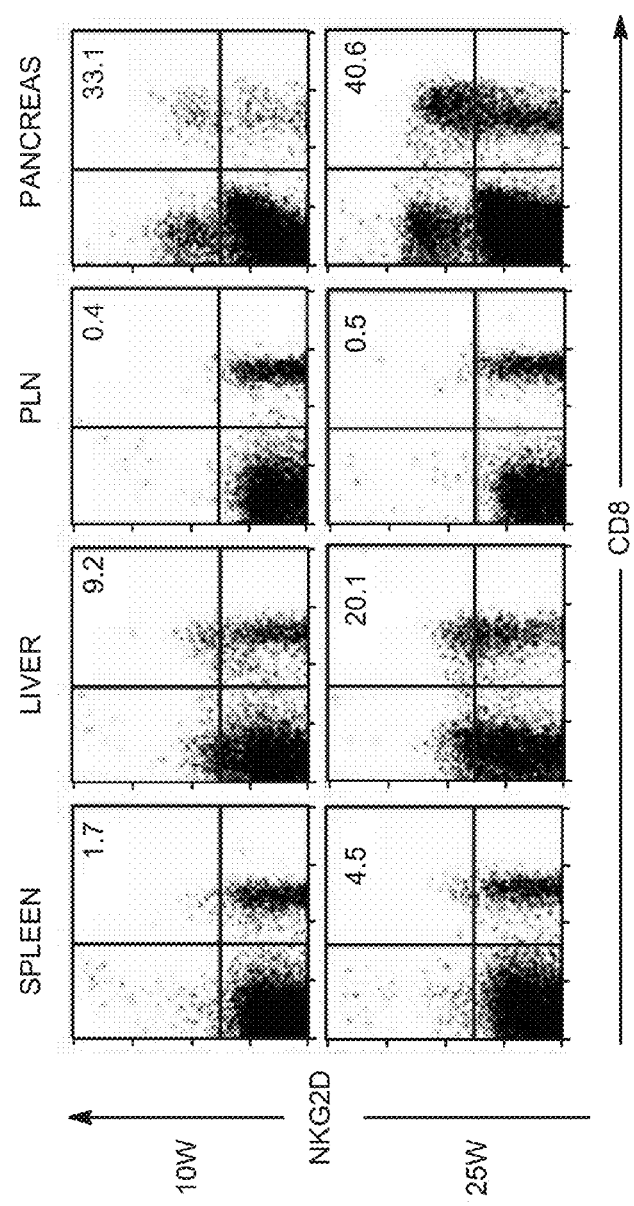

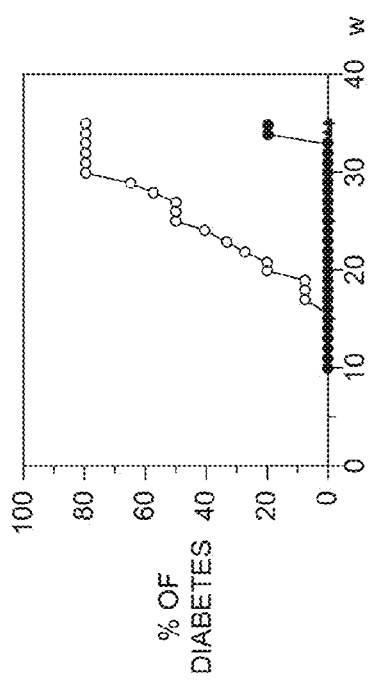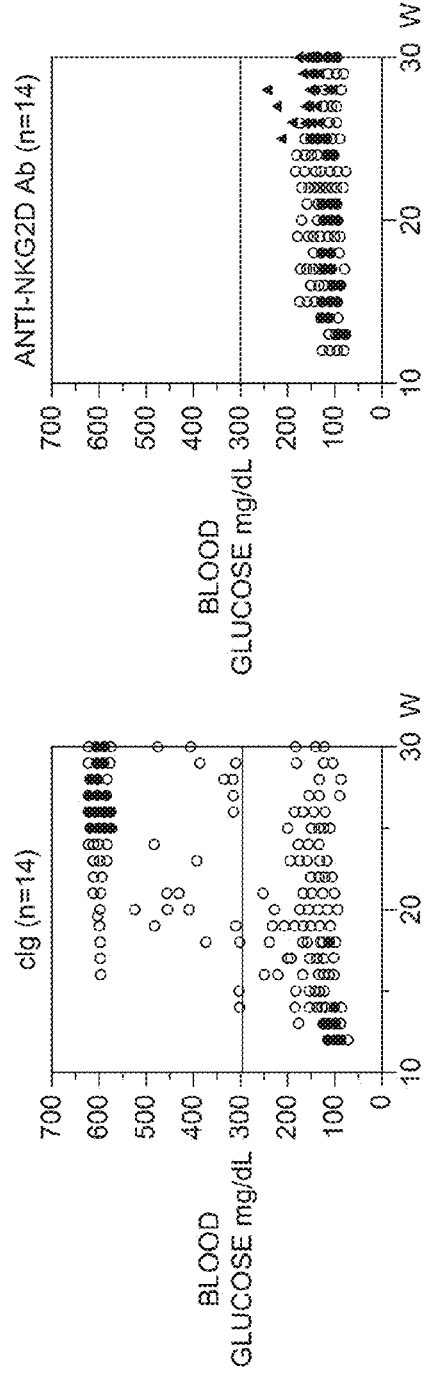
FIG. 3C
FIG. 3D

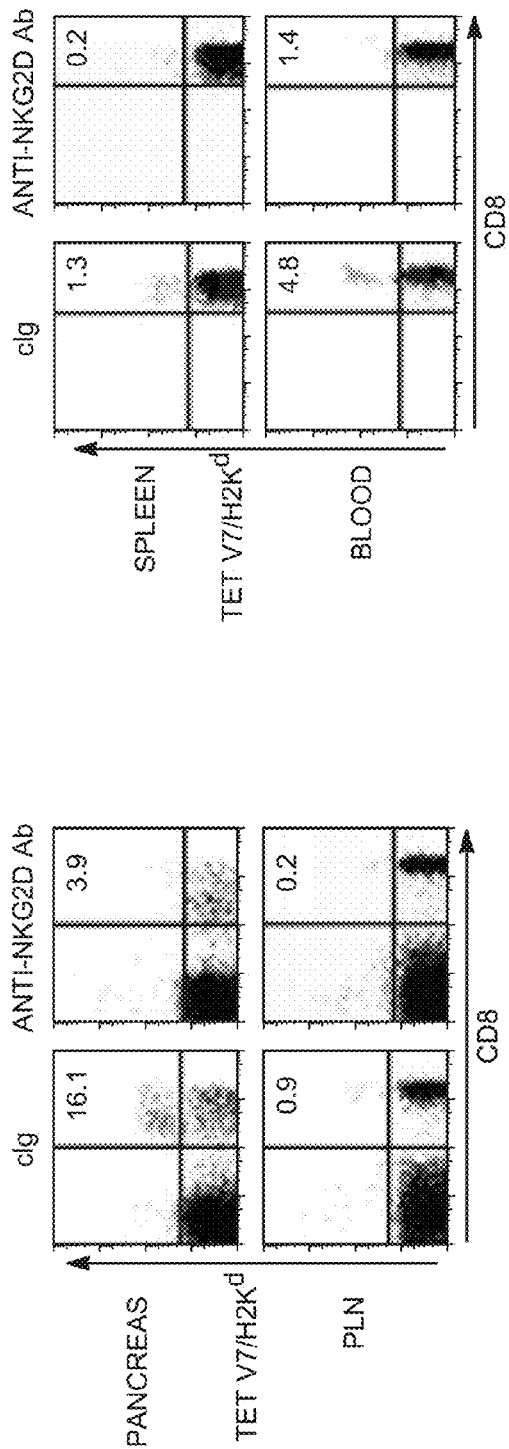
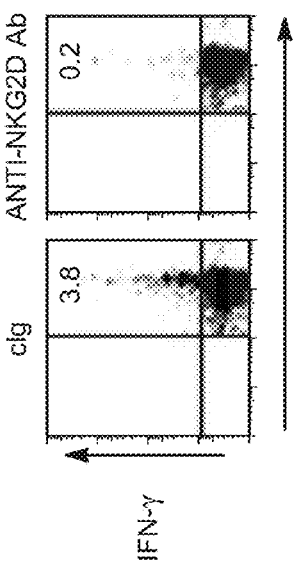
FIG. 4E
FIG. 4D
FIG. 4F

A
Murine NKG2D cDNA sequence
atggcattga ttcgtgatcg aaagtctcat cactcagaga tgagcaaatg ccataattac
gacctcaagc cagcaaagtg ggatacttct caagaacaac agaaacaaag attagcacta
actaccagtc aacctggaga aaatggtatc ataagaggaa gatacccctat agaaaaactc
aaaatatctc caatgttcgt tgttcgagtc cttgctatag ccttggcaat tcgattcacc
cttaacacat tgatgtggct tgccattttc aaagagacgt tcagccagt attgtgcaac
aaggaagtcc cagtttcctc aagagagggc tactgtggcc catgcctaa caactggata
tgtcacagaa caactgtta ccaattttt aatgaagaga aacctggaa ccagagccaa
gcttcctgtt tgtctcaaaa ttccagcctt ctgaagatat acagtaaaga gaacaggat
ttcttaaagc tggttaagtc ctatcactgg atgggactgg tccagatccc agcaaatggc
tcctggcagt gggaagatgg ctcctctctc tcatacaatc agttaactct ggtggaaata
ccaaaaggat cctgtgctgt ctatggctca agctttaagg cttacacaga agactgtgca
aatctaaaca cgtacatctg catgaaaagg gcggtgtaa B
Murine NKG2D amino acid sequence
MALIRDRKSH HSEMSKCHNY DLKPAKWDTS QEQQKQRLAL TTSQPGENGI IRGRYPIEKL
KISPMFVVRV LAIALAIRFT LNTLMWLAIF KETFQPVLCN KEVPVSSREG YCGPCPNNWI
CHRNNCYQFF NEEKTWNQSQ ASCLSQNSSL LKIYSKEEQD FLKLVKSYHW MGLVQIPANG
SWQWEDGSSL SYNQLTLVEI PKGSCAVYGS SFKAYTEDCA NLNTYICMKR AV C
Human NKG2D cDNA sequence
atggggtgga ttcgtggtcg gaggtctcga cacagctggg agatgagtga atttcataat
tataacttgg atctgaagaa gagtgatttt tcaacacgat ggcaaaagca aagatgtcca
gtagtcaaaa gcaaatgtag agaaaatgca tctccatttt ttttctgctg cttcatcgct
gtagccatgg gaatccgttt cattattatg gtagcaatat ggagtgctgt attcctaaac
tcattattca accaagaagt tcaaattccc ttgaccgaaa gttactgtgg cccatgtcct
aaaaactgga tatgttacaa aaataactgc taccaatttt ttgatgagag taaaaactgg
tatgagagcc aggcttcttg tatgtctcaa aatgccagcc ttctgaaagt atacagcaaa
gaggaccagg atttacttaa actggtgaag tcatatcatt ggatgggact agtacacatt
ccaacaaatg gatcttggca gtgggaagat ggctccattc tctcacccaa cctactaaca
ataattgaaa tgcagaaggg agactgtgca ctctatgcct cgagctttaa aggctatata
gaaaactgtt caactccaaa tacatacatc tgcatgcaaa ggactgtgta a D
Human NKG2D amino acid sequence
MGWIRGRRSR HSWEMSEFHN YNLDLKKSDF STRWQKQRCP VVKSKCRENA SPFFFCCFIA
VAMGIRFIIM VAIWSAVFLN SLFNQEVQIP LTESYCGPCP KNWICYKNNC YQFFDESKNW
YESQASCMSQ NASLLKVYSK EDQDLLKLVK SYHWMGLVHI PTNGSWQWED GSILSPNLLT
IIEMQKGDCA LYASSFKGYI ENCSTPNTYI CMQRTV

Figure 11

NKG2D Expression

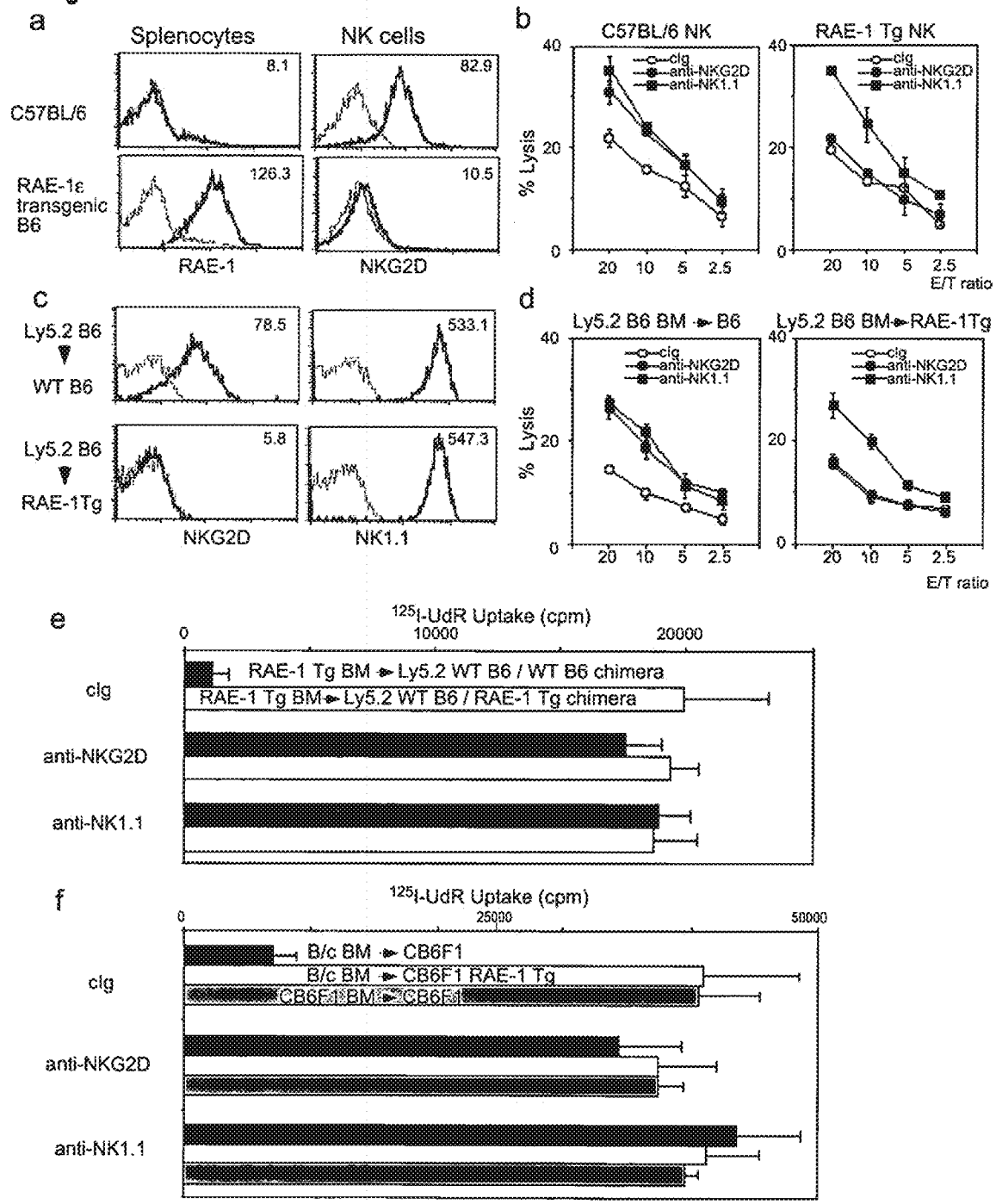

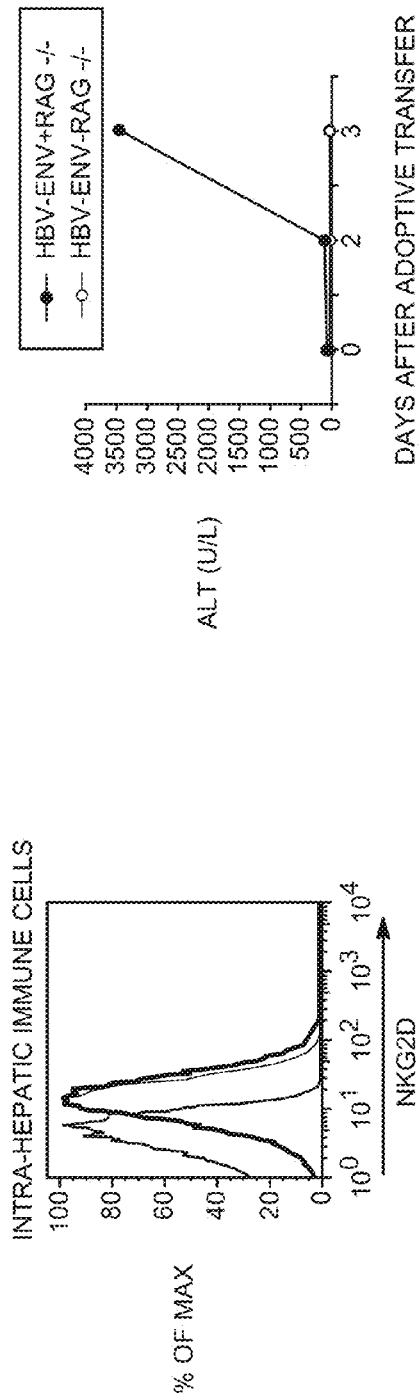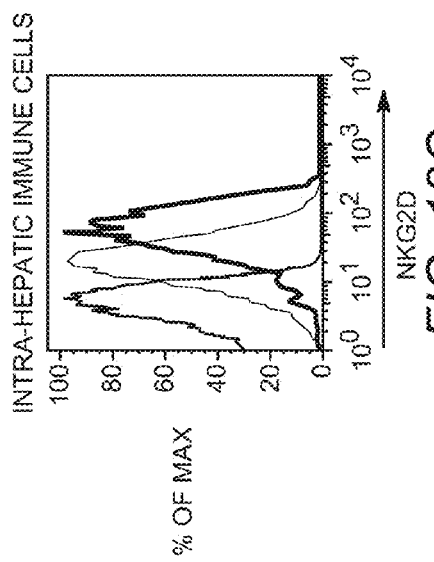
FIG. 18A
FIG. 18B
FIG. 18C

Figure 20 A
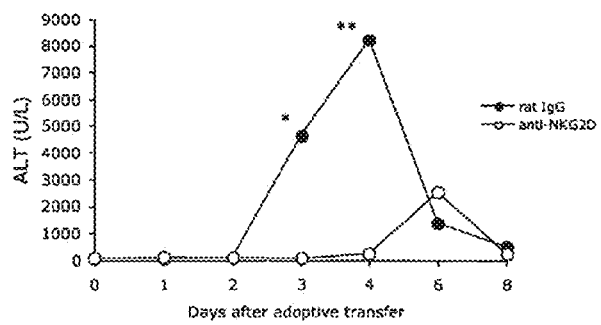
B
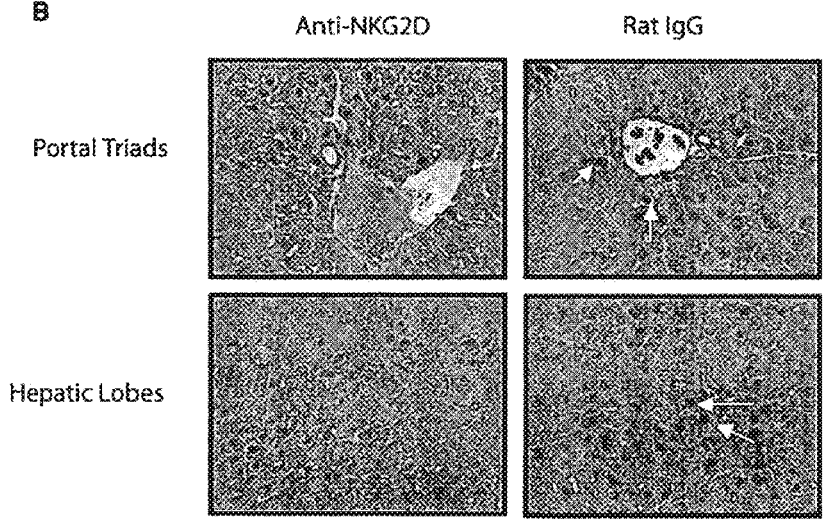
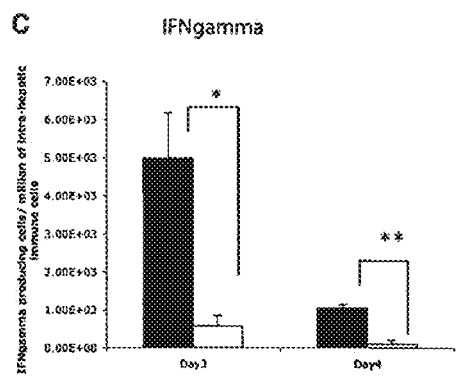
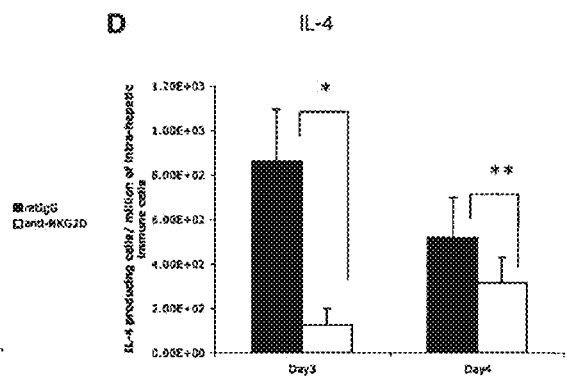

Figure 24
H&E stains
B. Balb → CD28-/- (CX5)
C. Balb → CD28-/- (no injection)
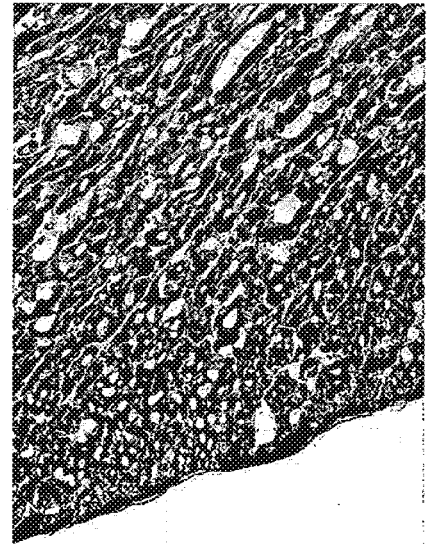
A. Balb/c heart (no transplant)

MODULATION OF NKG2D FOR PROLONGING SURVIVAL OF A HEMATOPOIETIC GRAFT

This application is a continuation of U.S. application Ser. No. 13/177,480, filed Jul. 6, 2011, now abandoned, which is a continuation of U.S. application Ser. No. 11/429,354, filed May 5, 2006, now U.S. Pat. No. 7,998,481, which is a continuation-in-part of International Application No. PCT/US2005/011487, filed Apr. 5, 2005, which claims the benefit of U.S. Provisional Applications 60/659,678, filed Mar. 7, 2005, 60/576,242, filed Jun. 1, 2004, and 60/559,919, filed Apr. 5, 2004, all herein incorporated by reference in their entirety.

This invention was made with government support under grants CA89189, CA95137, P30 DK26743, P60 DK63720, R37 AI066897, and K08 DK61970 awarded by the National Institutes of Health. The government has certain rights in the invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 643662000303SeqList.txt, date recorded: Dec. 18, 2013, size: 8 KB).

FIELD OF INVENTION

The present invention relates to methods and compositions for treating and/or preventing autoimmune and/or inflammatory disease. In particular, the present invention provides therapeutics for impairing the expansion and function of autoreactive T cells, NK cells and/or NKT cells, by modulating NKG2D.

BACKGROUND OF INVENTION

NKG2D is an activating receptor that is expressed in humans and mice on NK cells and certain types of T cells. NKG2D recognizes UL16 binding protein (ULBP1), ULBP2, ULBP3, ULBP4, and MHC class I chain-related molecules (MICA and MICB) in humans, and minor histocompatibility antigen 60 (H60), retinoic acid early inducible transcript (RAE-1), and murine ULBP-like transcript 1 (MULT-1) in mice. NKG2D homodimers associate with the adaptor molecule DAP10, which contains the consensus p85 phosphatidyl inositol-3-kinase (PI3-K) binding motif Tyr-Ile-Asn-Met (YINM, set forth as SEQ ID NO:9). NKG2D and DAP10 interact early in their biosynthetic pathway and this interaction is required for transport of NKG2D to the cell surface.

SUMMARY OF INVENTION

The present invention provides methods and compositions for treating or preventing a syndrome associated with NKG2D-mediated activation.

In one aspect, the methods are carried out by contacting leukocytes expressing NKG2D with an agent that reduces ligand-induced NKG2D activation of the cells under conditions suitable for treating or preventing the syndrome. In some embodiments, the contacting results in a reduction of at least about 30% in ligand-induced NKG2D activation; in other embodiments, the reduction is at least about 40%, 50%, 60%, 70%, 80%, or 90% relative to a control.

The agent may, without limitation, reduce the interaction of NKG2D with DAP10; reduce the amount of NKG2D on the surface of the cells; increase the rate at which surface NKG2D is internalized; reduce signaling through the NKG2D-NKG2D ligand complex; and/or reduce transcription or translation of NKG2D-encoding nucleic acids. In some embodiments, the agent enhances internalization of surface NKG2D polypeptides under conditions (such as, e.g., those present in chronic inflammatory syndromes) in which one or more of MICA, MICB, ULBP1, ULBP2, ULBP3, or ULBP4 cannot decrease the amount of cell-surface NKG2D to the extent that would be necessary (in the case of a therapeutic agent) to provide a therapeutic benefit.

In some embodiments, the agent used in the compositions and methods provided by the invention, comprises an antibody that binds NKG2D or an NKG2D-binding fragment thereof. The antibody may be a monoclonal antibody, such as, e.g., a human antibody, a humanized antibody, or a chimeric antibody.

In practicing the invention, the target leukocytes may be one or more of a NKG2D+CD8+ T cell, a NKG2D+CD4+ T cell, a NKG2D+γδ T cell; and a NKG2D+ NK cell; or the target cells may comprise macrophage cells.

In one aspect, methods of the invention can be used to treat and/or prevent an inflammatory syndrome associated with NKG2D-mediated activation in a mammal such as a human patient. The human patient may be diagnosed as having or being at substantial risk of developing such an inflammatory syndrome. In a particular aspect, the method of the invention is directed to the treatment of a diagnosed condition in a human patient.

In separate aspects, the invention also provides methods for treating or preventing rheumatoid arthritis, multiple sclerosis, celiac disease, inflammatory bowel diseases such as Crohn's disease and ulcerative colitis, psoriasis, or transplant rejection. Syndromes to which the present invention may also be applied include, without limitation, type I diabetes mellitus, systemic lupus erythematosus, Hashimoto's thyroiditis, myasthenia gravis, Guillain-Barré syndrome, autoimmune uveitis, primary biliary cirrhosis, autoimmune hepatitis, autoimmune hemolytic anemia, pernicious anemia, autoimmune thrombocytopenia, Grave's disease, autoimmune oophoritis, autoimmune orchitis, temporal arteritis, anti-phospholipid syndrome, Wegener's granulomatosis, Behcet's disease, scleroderma, polymyositis, dermatomyositis, ankylosing spondylitis, Sjogren's syndrome, dermatitis herpetiformis, pemphigus vulgaris, vitiligo, psoriatic arthritis, osteoarthritis, steroid-resistant asthma, chronic obstructive pulmonary disease, and atherosclerosis. In a particular aspect, the syndrome is not type I diabetes mellitus.

In another aspect, the present invention provides pharmaceutical formulations and kits that comprise an NKG2D modulator such as, for example, an anti-NKG2D antibody or antibody fragment. In one series of embodiments, the kits comprise an NKG2D modulator and instructions for contacting a leukocyte with a NKG2D modulator under conditions suitable for treating or preventing a syndrome associated with NKG2D-mediated activation of leukocytes.

The present invention also provides methods of identifying a NKG2D modulating agent, comprising: contacting a NKG2D+ leukocyte with a test agent; and measuring NKG2D expression by the leukocyte. In some preferred embodiments, measuring NKG2D expression comprises one or more of measuring NKG2D transcription, translation, and internalization. A subset of these embodiments, further comprise clinical testing the test agent according to FDA guidelines.

Moreover, the present invention provides methods of identifying a NKG2D modulating agent, comprising: contacting a NKG2D+ leukocyte with a test agent; and measuring ligand-induced NKG2D activation of the leukocyte. In some preferred embodiments, measuring ligand-induced NKG2D activation comprises one or more of measuring DAP10 phosphorylation, p85 PI3 kinase activity, Akt kinase activity, production of IFN-γ, and cytolysis of a NKG2D+ target cell. A subset of these embodiments further comprise clinical testing the test agent according to FDA guidelines.

In a further aspect, the invention provides a method of identifying a therapeutic or prophylactic agent for treatment or prevention of inflammatory conditions and/or autoimmune diseases associated with NKG2D activation. The method comprises screening potential agents (e.g., antibodies or antibody fragments) for the ability to specifically bind NKG2D and impair the expansion of NKG2D+ T cells or NK cells without significantly depleting such cells in a population of cells, suitable model, host or patient (e.g., by analyzing such antibodies using experimental strategies described herein). The screening may also or alternatively comprise screening for the ability to induce internalization of NKG2D on the surface of NKG2D+ T cells or NK cells.

In another particular aspect, the invention relates to the use of an agent (e.g., an antibody or antibody fragment) that is specific for NKG2D and is capable of impairing the expansion of NKG2D+ T cells or NK cells without depleting such cells for the preparation of a medicament for the treatment of rheumatoid arthritis.

In yet another particular aspect, the invention relates to the use of an agent (e.g., an antibody or antibody fragment) that is specific for NKG2D and is capable of impairing the expansion of NKG2D+ T cells or NK cells without depleting such cells for the preparation of a medicament for the treatment of multiple sclerosis.

In still another exemplary aspect, the invention relates to the use of an agent (e.g., an antibody or antibody fragment) that is specific for NKG2D and is capable of impairing the expansion of NKG2D+ T cells or NK cells without depleting such cells for the preparation of a medicament for the treatment of inflammatory bowel disease.

A further exemplary aspect of the invention relates to the use of an agent (e.g., an antibody or antibody fragment) that is specific for NKG2D and is capable of impairing the expansion of NKG2D+ T cells or NK cells without depleting such cells for the preparation of a medicament for the treatment of psoriasis.

An additional aspect of the invention is embodied in the use of an agent (e.g., an antibody or antibody fragment) that is specific for NKG2D and is capable of impairing the expansion of NKG2D+ T cells or NK cells without depleting such cells for the preparation of a medicament for the treatment of transplant rejection.

Moreover the present invention provides methods for treating or preventing viral hepatitis, the methods comprising administering an agent that reduces ligand-induced NKG2D activation of cells to a subject in need thereof under conditions suitable for treating or preventing viral hepatitis. In some embodiments, the subject is acutely infected with hepatitis B virus (HBV) or chronically infected with HBV. In further embodiments, the subject is acutely infected with hepatitis C virus (HCV) or chronically infected with HCV. In some embodiments, the subject has an elevated level of serum alanine aminotransferase (ALT). In some preferred embodiments, the conditions result in a reduction of hepatic necrosis. In some preferred embodiments, the conditions result in a reduction in levels of a cytokine in the subject's liver. In some particularly preferred embodiments, the cytokine comprises one or more of interferon-gamma, interleukin-4 and tumor necrosis factor alpha. In some embodiments, the conditions result in a reduction in lymphocytes infiltrating the subject's liver. The present invention also provides embodiments in which the cells are selected from the group consisting of NKG2D+CD8+ T cells, NKG2D+CD4+ T cells, NKG2D+γδ T cells, NKG2D+ NK cells, and macrophages. In some embodiments, the agent comprises an antibody that binds NKG2D or an NKG2D-binding fragment thereof. In some preferred embodiments, the antibody reduces the interaction of NKG2D with DAP10. In other preferred embodiments, the antibody reduces the amount of NKG2D on the surface of the cells. In some embodiments the reduction in the amount of cell-surface NKG2D occurs under conditions in which one or more of MICA, MICB, ULBP1, ULBP2, ULBP3, or ULBP4 cannot decrease the amount of cell-surface NKG2D. In some embodiments, the antibody increases the rate at which cell-surface NKG2D is internalized. In some embodiments the increase in the rate of NKG2D internalization occurs under conditions in which one or more of MICA, MICB, ULBP1, ULBP2, ULBP3, or ULBP4 cannot increase the rate of NKG2D internalization. In some particularly preferred embodiments, the antibody is a monoclonal antibody such as a human antibody, a humanized antibody, or a chimeric antibody. In some embodiments, the agent comprises a nucleic acid that reduces transcription or translation of NKG2D-encoding nucleic acids. In still further embodiments, the methods comprise administering an antiviral agent to the subject. In some embodiments, the antiviral agent is selected from the group consisting of lamivudine, adefovir dipivoxil, entecavir, interferon-alpha-2b and pegylated interferon-alpha-2a.

In addition the present invention provides methods for treating or preventing solid organ allograft rejection, the methods comprising administering an agent that reduces ligand-induced NKG2D activation of cells to a subject in need thereof, under conditions suitable for treating or preventing solid organ allograft rejection. In some embodiments, the graft is selected from the group consisting of a cardiac allograft, a lung allograft, a cardiac/lung allograft, a kidney allograft, a pancreas allograft, a kidney/pancreas allograft, a liver allograft, an intestine allograft and a skin allograft. In some embodiments, the administering is done prior to and after transplantation of the allograft. In some embodiments the cells are selected from the group consisting of NKG2D+CD8+ T cells, NKG2D+CD4+ T cells, NKG2D+γδ T cells, NKG2D+ NK cells, and macrophages. In some preferred embodiments, the agent comprises an antibody that binds NKG2D or an NKG2D-binding fragment thereof. In some embodiments, the antibody reduces the interaction of NKG2D with DAP10. In further embodiments, the antibody reduces the amount of NKG2D on the surface of the cells. In some embodiments, the reduction in the amount of cell-surface NKG2D occurs under conditions in which one or more of MICA, MICB, ULBP1, ULBP2, ULBP3, or ULBP4 cannot decrease the amount of cell-surface NKG2D. In further embodiments, the antibody increases the rate at which cell-surface NKG2D is internalized. In some embodiments, the increase in the rate of NKG2D internalization occurs under conditions in which one or more of MICA, MICB, ULBP1, ULBP2, ULBP3, or ULBP4 cannot increase the rate of NKG2D internalization. In some preferred embodiments, the antibody is a monoclonal antibody such as a human antibody, a humanized antibody, or a chimeric antibody. In some embodiments, the methods further comprise administering an adjunct therapy to the subject. In some preferred embodiments, the adjunct therapy comprises an immunomodulatory agent including but not limited to CTLA4Ig, cyclosporin A, tacrolimus, sirolimus, everolimus, basiliximab, daclizuman, mycophenolate mofetil, mycophenolate sodium, azathioprine and FTY-720. In some embodiments, the adjunct therapy comprises one or more of an antibiotic, an anti-fungal medication, an anti-ulcer medication and a diuretic.

BRIEF DESCRIPTION OF THE DRAWINGS

FIG. 1 is a graphic illustration of RAE-1 expression on pancreatic cells in pre-diabetic NOD mice.

FIG. 2(a) is a graphic illustration of NKG2D expression on $CD8^+$ T cells. Leukocytes from spleen, liver, pancreatic lymph nodes (PLN) and pancreas of 10-week and 25-week old NOD mice were isolated and stained by standard methods using monoclonal antibodies against CD8 and NKG2D. The indicated percentages of $NKG2D^+$ $CD8^+$ T cells (expressed as the percentage of total $CD8^+$ T cells) are shown.

FIG. 3(b) is a graphic illustration of the blood glucose levels measured weekly from 6 weeks to 40 weeks of age in the animals represented in FIG. 3a. FIG. 3(c) is a graphic illustration of the proportion of NOD mice that developed diabetes after treatment with anti-NKG2D mAb at a late pre-diabetic stage. NOD mice were treated with anti-NKG2D mAb (bi-weekly at 200 μg/mouse IP, dark circles; n=14) or control Ig (light circles; n=14) from 13 weeks to 25 weeks of age. At 25 weeks of age, seven anti-NKG2D mAb-treated mice continued to receive treatment until 30 weeks of age (dark triangles). FIG. 3(d) is a graphic illustration of blood glucose levels measured weekly from 12 weeks to 36 weeks of age in the animals represented in FIG. 3c.

FIG. 4(d) is a graphic illustration of the effect of anti-NKG2D antibody treatment on the accumulation of autoreactive NRP-V7/H-2K$^d$ tetramer-positive $CD8^+$ T cells in the pancreas. Leukocytes were isolated from pancreases and PLN of 18 week-old NOD mice treated with anti-NKG2D mAb (200 μg/mouse IP bi-weekly) or control Ig from 13 weeks of age. The indicated percentages of NRP-V7/H-2K$^d$ tetramer-positive $CD8^+$ T cells (gated on $CD8^+$ T cells) are shown. FIG. 4(e) is a graphic illustration of lymphocytes from spleen and peripheral blood in mice treated with control Ig or with anti-NKG2D (200 μg/mouse EP bi-weekly stained with NRP-V7/H-2K$^d$ tetramer and anti-CD8 mAb. The indicated percentages were NRP-V7/H-2K$^d$ tetramer-positive cells (gated on the $CD8^+$ T cell population). FIG. 4(f) is a graphic illustration of pancreatic lymph node cells isolated from 25 week-old NOD mice treated with control Ig (cIg) or anti-NKG2D (200 μg/mouse IP bi-weekly) beginning at 13 weeks of age, as indicated, and cultured with PMA (20 ng/ml) and ionomycin (500 ng/ml) and brefeldin A (5 μg/ml) for 6 hr. Intracellular IFN-γ was detected in CD8+ T cells by immunofluorescent staining and flow cytometry.

FIG. 5 is a graphic illustration of flow cytometric measurements from an adoptive transfer experiment of NOD T cells into NOD.scid recipients.

FIG. 8(a): Four days after transfer, blood samples were collected, stained with mAbs against mouse CD8 and NKG2D and analyzed by flow cytometry. The percentages of CD8$^+$ T cells labeled with CSFE are indicated. FIG. 8(b): On day 21 after adoptive transfer of CFSE-labeled OT-1 TcR-transgenic T cells and treatment with control Ig or anti-NKG2D mAb CX5 as indicated in (a), mice were sacrificed and splenocytes were isolated and analyzed by flow cytometry. FIG. 8(c): On day 7 after adoptive transfer of the CFSE-labeled CD8$^+$ NKG2D$^+$ OT-1 T cells, mice were injected with a depleting rat anti-mouse CD8 mAb (2.43 hybridoma, rat IgG2b isotype). Three days later peripheral blood cells were stained with control Ig, anti-CD8 or anti-NKG2D mAb and analyzed by flow cytometry. The purpose of this experiment was to demonstrate that the CX5 anti-NKG2D monoclonal antibody does not deplete NKG2D+ CD8+ T cells when the antibody is administered in vivo.

FIG. 10(a): NOD pancreas cells were isolated and stained with anti-CD45 mAb and with control Ig, an anti-pan RAE-1 mAb (clone 186107), anti-RAE-1γ mAb (clone CX1) or mouse NKG2D-Ig fusion protein (extracellular domain of mouse NKG2D fused to human IgG1 Fc), followed by appropriate second step reagents for visualization. Cells were analyzed by flow cytometry and CD45-negative and propidium iodide-negative, viable cells were evaluated. Cells stained with isotype-matched control Ig (cIg) demonstrated the specificity of mAb binding (thin line). FIG. 10(b): Pure anti-RAE-1 mAbs blocked the staining of biotin-labeled anti-RAE-1 mAbs, demonstrating the specificity of binding. Pancreas cells were pre-incubated with 0.25 µg purified cIg, anti-pan RAE-1 mAb clone 186107 or anti-RAE-1γ mAb clone CX1 (which also cross-reacts with RAE-1α and RAE-1β). After 20 min incubation on ice, these cells were then stained for an additional 20 min with 0.25 µg biotinylated control Ig, biotinylated anti-RAE-1 mAb clone 186107, biotinylated anti-RAE-1γ mAb clone CX1 and FITC-conjugated anti-CD45 mAb. To detect the biotinylated mAbs, cells were washed and incubated with PE-conjugated streptavidin. Cells were analyzed by flow cytometry and data shown were gated on CD45-negative, propidium iodide-negative, viable cells. Thus, NKG2D ligands are detected on the NOD pancreas cells using three independent reagents: anti-RAE-1 mAb clone 186107, anti-RAE-1 mAb clone CX1, and a mouse NKG2D-Ig fusion protein. Anti-RAE-1 mAb staining is specific in that biotinylated anti-RAE-1 mAb staining is completely blocked by purified anti-RAE-1 mAbs, but not a control rat IgG.

FIG. 11(a) shows the cDNA sequence (SEQ ID NO:1) of murine NKG2D. FIG. 11(b) shows the amino acid sequence (SEQ ID NO:2) of murine NKG2D. FIG. 11(c) shows the cDNA sequence (SEQ ID NO:3) of human NKG2D. FIG. 11(d) shows the amino acid sequence (SEQ ID NO:4) of human NKG2D.

FIG. 13(a): Freshly isolated BM cells were stained with a mouse NKG2D-human Ig Fc fusion protein (NKG2D Ig) or control human Ig (cIg). To detect the binding of NKG2D-Ig, a PE-conjugated anti-human IgG antibody (anti-human Ig PE) was used as a second step antibody. The dotted line represents cIg staining on BM cells. The thick line shows NKG2D ligand expression on BM cells. FIG. 13(b): BM cells were stained with biotinylated anti-pan RAE-1 mAb, biotinylated anti-H60 mAb, biotinylated anti-MULT1 mAb or a biotinylated isotype-matched cIg, and then were stained with PE-conjugated streptavidin. The dotted line shows the cIg staining and the thick line shows RAE-1, H60 and MULT1 expression on BM cells. FIGS. 13(c and d): CB6F1 recipients were treated with anti-NK1.1 mAb on day −2. On day 0, recipients were irradiated (11 Gy) and then reconstituted with B/c or CB6F1 BM cells (4×10⁶). On day 7, cells from the recipient spleens were isolated and analyzed as described for panels a and b. The dotted line represents cIg staining on BM cells. The thick line shows NKG2D ligand, RAE-1, H60 and MULT1 expression on BM cells. Numbers represent the mean fluorescence (arbitrary linear units) of the stained cells. FIGS. 13(e and f): graphically illustrates that phenotype of the RAE-1-expressing cells. BM cells were transferred into irradiated recipients pretreated with anti-NK1.1 mAb. Cells were isolated and stained as described for panel c. FIG. 13(g): illustrates that proliferating cells express RAE-1. B/c BM cells were transferred into irradiated CB6F1 mice that were pretreated with anti-NK1.1 mAb. Six days after transfer, BrdU (0.8 mg/mouse) was injected into mice. Two hr or 12 hr later, cells from recipient spleens were collected and stained with anti-pan-RAE-1 mAb and anti-BrdU. FIGS. 13(h and I): illustrates that RAE-1 is expressed on progeny of 5-FU-treated BM. BM cells from 5-fluorouracil-treated B/c mice were transferred into irradiated CB6F1 mice that were pretreated with anti-NK1.1 mAb. Eight days post-transfer, cells were isolated and analyzed as described for panels c and e. FIG. 13(i): shows c-kit and Sca-1 staining of RAE-1-positive gated cells. In panels e-i, >98% of cells stained with cIg were in the lower left quadrant (not shown). The percentage of cells in each of the top two quadrants is displayed. These results were reproducible in at least two independent experiments (representative data are shown).

FIG. 14(b): graphically illustrates the phenotype of B/c donor cells that repopulated irradiated CB6F1 recipients treated with anti-NKG2D mAb or control Ig. Mice were treated as described in panel a, with splenocytes harvested on day 8 post-transplantation, while cells were stained and data presented as described for FIG. 13.

FIG. 15(a) shows the expression of RAE-1ε on bone marrow cells in RAE-1ε transgenic B6 mice. Freshly isolated bone marrow from wild-type B6 and RAE-1ε transgenic B6 mice were stained with cIg or anti-pan-RAE-1 mAb. FIG. 15(b) illustrates that B6 NK cells kill syngeneic RAE-1ε transgenic BM cells in vitro. Freshly isolated BM from wild-type B6 and RAE-1ε transgenic B6 mice were used as targets in a standard in vitro cytotoxicity assay using IL-2-activated wild-type NK cells (B6 NK cells cultured for 7 days in 2000 U/ml recombinant human IL-2 from the National Cancer Institute Biological Resources Branch Preclinical Repository) as effectors, in the presence of cIg or anti-NKG2D mAb (clone 191004) used at 10 µg/ml. FIG. 15(c) illustrates that B6 mice reject syngeneic bone marrow expressing RAE-1ε. Approximately 4×10⁶ RAE-1ε transgenic B6 BM cells were transferred into irradiated B6 recipients. Recipient mice were injected with ¹²⁵IUdR on day 5, and spleens were harvested and counted on day 6. Black bars show ¹²⁵IUdR uptake of spleens in RAE-1ε transgenic BM→B6 mice and white bars show uptake of radiolabel in wild-type B6 BM→B6 recipients. Mice were treated with the non-depleting, neutralizing anti-NKG2D mAb or the NK cell-depleting anti-NK1.1 mAb (200 µg/mouse on day −2), as indicated. Results are shown as the mean±S.D. cpm (5 mice per group). The experiment was performed twice with comparable results. FIG. 15(d) illustrates that CB6F1 mice reject syngeneic bone marrow expressing RAE-1ε. Approximately 4×10⁶ RAE-1ε transgenic CB6F1 BM cells were transferred into irradiated CB6F1 recipients. Mice were injected with ¹²⁵IUdR on day 5, and spleens were harvested and counted on day 6. Black bars show ¹²⁵IUdR uptake of spleens in RAE-1ε transgenic CB6F1 BM→CB6F1 mice and white bars show uptake of radiolabel in wild-type CB6F1 BM→CB6F1 recipients. Mice were treated and data are shown as described in panel c.

FIG. 16(a) illustrates that DAP10−/− mice inefficiently reject syngeneic bone marrow expressing RAE-1ε. About 4×10$^6$ RAE-1ε transgenic B6 BM cells were transferred into irradiated recipients. Mice were injected with $^{125}$IUdR on day 5 and spleens were harvested and counted on day 6. Black bars show $^{125}$IUdR uptake of spleens in RAE-1ε transgenic B6 BM→wild-type B6 mice and white bars show uptake of radiolabel in RAE-1ε transgenic B6 BM→DAP10−/− B6 recipients. Mice were treated with the non-depleting, neutralizing anti-NKG2D mAb or the NK cell-depleting anti-NK1.1 mAb (200 μg/mouse on day −2), as indicated. Results are the mean±S.D. cpm (5 mice per group). FIG. 16(b) illustrates that DAP12−/− mice (Bakker et al., Immunity, 13:345-353, 2000) reject syngeneic bone marrow expressing RAE-1ε. About 4×10$^6$ RAE-1ε transgenic B6 BM cells were transferred into irradiated recipients. Mice were injected with $^{125}$IUdR on day 5 and spleens were harvested and counted on day 6. Black bars show $^{125}$IUdR uptake of spleens in RAE-1ε transgenic B6 BM→wild-type B6 mice and white bars show uptake of radiolabel in RAE-1ε transgenic B6 BM→DAP12−/− B6 recipients. Mice were treated and results are shown as described for panel a.

FIG. 17(a) illustrates the modulation of NKG2D on NK cells in RAE-1ε transgenic B6 mice. Splenocytes from wild-type and RAE-1ε transgenic B6 mice were stained with anti-pan-RAE-1 mAb (left panels) or anti-NKG2D and anti-NK1.1 mAb (right panels). RAE-1 expression was analyzed on spleen cells, and NKG2D expression was analyzed by gating on NK1.1$^+$ cells. Thin lines show cells stained with cIg, while thick lines show RAE-1 or NKG2D specific staining. Numbers represent the mean fluorescence (arbitrary linear units) of the stained cells. FIG. 17(b) graphically depicts that NKG2D-dependent cytotoxicity is impaired in RAE-1ε transgenic (Tg) NK cells. Enriched NK cells were prepared from the spleens of wild-type or RAE-1ε Tg B6 mice that were IP-injected with polyI:C (100 μg/mouse) one day before harvest. Monoclonal antibody-dependent re-direct killing assays against CD32-transfected 721.221 target cells were performed as described (Lanier et al., J Immunol, 141:3478-3485, 1998) by using control Ig (cIg), anti-NKG2D, or anti-NK1.1 mAbs. FIG. 17(c): illustrates the modulation of NKG2D on wild-type NK cells developing in RAE-1ε transgenic hosts. Ly 5.2 B6 BM cells (1×10$^7$/mouse) were transferred into irradiated wild-type (WT) or RAE-1ε Tg B6 mice. Three months after transplantation, the expression level of NKG2D (left panels) and NK1.1 (right panels) was analyzed on splenic NK cells (gated on CD3−, NK1.1+ lymphocytes). Thin lines show cells stained with cIg, while thick lines show RAE-1 or NKG2D specific staining. Numbers represent the mean fluorescence (arbitrary linear units) of the stained cells. FIG. 17(d) graphically depicts NKG2D-dependent cytotoxicity of NK cells in Ly5.2 B6 BM→RAE-1 Tg chimeric mice. Enriched NK cells were prepared from the spleens of Ly5.2 B6 BM→RAE-1 Tg and Ly5.2 B6 BM→B6 mice IP-injected with polyI:C (100 μg/mouse) one day before harvest. mAb-dependent re-directed cytotoxicity assays were performed as described in panel b. FIG. 17(e) illustrates that wild-type NK cells developing in RAE-1 Tg mice demonstrate impaired NKG2D-dependent bone marrow rejection. Black bars show $^{125}$IUdR uptake in spleens of RAE-1$^+$ Tg BM cells→chimeric mice (Ly5.2 B6 BM→wild-type B6), and white bars show uptake of radiolabel in spleens of RAE-1$^+$ Tg BM cells→chimeric mice (Ly5.2 B6 BM→RAE-1 Tg chimeric mice). FIG. 17(f) illustrates that hybrid resistance in RAE-1ε transgenic CB6F1 mice is impaired. About 4×10$^6$ B/c BM cells were transferred into irradiated recipients. Recipient mice were injected with $^{125}$IUdR on day 5 and spleens were harvested and counted on day 6. Black bars show $^{125}$IUdR uptake of spleens in B/c BM→wild-type CB6F1 mice, white bars show uptake of radiolabel in B/c BM→RAE-1ε transgenic CB6F1 recipients, and gray bars show CB6F1 BM→CB6F1 mice. Mice were treated with the non-depleting, neutralizing anti-NKG2D mAb or the NK cell-depleting anti-NK1.1 mAb (200 μg/mouse on day −2), as indicated. Results are shown as the mean±S.D. cpm (5 mice per group). The experiment was performed twice with comparable results.

FIG. 20 illustrates that NKG2D blockage prevents liver injury caused by the acute immune response to Hepatitis B Virus (HBV). Hepatic necrosis was assessed by the measurement of alanine aminotransferase (ALT) in the serum (FIG. 20A) of HBV-Env$^+$ Rag$^{-/-}$ mice treated with anti-NKG2D mAb (open circles) or rat IgG (closed circles). Student's t test analyses: *p<0.05 **p<0.01 Hematoxylin and eosin stained section (20×) of portal triads (FIG. 20B, upper pictures) and hepatic lobes (FIG. 20B, bottom pictures) from HBV-Env$^+$ Rag$^{-/-}$ mice treated with anti-NKG2D mAb (left pictures) or Rat IgG (right pictures), 4 days after the adoptive transfer. White arrows point to necrotic hepatocytes and the white asterisks indicate inflammatory infiltrate. Elispot analyses for IFN-gamma (FIG. 20C) and IL4 (FIG. 20D) producing intra-hepatic immune cells from HBV-Env$^+$ Rag$^{-/-}$ mice treated with Rat IgG (closed bar) or anti-NKG2D mAb (open bar), at days 3 and 4 after adoptive transfer. Student's t test analyses: *p<0.005 **p<0.02

FIG. 21A: Hepatic necrosis was assessed by the measurement of alanine aminotransferase (ALT) in the serum of HBV-Replication Rag$^{-/-}$ mice treated with anti-NKG2D mAb (open circles) or rat IgG (closed circles), 2, 3 and 4 days after adoptive transfer of syngeneic splenocytes. FIG. 21B: NKG2D surface expression in intra-hepatic NK1.1 positive cells from HBV-Replication Rag$^{-/-}$ mice (black line) as compared to Rag$^{-/-}$ mice (dashed line) at day 3 after the adoptive transfer of syngeneic, naïve splenocytes. Tinted histogram depicts staining using NKG2D isotype control (anti-rat IgG1). Results of elispot analyses of IFN-gamma (FIG. 21C) and IL4-producing intrahepatic immune cells (FIG. 21D) from HBV-Env+ Rag−/− mice treated with Rat IgG (closed bar) or anti-NKG2D mAb (open bar) are shown at day 3 after adoptive transfer. Student's t test analyses: *p<0.001.

FIG. 22A: Relative expression of pan-Rae in syngeneic and allogeneic full thickness tail skin grafts post-transplant is shown in wild type C57BL/6 mice. Expression of Rae-1 decreases to baseline levels in syngeneic grafts (C57BL/6→C57BL/6), whereas in allogeneic grafts (Balb/c→C57BL/6), Rae-1 expression is increased. FIG. 22B: Increase in pan-Rae expression mediated by T cells is depicted. Syngeneic and allogeneic transplants done in Rag−/− mice show no difference in relative expression of Rae-1. FIG. 22C: Expression of Rae-1 in syngeneic or allogeneic cardiac grafts at 7 days after transplant.

FIG. 24 illustrates that treatment in vivo with anti-NKG2D mAb (CX5) decreases leukocyte infiltration into allografts in CD28−/− mice. B6 CD28−/− mice were transplanted with Balb/c hearts. After 7 days, hearts from mice treated with CX5 demonstrate less leukocytic infiltration.

DETAILED DESCRIPTION OF THE INVENTION

Figure 1A:
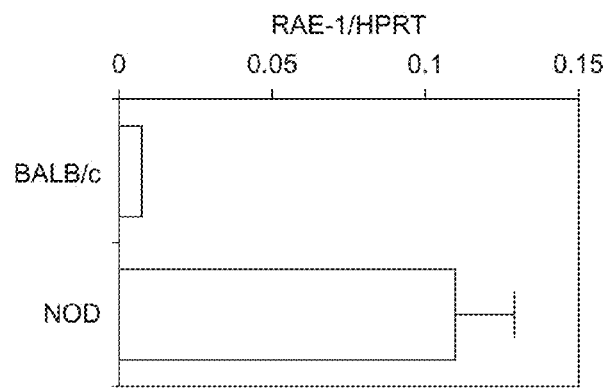
FIG. 1(a) shows RAE-1 mRNA measured by quantitative RT-PCR in pancreatic tissue from 12-16 week-old NOD and BALB/c mice.

The present invention is based, in part, on the surprising finding that modulation of NKG2D, an activating receptor on $CD8^+$ T cells, NK cells, and certain activated $CD4^+$ T cells, is an effective means for preventing and/or treating autoimmune and inflammatory syndromes. In one aspect, the present inventors have discovered agents and methods for stimulating internalization of NKG2D and have identified such agents as useful therapeutic modalities for treating syndromes associated with NKG2D activation. The agents and methods are particularly useful under conditions (such as those believed to be present, e.g., in chronic inflammatory syndromes) in which natural soluble NKG2D ligands are not able to stimulate internalization. The invention further encompasses any means for reducing the functional expression of NKG2D in order to treat such inflammatory syndromes. In some embodiments, the methods and compositions of the invention affect only the subset of leukocytes that depend for their activation primarily on NKG2D.

The invention encompasses methods and compositions effective for treating or preventing a syndrome associated with NKG2D-mediated activation of leukocytes. The methods are carried out by contacting leukocytes expressing NKG2D with an agent that reduces NKG2D-mediated activation of the cells under conditions suitable for preventing or treating the syndrome. The contacting may be carried out by any suitable method, including administering the agent or a composition comprising the agent to a patient, or host comprising cells activated by NKG2D pathway(s) under conditions allowing the delivery of the agent to the cells in the patient or host. NKG2D activation may be reduced according to the invention by one or more of: (i) depleting the cell surface of NKG2D molecules pre-existing on the cell surface; (ii) interfering with the functional interaction between NKG2D and DAP10 or otherwise blocking the signaling function of NKG2D; and (iii) preventing NKG2D molecules from reaching the cell surface, including interfering with the production of NKG2D at a transcriptional, translational, or post-translation level. In some embodiments, the invention encompasses reducing pre-existing cell surface NKG2D molecules by stimulating their internalization without concurrently causing significant activation that would trigger the effector functions of NKG2D-bearing leukocytes.

The terms "NKG2D," "NKG2-D," "D12S2489E," "KLRK1," and "killer cell lectin-like receptor subfamily K, member 1," as used herein refer to a human killer cell activating receptor gene, cDNA (e.g., *Homo sapiens*—GENBANK Accession No. NM_007360), and its gene product, as well as its mammalian counterparts, including wild type and mutant products. A human NKG2D coding region is set forth as SEQ ID NO:3, and a human NKG2D protein sequence is set forth as SEQ ID NO:4. Mammalian counterparts of NKG2D include but are not limited to mouse NKG2D (e.g., *Mus musculus*—GENBANK Accession No. NM_033078), rat NKG2D (e.g., *Rattus norvegicus*—GENBANK Accession No. NM_133512), pig NKG2D (e.g., *Sus scrofa*—GENBANK Accession No. AF285448), monkey NKG2D (e.g., *Macaca mulatta*—GENBANK Accession No. AJ554302), and orangutan NKG2D (e.g., *Pongo pygmaeus*—GENBANK Accession No. AF470403). Preferred embodiments of the present invention comprise NKG2D modulating agents such as NKG2D antagonists and partial antagonists.

Unless otherwise stated, the methods of the invention can be practiced in the context of treating (e.g., reducing the symptoms associated with and/or underlying conditions that are considered causative for a condition either in terms of time such symptoms/conditions exist, spread of such conditions/symptoms, severity of such conditions/symptoms, etc.) or preventing (e.g., reducing the likelihood of developing, delaying the onset of, delaying the severity of post-onset, reducing the severity of upon onset, etc.) any type of inflammatory condition associated with NKG2D activity, such as any inflammatory autoimmune disease associated with NKG2D activity. However, it will be recognized that such conditions can vary significantly such that methods for treating various conditions also may be considered unique aspects of the invention.

I. NKG2D-Modulating Agents

Unless otherwise stated or clearly implied by context, in practicing the invention, any agent that reduces NKG2D-mediated cell activation may be used. Non-limiting examples of such agents include: an NKG2D ligand, or an NKG2D-binding fragment, variant, or derivative thereof; an antibody, or a fragment, variant, or derivative thereof (such as, e.g., an NKG2D-binding antibody); a nucleic acid (or variant or derivative thereof), or a small molecule, that inhibits NKG2D or DAP10 production in a cell; peptides or small molecules that interfere with the formation or function of the NKG2D-DAP10 complex; small molecules that alter NKG2D signal transduction, and combinations of any of the foregoing. Exemplary NKG2D ligands can be found in, for instance, U.S. Pat. No. 6,653,447; Carayannopoulos et al., *J Immunol*, 169(8):4079-83, 2002; Carayannopoulos et al., *Eur J Immunol*, 32(3):597-605, 2002; Sutherland et al., *J Immunol*, 168(2):671-9, 2002; Sutherland et al., *Immunol Rev*, 181:185-92, 2001; and Cosman et al., *Immunity*, 14(2):123-33, 2001)

The invention encompasses agents that contact NKG2D-expressing cells from the exterior and reduce the activation of NKG2D-bearing cells when they are subsequently exposed to NKG2D-ligand bearing cells or recombinant NKG2D ligands. Any indicator of this activation may be monitored, including, without limitation, stimulation of DAP10 phosphorylation, stimulation of p85 PI3 kinase, activation of Akt, NKG2D-dependent production of interferon-gamma (IFN-γ) or other cytokines or chemokines, NKG2D-dependent killing of NKG2D-ligand bearing target cells, and the like. One means of assessing the level of NKG2D activation is by measuring the human NK cell killing of NKG2D ligand-bearing target cells (see, e.g., Example 1 below). In some embodiments of the invention, useful NKG2D-modulating agents are those that cause at least about 20% reduction of NKG2D ligand-induced NKG2D activation in a model system such as that described in Example 1; in other embodiments, the agent results in at least about 30%, 40%, 50%, 60%, 70%, 80%, 90%, or more reduction in ligand-induced NKG2D activation. For example, NKG2D ligand-induced activation can be reduced by at least about 30% in the presence of the agent as compared to a control. The control may be, for example, NKG2D-activation in the absence of the agent but under substantially identical conditions in either (a) an individual, (b) a population of substantially similar organisms, using an average value as control, or (c) both. Another means of assessing the level of NKG2D activation is by measuring IFN-γ production in the presence or absence of an NKG2D ligand such as MICA or ULBP. Any method for measuring IFN-γ production may be used, including, without limitation, immunoassays or other assays that measure IFN-γ protein; bioassays that measure IFN-γ activity, and the like. In some embodiments of the invention, useful NKG2D-modulating agents are those that cause at least about 20% reduction of NKG2D-mediated IFN-γ production; in other embodiments, the agent results in at least about 30%, 40%, 50%, 60%, 70%, 80%, 90%, or more reduction in NKG2D-mediated IFN-γ production.

In one series of embodiments, the NKG2D-modulating agents according to the invention stimulate cellular internalization of NKG2D. Internalization may be assessed by any appropriate means, such as, e.g., by flow cytometry (see, e.g., Example 2 below); immunofluorescence microscopy (including, monitoring internalization of an antibody by confocal microscopy); binding assays that detect cell-surface NKG2D, and the like. In some embodiments of the invention, useful NKG2D-modulating agents are those that cause at least about 10% reduction in the cell-surface level of NKG2D or a 10% increase in the rate of disappearance of NKG2D from the cell surface, as compared to control when tested in a model system such as that described in Example 2; in other embodiments, the agent results in at least about 20%, 30%, 40%, 50%, 60%, 70%, 80%, 90%, 95%, or >99% reduction in the cell-surface level or at least about 20%, 30%, 40%, 50%, 60%, 70%, 80%, 90%, 95% increase in the rate of disappearance of NKG2D.

Preferably, the NKG2D-modulating agents according to the invention do not result in significant cytolysis or depletion of NKG2D-expressing cells, including, e.g., one or more of CD8+ T cells, CD4+ T cells, γδ-TcR+ T cells, and CD56/16+ NK cells. The ability of an agent to kill NKG2D-expressing cells may be assessed using any appropriate means, such as, e.g., by detection of dead cells by flow cytometry or microscopy using annexin V or propidium iodide staining, incorporation of Trypan blue, europium assay or chromium release assay. In some embodiments of the invention, useful NKG2D-modulating agents are those that exhibit a detectable therapeutic benefit under conditions that preserve the viability at least about 90% of NKG2D-expressing cells. In other embodiments, the agent causes less than about 5%, 10%, 20%, 30%, 40%, 50%, 60%, 70%, or 80% reduction in the number of NKG2D-expressing cells.

The following table contains non-limiting examples of characteristics of NKG2D-modulating agents according to the invention.

TABLE 1

Characteristics of NKG2D-Modulating Agents

| Stimulation of NKG2D internalization (% reduction in NKG2D surface levels or % increase in rate of disappearance relative to control) | NKG2D activation (% reduction in activation of NKG2D-bearing cells after exposure to NKG2D-ligand bearing cells) | Depletion of NKG2D-expressing cells (% reduction in NKG2D-expressing cells relative to control) |
|---|---|---|
| 20% | 30% | <5% |
| 20 | 50 | <5 |
| 20 | 70 | <5 |
| 20 | 90 | <5 |
| 20 | 70 | 10 |
| 20 | 70 | 20 |
| 20 | 70 | 30 |
| 20 | 70 | 50 |
| 40 | 30 | <5 |
| 40 | 50 | <5 |
| 40 | 70 | <5 |
| 40 | 90 | <5 |
| 40 | 70 | 10 |
| 40 | 70 | 20 |
| 40 | 70 | 30 |
| 40 | 70 | 50 |
| 90 | 30 | <5 |
| 90 | 50 | <5 |
| 90 | 70 | <5 |
| 90 | 90 | <5 |
| 90 | 70 | 10 |
| 90 | 70 | 20 |
| 90 | 70 | 30 |
| 90 | 70 | 50 |

The present invention relates to the inability of natural soluble ligands of NKG2D (such as, e.g., MICA or ULBP) to stimulate internalization of NKG2D in patients suffering from chronic inflammation in a manner similar to internalization that might occur in individuals not suffering from chronic inflammation; without wishing to be bound by theory, it is believed that this phenomenon results at least in part from the high levels of cytokines that accompany chronic inflammatory states. (This phenomenon may be documented by comparing the NKG2D levels on T cells or NK cells in patients suffering from chronic inflammation and in healthy patients; similar NKG2D levels in the two groups, notwithstanding the fact that chronic inflammation is accompanied by high circulating levels of NKG2D ligands, reflect a defect in NKG2D internalization). The present invention encompasses agents that stimulate the internalization of NKG2D under conditions in which the natural soluble NKG2D ligands would not be effective or would be less effective in doing so, as well as the use of such agents in the various inventive methods provided herein. Any suitable model system for examining this effect may be used to demonstrate that particular agents possess or exhibit such characteristics, for instance by comparing the effect on NKG2D internalization of a natural soluble ligand and a modulating agent according to the invention, under conditions in which NKG2D-expressing cells are exposed to cytokines (including, without limitation, interleukin-2, interleukin-15, tumor necrosis factor, or combinations of the foregoing) under conditions known to counteract the effect of the natural soluble ligands on internalization. In some embodiments, the NKG2D-modulating agents of the invention can cause a reduction in surface NKG2D levels that is at least 10% greater than the reduction in surface NKG2D levels caused by a natural soluble NKG2D ligand, when internalization is measured under conditions (such as, e.g., in the presence of one or more cytokines) that interfere with the ability of the natural soluble ligand to mediate internalization. In other embodiments, the NKG2D-modulating agents are at least about 20%, 30%, 40%, 50%, 60%, 70%, 80%, 90%, 95%, or >99% more effective than a natural soluble NKG2D ligand in mediating NKG2D internalization.

A. NKG2D Ligands

One type of NKG2D-modulating agent according to the invention encompasses NKG2D ligands. Typically, such ligands exhibit some modification relative to the natural soluble NKG2D ligands (such as, e.g., soluble forms of MICA, MICB, and ULBP) that renders them effective in stimulating NKG2D internalization under conditions in which the natural soluble ligands are ineffective. For example, soluble forms of MICA and MICB proteins (i.e., lacking the transmembrane and cytoplasmic domains, see, e.g., U.S. Patent Application US2003/0165835, herein incorporated by reference), or fragments therefrom that retain NKG2D-binding activity, may be chemically cross-linked using conventional methods to form multimeric NKG2D ligands that are capable of binding to more than one NKG2D molecule and thereby stimulating internalization. NKG2D-binding activity may be assessed using any means, including, e.g., competitive binding, flow cytometry, and the like. In another series of embodiments, multimeric NKG2D ligands may be produced by expression of nucleic acids encoding polypeptides having tandem repeats (separated by appropriate spacers) of NKG2D-binding domains derived from MICA, MICB, or ULBP. In another series of embodiments, the ligands may incorporate additional chemical groups, such as, e.g., polyethylene glycol (PEG).

B. Antibodies

The present invention encompasses the use of any antibodies that can be used to decrease NKG2D-mediated activation, such as, e.g., those that stimulate internalization of NKG2D without significant activation via NKG2D-mediated signaling pathways. Non-limiting examples of such antibodies include antibodies directed against any suitable extracellular or intramembrane epitope of NKG2D; antibodies directed against any suitable extracellular or intramembrane epitope of DAP10; and antibodies directed against a soluble NKG2D ligand or an NKG2D-NKG2D ligand complex. Also encompassed are bispecific antibodies, i.e., antibodies in which each of the two binding domains recognizes a different binding epitope. The amino acid sequence of NKG2D is disclosed, e.g., in U.S. Pat. No. 6,262,244, the amino acid sequence of DAP10 is disclosed in Wu et al., Science 285:730, 1999, and the amino acid sequences of MICA and MICB polypeptides are disclosed, e.g., in U.S. Patent Application US 2003/0165835, all herein incorporated by reference in their entirety.

In general, the basic antibody structural unit is known to comprise a tetramer. Each tetramer includes two identical pairs of polypeptide chains, each pair having one "light" (about 25 kDa) and one "heavy" chain (about 50-70 kDa). The amino-terminal portion of each chain may include a variable region of about 100 to 110 or more amino acids primarily responsible for antigen recognition. The carboxy-terminal portion of each chain may define a constant region primarily responsible for effector function.

Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined with a "J" region of about 12 or more amino acids, with the heavy chain also including a "D" region of about 10 more amino acids. See generally, *Fundamental Immunology*, Ch. 7 (Paul, ed., 2nd ed. Raven Press, NY, 1989).

The variable regions of each light/heavy chain pair typically form the antibody-binding site. Thus, in general, an intact IgG antibody has two binding sites. Except in bifunctional or bispecific antibodies, the two binding sites are, in general, the same. Normally, the chains all exhibit the same general structure of relatively conserved framework regions (FR) joined by three hypervariable regions, also called complementarity determining regions or CDRs. The CDRs of the heavy and light chains of each pair are usually brought into alignment by the framework regions, enabling binding to a specific epitope. In general, from N-terminal to C-terminal, both light and heavy chains comprise the domains FR1, CDR1, FR2, CDR2, FR3, CDR3 and FR4. The assignment of amino acids to each domain is, generally, in accordance with the definitions of Sequences of Proteins of Immunological Interest, Kabat et al., National Institutes of Health, Bethesda, Md., 5th ed., NIH Publ. No. 91-3242, 1991; Kabat, *Adv Prot Chem*, 32:1-75, 1978; Kabat et al., *J Biol Chem*, 252:6609-6616, 1977; Chothia et al., *J Mol Biol*, 196:901-917, 1987; and Chothia et al., *Nature*, 342:878-883, 1989.

The antibodies of the present invention can encompass monoclonal antibodies, polyclonal antibodies, bispecific antibodies, Fab antibody fragments, F(ab)$_2$ antibody fragments, Fv antibody fragments (e.g., $V_H$ or $V_L$), single chain Fv antibody fragments and dsFv antibody fragments. Furthermore, the antibody molecules of the invention may be fully human antibodies, humanized antibodies, or chimeric antibodies. In some embodiments, the antibody molecules are monoclonal, fully human antibodies. Monoclonal antibodies encompass antibodies obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Monoclonal antibodies are advantageous in that they may be synthesized by a hybridoma culture, essentially uncontaminated by other immunoglobulins. The modifier "monoclonal" indicates the character of the antibody as being amongst a substantially homogeneous population of antibodies, and is not to be construed as requiring production of the antibody by any particular method.

The antibodies of the present invention include any antibody variable region, mature or unprocessed linked to any immunoglobulin constant region. If a light chain variable region is linked to a constant region, preferably it is a kappa chain. If a heavy chain variable region is linked to a constant region, preferably it is a human gamma 1, gamma 2, gamma 3 or gamma 4 constant region, more preferably, gamma 1, gamma 2 or gamma 4 and even more preferably gamma 1 or gamma 4.

In some embodiments, fully human monoclonal antibodies directed against, e.g., NKG2D or DAP10 are generated using transgenic mice carrying parts of the human immune system rather than the mouse system. These transgenic mice, which may be referred to, herein, as "HuMAb" mice, contain human immunoglobulin gene miniloci that encode unrearranged human heavy (mu and gamma) and kappa light chain immunoglobulin sequences, together with targeted mutations that inactivate the endogenous murine mu and kappa chain loci.

Accordingly, the mice exhibit reduced expression of mouse IgM or kappa, and in response to immunization, the introduced human heavy and light chain transgenes undergo class switching and somatic mutation to generate high affinity human IgG/kappa monoclonal antibodies. The generation of fully human antibodies in HuMAb mice is commonly known in the art.

Monoclonal antibodies may be made using the hybridoma method first described by Kohler et al., Nature, 256:495, 1975, or by other well-known, subsequently developed methods. In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

The culture medium in which hybridoma cells are grown is assayed for production of monoclonal antibodies directed against the antigen. The binding specificity of monoclonal antibodies produced by hybridoma cells may be determined by immunoprecipitation or by an in vitro binding assay, such as radioimmunoassay (RIA) or enzyme-linked immunoabsorbent assay (ELISA) or by immunofluorescence and flow cytometry or by western blot. After hybridoma cells are identified that produce antibodies of the desired specificity, affinity, and/or activity, the clones may be subcloned by limiting dilution procedures and grown by standard methods. Suitable culture media for this purpose include, for example, D-MEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding monoclonal antibodies or antibody fragments is readily isolated and sequenced using conventional procedures. The hybridoma cells serve as a source of such DNA. Once isolated, the DNA may be placed into expression vectors, which are then transfected into host cells such as E. coli cells, simian COS cells, human 293T cells, Chinese hamster ovary (CHO) cells, or myeloma cells that do not otherwise produce immunoglobulin protein, to obtain the synthesis of monoclonal antibodies in the recombinant host cells.

Antibodies or antibody fragments can also be isolated from antibody phage libraries generated using well-known techniques, with or without the use of chain shuffling as well as combinatorial infection and in vivo recombination as a strategy for constructing very large phage libraries. Thus, these techniques are viable alternatives to traditional monoclonal antibody hybridoma techniques for isolation of monoclonal antibodies.

Minor variations in the amino acid sequences of antibodies or immunoglobulin molecules are encompassed by the present invention, providing that the variations in the amino acid sequence maintain at least 75%, more preferably at least 80%, 90%, 95%, and most preferably 99% of the sequence. In particular, conservative amino acid replacements are contemplated. Conservative replacements are those that take place within a family of amino acids that are related in their side chains. Whether an amino acid change results in a functional peptide can readily be determined by assaying the specific activity of the polypeptide derivative. Fragments (or analogs) of antibodies or immunoglobulin molecules, can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Sequence motifs and structural conformations may be used to define structural and functional domains in accordance with the invention.

In some embodiments, amino acid substitutions are made that: (1) reduce susceptibility to proteolysis, (2) reduce susceptibility to oxidation, (3) alter binding affinity for forming protein complexes, (4) alter binding affinities, and/or (4) confer or modify other physicochemical or functional properties of such analogs.

In general, useful anti-NKG2D antibodies according to the present invention exhibit an affinity (Kd) for human NKG2D that is at least equal to that of soluble NKG2D ligands. In some embodiments, the antibodies bind human NKG2D with nanomolar affinity or, even more preferably, picomolar affinity. In some embodiments, the antibodies bind human NKG2D with a Kd of less than about 100 nM, 50 nM, 20 nM, 20 nM, or 1 nM.

In some embodiments, useful antibodies include those that reduce the interaction between human NKG2D and one or more of MICA, MICB, ULBP1, ULBP2, ULBP3, and ULBP4. Such blocking antibodies may be identified using conventional competition assays.

C. Nucleic Acid Modulators

The present invention encompasses modulation of NKG2D cell surface expression at a transcriptional, translational, or post-translational level. In some embodiments, the modulators are nucleic-acid based, including, without limitation, DNA, RNA, chimeric RNA/DNA, protein nucleic acid, and other nucleic acid derivatives.

In some embodiments, the NKG2D modulators encompass RNA molecules capable of inhibiting NKG2D production when introduced into an NKG2D-expressing cell (termed RNAi), including short hairpin double-stranded RNA (shRNA). Non-limiting examples of useful RNAi sequences for modulating NKG2D expression include those encoded by the sequences 5'-GGATGGGACT AGTACACATT CC-3' (SEQ ID NO:10); 5'-TGGCAGTGGG AAGATGGCTC C-3' (SEQ ID NO:11); and 5'-CAGAAGGGAG ACTGTGCACT CTATGCCTC-3' (SEQ ID NO:12). It will be understood that any sequence capable of reducing the cell surface expression of NKG2D may be used in practicing the present invention.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen heteroatom or a sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al., *Nucleic Acids Res,* 25:776-780, 1977; Wilson et al., *J Mol Recog,* 7:89-98, 1994; Chen et al., *Nucleic Acids Res,* 23:2661-2668, 1995; and Hirschbein et al., *Antisense Nucleic Acid Drug Dev,* 7:55-61, 1997). For example, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration).

The double-stranded structure may be formed from a single self-complementary RNA strand or from two complementary RNA strands. RNA duplex formation may be initiated either inside or outside the cell. The RNA may be introduced in an amount that allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are about 19-30 nucleotides in length, such as, e.g., about 21-23 nucleotides in length, corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

siRNA for use in the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen et al., *Proc Natl Acad Sci USA,* 98:9742-9747, 2001; and Elbashir et al., *EMBO J,* 20:6877-88, 2001). These double-stranded siRNA structures can then be directly introduced to cells, either by passive uptake or by a delivery system of choice. In certain embodiments, the siRNA constructs can be generated through the processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides.

siRNA molecules can be purified using conventional techniques. For example, gel electrophoresis can be used to purify siRNAs. Alternatively, non-denaturing methods, such as non-denaturing column chromatography, can be used to purify siRNA. In addition, chromatography (e.g., size exclusion chromatography), glycerol gradient centrifugation, affinity purification with antibody can be used to purify siRNAs.

In some embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA. PCT application WO01/77350 describes an exemplary vector for bi-directional transcription of a transgene to yield both sense and antisense RNA transcripts of the same transgene in a eukaryotic cell.

II. Methods of Treatment

The present invention provides methods for preventing and/or treating inflammatory diseases, including various inflammatory autoimmune disorders and syndromes associated with NKG2D activation. Such syndromes, include, but are not limited to, clinical situations in which induction of stress-related NKG2D ligands (e.g., MICA, MICB, and ULBPs) results in excessive activation and/or expansion of autoreactive T cells and/or NK cells, which may be reflected in increased levels of cytokines such as IL-2, TNF-α, and IL-15.

Accordingly, in a particular aspect, the invention provides a method for treating and/or preventing rheumatoid arthritis (RA). The method comprises delivering an effective amount of an agent that reduces ligand-induced NKG2D activation to a patient having RA or being identified/diagnosed as being at substantial risk of developing RA, such that RA is treated or prevented. In a particular aspect, the inventive RA treatment/prevention method is practiced by use of a monoclonal antibody or monoclonal antibody fragment "against" (i.e., that is "specific for" or that "specifically binds to" or that "preferentially binds to") NKG2D. In one aspect, the agent (e.g., an anti-NKG2D mAb or mAb fragment) is an agent that is demonstrated to be effective in ameliorating RA in an acceptable model of RA, such as is described in U.S. Pat. No. 6,414,218 and US Patent Publication No. 20030005469 (related principles and models are described in, e.g., Wooley, P. H., *Animal Models of Arthritis,* eds. J. H. Klippel and P. A. Dieppe, Mosby Publishers (London), 1998; Erring et al., *Arthritis Res,* 4 Suppl 3:S133-40, 2002; Holmdahl et al., *Ageing Res Rev,* 1(1):135-47, 2002; Anthony et al., *Clin Exp Rheumatol,* 17(2):240-4, 1999; Durie et al., *Clin Immunol Immunopathol,* 73(1):11-8, 1994; and Muller-Ladner et al., *Drugs Today (Barc),* 35(4-5):379-88, 1999). In a further aspect, the agent is an antibody that is capable of detectably reducing ligand-induced NKG2D activation of NKG2D-expression leukocytes and/or impairing expansion of NKG2D+ T cells or NK cells (e.g., impairing the expansion and/or function of autoreactive CD8+ T cells) (in contrast to, e.g., at least some of the antibodies described in US Patent Publication No. 20040115198), without significantly depleting such cells (e.g., causing a reduction of about 10% or less of such cells as compared to a suitable control). In one aspect, the method results in a modulation of one or more biomarkers in a manner consistent with the treatment or prevention (as applicable) of RA (e.g., serum IL-6, TNF R, IL-2R, shed CD4, shed CD8, and/or C reactive protein). In another aspect, the practice of the method results in a detectable reduction of synovial inflammation in the peripheral joints of the patient/host. In one aspect, the method results in preventing radiographic deterioration and improving physical function in the patient or host as exhibited by, e.g., a reduction in radiographic progression in the patient or host, reduction in swollen and tender joints (as determined by acceptable analytical criteria), and/or significantly improved quality of life (e.g., as determined by a reduction in disability scores on the RA Health Assessment Questionnaire).

In another particular exemplary aspect, the invention provides a method for treating and/or preventing multiple sclerosis (MS). The method comprises delivering an effective amount of an agent that reduces ligand-induced NKG2D activation to a human patient or mammalian host having MS or being identified/diagnosed as being at substantial risk of developing MS, such that MS is treated or prevented in the patient or host. In a particular aspect, the inventive MS treatment/prevention method is practiced by use of a monoclonal antibody or monoclonal antibody fragment against NKG2D (an "anti-NKG2D antibody"). In a more particular aspect, the agent is an anti-NKG2D monoclonal antibody that is capable of detectably reducing ligand-induced NKG2D activation of NKG2D-expression leukocytes and/or impairing expansion of NKG2D+ T cells or NK cells, without significantly depleting such cells.

In yet another exemplary aspect, the invention provides a method for treating and/or preventing inflammatory bowel disease (IBD), such as Crohn's disease or ulcerative colitis. The method comprises delivering an effective amount of an agent that reduces ligand-induced NKG2D activation to a human patient or mammalian host having IBD or being identified/diagnosed as being at substantial risk of developing IBD, such that IBD is treated or prevented in the patient or host. In a particular aspect, the inventive IBD treatment/prevention method is practiced by use of a monoclonal antibody or monoclonal antibody fragment against NKG2D. In a more particular aspect, the agent is an anti-NKG2D monoclonal antibody that is capable of detectably reducing ligand-induced NKG2D activation of NKG2D-expressing leukocytes and/or impairing expansion of NKG2D+ T cells or NK cells, without significantly depleting such cells.

In another facet, the invention provides a method for treating and/or preventing psoriasis. The method comprises delivering an effective amount of an agent that reduces ligand-induced NKG2D activation to a human patient or mammalian host having psoriasis or being identified/diagnosed as being at substantial risk of developing psoriasis, such that psoriasis is treated or prevented in the patient or host. Typically, the method is carried out by delivery of an effective amount of a monoclonal antibody or monoclonal antibody fragment against NKG2D to the patient. In a more particular aspect, the agent is an anti-NKG2D monoclonal antibody that is capable of detectably reducing ligand-induced NKG2D activation of NKG2D-expressing leukocytes and/or impairing expansion of NKG2D+ T cells or NK cells, without significantly depleting such cells.

In yet another facet, the invention provides methods of reducing the likelihood of transplant rejection (or reducing the severity or time to onset of a transplant rejection-related condition). The method comprises delivering (e.g., administering directly or administering by way of a composition comprising, a nucleic acid encoding, etc.) an effective amount of an agent that reduces ligand-induced NKG2D activation to a human patient or mammalian host that is about to be, is, or recently was the recipient of a tissue/organ transplant, such that the likelihood of rejection is detectably reduced (e.g., as compared to a control). In a particular aspect, the method is practiced by delivery of an anti-NKG2D mAb or anti-NKG2D mAb fragment. In a more particular aspect, the agent is an anti-NKG2D mAb or fragment that is capable of detectably reducing ligand-induced NKG2D activation of NKG2D-expression leukocytes and/or impairing expansion of NKG2D+ T cells or NK cells, without significantly depleting such cells.

In another aspect, an agent according to the invention, such as an anti-NKG2D mAb or anti-NKG2D mAb fragment, is delivered to a patient or host suffering from or at substantial risk of developing type I diabetes mellitus in an amount and under conditions sufficient to treat or prevent the condition in the patient or host.

The inventive method can similarly be applied to a variety of other autoimmune diseases and inflammatory conditions associated with NKG2D, including systemic lupus erythematosus, Hashimoto's thyroiditis, myasthenia gravis, Guillain-Barré syndrome, autoimmune uveitis, primary biliary cirrhosis, autoimmune hepatitis, autoimmune hemolytic anemia, pernicious anemia, autoimmune thrombocytopenia, Grave's disease, autoimmune oophoritis, autoimmune orchitis, temporal arteritis, anti-phospholipid syndrome, Wegener's granulomatosis, Behcet's disease, scleroderma, polymyositis, dermatomyositis, ankylosing spondylitis, Sjogren's syndrome, dermatitis herpetiformis, pemphigus vulgaris, vitiligo, psoriatic arthritis, osteoarthritis, steroid-resistant asthma, chronic obstructive pulmonary disease, and atherosclerosis. In some preferred embodiments, the transplant is a bone marrow (BM) or peripheral blood stem cell (PBSM) transplant. In some embodiments, the BMT or PBSCT transplant is administered as treatment of leukemia or lymphoma, while in other embodiments, the transplant is administered as treatment for other types of cancers such as neuroblastoma or multiple myeloma.

In practicing the present invention, an NKG2D modulator may be administered to a patient as a single dose comprising a single-dose-effective amount for preventing or treating an inflammatory or autoimmune syndrome, or in a staged series of doses, which together comprise an effective amount for preventing or treating the syndrome. An effective amount of an NKG2D modulator refers to the amount of the modulator which, when administered in a single dose or in the aggregate of multiple doses, or as part of any other type of defined treatment regimen, produces a measurable statistical improvement in outcome, as evidenced by at least one clinical parameter associated with the syndrome. An effective amount of an NKG2D modulator may slow the progression of a disease when compared with patients not receiving the NKG2D modulator.

It will be understood that the effective amount of the NKG2D modulator, as well as the overall dosage regimen, may vary according to the disease and the patient's clinical status, which, in turn, may be reflected in one or more clinical parameters such as clinically accepted disease scores. For example, for rheumatoid arthritis, the severity of disease and/or outcome of treatment, may be evaluated by monitoring number of swollen joints; pain; mobility; and/or the official disease score ACR 20/50 or 70. For Type 1 diabetes, severity of disease and/or outcome of treatment may be evaluated by measuring blood glucose levels or variations thereof, Hb1C levels, and the like. For multiple sclerosis, brain inflammation can be assessed through scanning the brain. For hematopoietic transplant rejection, severity of the disease (failure to engraft) and/or outcome of treatment may be evaluated by evidence of prolonged neutropenia, thrombocytopenia, and red-cell transfusion dependence in patients that have undergone myeloablative conditioning, and by failure to observe chimerism in patients that have undergone non-myeloablative conditioning. In general, detectable effects on treatment outcome using the methods and compositions of the present invention include a decrease in the necessity for other treatments (including, e.g., a decrease in the amount and/or duration of other drugs or treatments), a decrease in number and/or duration of hospital stays, a decrease in lost work days due to illness, and the like. It will be further understood that the effective amount may be determined by those of ordinary skill in the art by routine experimentation, by constructing a matrix of values and testing different points in the matrix.

The present invention encompasses combined administration of one or more additional agents in concert with an NKG2D modulator. It will be understood that, in embodiments comprising administration of combinations of an NKG2D modulator with other agents, the dosage of the NKG2D modulator may on its own comprise an effective amount and additional agent(s) may further augment the therapeutic benefit to the patient. Alternatively, the combination of the NKG2D modulator and the second agent may together comprise an effective amount for preventing or treating the syndrome. It will also be understood that effective amounts may be defined in the context of particular treatment regimens, including, e.g., timing and number of administrations, modes of administrations, formulations, etc.

In some embodiments in which the NKG2D-associated syndrome is Type 1 diabetes, the additional agent encompasses one or more of an agent that promotes the growth of pancreatic beta-cells or enhances beta-cell transplantation, such as, e.g., beta cell growth or survival factors or immunomodulatory antibodies. In some embodiments in which the NKG2D-associated syndrome is rheumatoid arthritis, the additional agent is one or more of methotrexate; an anti-TNF-α antibody; a TNF-α receptor-Ig fusion protein, an anti-IL-15 antibody, a non-steroidal anti-inflammatory drug (NSAID), and a disease-modifying anti-rheumatic drug (DMARD). For example, the additional agent may be a biological agent such as an anti-TNF agent (e.g., ENBREL®), infliximab (REMICADE®) and adalimumab (HUMIRA®) or rituximab (RITUXAN®). In some embodiments in which the NKG2D-associated syndrome is hematopoietic transplant rejection, hematopoietic growth factor(s) (e.g., erythropoietin, G-CSF, GM-CSF, IL-3, IL-11, thrombopoietin, etc.) or antimicrobial(s) (e.g., antibiotic, antiviral, antifungal) may be administered as an adjunct therapy. In some embodiments, where the NKG2D-associated syndrome is solid organ transplant (e.g., a heart transplant) rejection, the additional agent may be, e.g., CTLA4-Ig (abatacept; ORENCIA®). In some embodiments in which the NKG2D-associated syndrome is psoriasis, the additional agent is one or more of tar and derivatives thereof, phototherapy, corticosteroids, Cyclosporine A, vitamin D analogs, methotrexate, p38 mitogen-activated protein kinase (MAPK) inhibitors, as well as biologic agents such as anti-TNF-alpha agents and RITUXAN®. In some embodiments in which the NKG2D-associated syndrome is an inflammatory bowel disease (IBD) such as, for example, Crohn's Disease or ulcerative colitis, the additional agent is one or more of aminosalicylates, corticosteroids, immunomodulators, antibiotics, or biologic agents such as REMICADE® and HUMIRA®.

III. Pharmaceutical Formulations and Modes of Administration

The present invention encompasses pharmaceutical formulations comprising NKG2D modulators, which may also comprise one or more pharmaceutically acceptable carriers. Pharmaceutically acceptable carriers include any and all suitable solvents, dispersion media, coatings, antibacterial and antifungal agents, isotonic and absorption delaying agents, and the like that are physiologically compatible with an NKG2D modulator or related composition or combination provided by the invention. Examples of pharmaceutically acceptable carriers include one or more of water, saline, phosphate buffered saline, dextrose, glycerol, ethanol and the like, as well as combinations thereof. In many cases, it can be desirable to include isotonic agents, for example, sugars, polyalcohols such as mannitol or sorbitol, or sodium chloride in such a composition. Pharmaceutically acceptable substances also minor amounts of auxiliary substances such as wetting agents or emulsifying agents, preservatives or buffers, which desirably can enhance the shelf life or effectiveness of the NKG2D modulator, related composition, or combination. Suitability for carriers and other components of pharmaceutical compositions is determined based on the lack of significant negative impact on the desired biological properties of the NKG2D modulator, related composition, or combination.

NKG2D modulator compositions, related compositions, and combinations according to the invention may be in a variety of suitable forms. Such forms include, for example, liquid, semi-solid and solid dosage forms, such as liquid solutions (e.g., injectable and infusible solutions), dispersions or suspensions, emulsions, microemulsions, tablets, pills, powders, liposomes, dendrimers and other nanoparticles (see, e.g., Baek et al., *Methods Enzymol,* 362:240-9, 2003; and Nigavekar et al., *Pharm Res,* 21:476-83, 2004), microparticles, and suppositories. The optimal form depends on the intended mode of administration, the nature of the composition or combination, and the therapeutic application. Formulations also can include, for example, powders, pastes, ointments, jellies, waxes, oils, lipids, lipid (cationic or anionic) containing vesicles, DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also, e.g., Powell et al. "Compendium of excipients for parenteral formulations" *PDA J Pharm Sci Technol,* 52:238-311, 1998, and the citations therein for additional information related to excipients and carriers well known to pharmaceutical chemists.

NKG2D modulator compositions also include compositions comprising any suitable combination of a NKG2D modulator peptide and a suitable salt thereof. Any suitable salt, such as an alkaline earth metal salt in any suitable form (e.g., a buffer salt), can be used in the stabilization of NKG2D modulators (preferably the amount of salt is such that oxidation and/or precipitation of the NKG2D modulator is avoided). Suitable salts typically include sodium chloride, sodium succinate, sodium sulfate, potassium chloride, magnesium chloride, magnesium sulfate, and calcium chloride. Compositions comprising a base and NKG2D modulators also are provided. In other aspects, the invention provides a NKG2D modulator composition that lacks a tonicifying amount of any salt.

A composition for pharmaceutical use also can include diluents, fillers, salts, buffers, detergents (e.g., a nonionic detergent, such as Tween-80), stabilizers (e.g., sugars or protein-free amino acids), preservatives, tissue fixatives, solubilizers, and/or other materials suitable for inclusion in a pharmaceutically composition. Examples of suitable components also are described in, e.g., Berge et al., *J Pharm Sci,* 6661:1-19, 1977; Wang and Hanson, *J Parenteral Sci Tech,* 42:S4-S6, 1988, U.S. Pat. Nos. 6,165,779 and 6,225, 289; and other documents cited herein. Such a pharmaceutical composition also can include preservatives, antioxidants, or other additives known to those of skill in the art. Additional pharmaceutically acceptable carriers are known in the art and described in, e.g., Urquhart et al., *Lancet,* 16:367, 1980; Lieberman et al., PHARMACEUTICAL DOSAGE FORMS-DISPERSE SYSTEMS, 2nd ed., vol. 3, 1998; Ansel et al., PHARMACEUTICAL DOSAGE FORMS & DRUG DELIVERY SYSTEMS, 7th ed., 2000; Martindale, THE EXTRA PHARMACOPEIA, 31st ed.; Remington's PHARMACEUTICAL SCIENCES, 16th-20th editions; THE PHARMACOLOGICAL BASIS OF THERAPEUTICS, Goodman and Gilman, eds., 9th ed., 1996; Wilson and Gisvolds' TEXTBOOK OF ORGANIC MEDICINAL AND PHARMACEUTICAL CHEMISTRY, Delgado and Remers, eds., 10th ed., 1998; and U.S. Pat. Nos. 5,708,025 and 5,994,106. Principles of formulating pharmaceutically acceptable compositions also are described in, e.g., Platt, *Clin Lab Med,* 7:289-99, 1987; Aulton, PHARMACEUTICS: THE SCIENCE OF DOSAGE FORM DESIGN, Churchill Livingstone, N.Y., 1988; EXTEMPORANEOUS ORAL LIQUID DOSAGE PREPARATIONS, CSHP, 1998, and "Drug Dosage," *J Kans Med Soc,* 70(I):30-32, 1969. Additional pharmaceutically acceptable carriers particularly suitable for administration of vectors are described in, for example, International Patent Application WO 98/32859. In one exemplary aspect, the active compound or combination is prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., SUSTAINED AND CONTROLLED RELEASE DRUG DELIVERY SYSTEMS, J. R. Robinson, ed., Marcel Dekker, Inc., NY, 1978.

In another aspect, compositions of the invention intended for oral administration, for example, may be formulated with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Another aspect of the present invention provides a kit comprising a NKG2D modulator, related composition, or combination, pharmaceutically carrier, and optionally other pharmaceutical composition components. A kit may include, in addition to the NKG2D modulator, diagnostic or therapeutic agents. A kit may also include instructions for use in a diagnostic or therapeutic method. In one series of embodiments, the kit includes a NKG2D modulator, related compound, or combination composition in a highly stable form (such as in a lyophilized form) in combination with pharmaceutically acceptable carrier(s) that can be mixed with the highly stable composition to form an injectable composition.

NKG2D modulator compositions, related compositions, and combination compositions can be administered via any suitable route, such as an oral, mucosal, buccal, intranasal, inhalable, intravenous, subcutaneous, intramuscular, parenteral, intertumor, intratumor, or topical route. They may also be administered continuously via a minipump or other suitable device. The antibody or other NKG2D modulator generally will be administered for as long as the disease condition is present, provided that the antibody causes the condition to stop worsening or to improve. The antibody or other NKG2D modulator will generally be administered as part of a pharmaceutically acceptable composition as described elsewhere herein. The antibody may be administered by any suitable route, but typically is administered parenterally in dosage unit formulations containing conventional pharmaceutically acceptable carriers, adjuvants, and the like (stabilizers, disintegrating agents, anti-oxidants, etc.). The term "parenteral" as used herein includes, subcutaneous, intravenous, intraarterial, intramuscular, intrasternal, intratendinous, intraspinal, intracranial, intrathoracic, infusion techniques and intraperitoneal delivery. Most commonly, an antibody will be administered intravenously or subcutaneously. Routes of injection also include injection into the muscle (intramuscular, IM); injection under the skin (subcutaneous, SC); injection into a vein (intravenous, IV); injection into the abdominal cavity (intraperitoneal, IP); and other delivery into/through the skin (intradermal, ID, usually by multiple injections).

The invention further provides method of promoting the sale and/or use of a compound according to any of the preceding aspects, or otherwise described herein, comprising distributing information (e.g., by printed materials that are handed out, mailed, etc.; by advertising signage; by television programs and advertisements; by radio programs and advertisements; by interne site postings; by email; by telemarketing; by door-to-door or person-to-person marketing; by funding and/or hosting conferences, panels, forums, etc. by employing and/or contracting for the services of salespeople and/or medical/scientific liaisons, by funding and/or hosting scientific research and publications related to such uses, etc.) related to the use of the compound in the prevention or treatment of any condition or combination of conditions recited in any of the foregoing aspects or described elsewhere herein to any persons or entities of potential interest (e.g., pharmaceutical chains, formulary managers, insurance companies, HMOs, hospitals and hospital chains, other health care companies, pharmacy benefit managers, potential patients, patients in remission, primary care physicians, nurses, doctors of pharmacy, and/or key opinion leaders).

The following examples are provided in order to demonstrate and further illustrate certain preferred embodiments and aspects of the present invention and are not to be construed as limiting the scope thereof.

EXAMPLE 1

Assay for NKG2D Activation

IL-2 activated human NK cells are co-cultured with an appropriate $^{51}$Cr-labeled target cell culture, such as mouse Ba/F3 cells that have been transfected with cDNA encoding human MICA under conditions in which the MICA polypeptide is expressed; and, as control cells, the same target cells that have not been transfected. Release of $^{51}$Cr is monitored to indicate cell lysis. Lysis of MICA-expressing cells by the activated NK cells at levels above controls indicates NKG2D-specific activation.

To screen for NKG2D modulators, the activated NK cells are incubated with candidate agents prior to exposure to the $^{51}$Cr-labeled target cells. Compounds that significantly decrease killing of the NKG2D ligand-bearing target cells are identified and evaluated further.

EXAMPLE 2

Assay for NKG2D Internalization

Cells expressing human NKG2D are cultured at 37° C. for one or more hours in the presence of a biotin-labeled anti-NKG2D antibody. As a control, the NKG2D+ cells are cultured with the biotin-labeled anti-NKG2D at 4° C. in the presence of 0.05% sodium azide to prevent internalization. The cells are washed to remove excess antibody, and then stained with a fluorescent dye-labeled streptavidin to detect the biotin-conjugated NKG2D antibody. Internalization is then evaluated by fluorescent microscopy or flow cytometry. A decrease in the amount of NKG2D on the cell surface after culture with the biotin-labeled anti-NKG2D antibody at 37° C. compared with the cells incubated with the biotin-labeled anti-NKG2D antibody at 4° C. is one indicator of internalization. This may be further verified by fixation and permeabilization of the cells and staining with a fluorescent dye-labeled second step antibody that will detect the primary anti-NKG2D antibody. If internalized, the second step antibody will detect the primary anti-NKG2D antibody inside of the cells cultured at 37° C., as visualized by fluorescent microscopy.

EXAMPLE 3

NKG2D Blockage Prevents Autoimmune Diabetes in Mice

The following experiments were performed to test the effect of NKG2D blockade on development of Type I diabetes in an animal model system, the NOD mouse (Ogasawara et al., *Immunity*, 20:757-767, 2004).

Mice, Reagents, Cytokines and Antibodies

NOD mice were purchased from Taconic (Germantown, N.Y.). NOD.scid mice were purchased from the Jackson Laboratory (Bar Harbor, Me.). 8.3 TcR-transgenic NOD mice have been described (Verdaguer et al., *J Exp Med*, 186:1663-1676, 1997). All mice were maintained under specific pathogen-free conditions in the UCSF animal facility and experiments were performed according to the guidelines of the UCSF Committee on Animal Research. Diabetes was diagnosed when the blood glucose level was greater than 300 mg/dL on two consecutive measurements. The blood glucose levels were measured by using a blood glucose monitor (Walgreen's, Deerfield, Ill.).

Anti-mouse NKG2D mAb, clones CX5 and CX6 (rat IgG1 isotype), were generated as described (Ogasawara et al., *Immunity*, 18:41-51, 2003) and anti-mouse NKG2D mAb clone 191004 (rat IgG2a isotype) was obtained from R&D Systems (Minneapolis, Minn.). All anti-NKG2D mAbs recognize the NKG2D extracellular domain and efficiently block the binding of NKG2D to its ligands. For in vivo injection, a purified CX5 antibody that did not contain detectable endotoxin (<0.3 pg/injection) was utilized. Control rat IgG was purchased from Sigma (St. Louis, Mo.). Anti-mouse pan RAE-1 mAb (clone 186107, rat IgG2b isotype) binds to RAE-1α, β, γ, δ, and ε. NRP-V7/H-2$K^d$ and TUM/H-2$K^d$ (control) tetramers were produced as described (Amrani et al., *Nature*, 406:739-742, 2000) or from the NIH Tetramer Facility (Atlanta, Ga.). TUM/H-2$K^d$ tetramer did not bind to NRP-V7/H-2$K^d$ tetramer-positive cells. Other antibodies were purchased from BD PharMingen or eBioscience (San Diego, Calif.).

Preparation of Islets Cells from the Pancreas

The mouse islets were isolated as follows. Briefly, 0.3 mg/ml collagenase P (Roche Molecular Biochemicals, Indianapolis, Ind.) was injected into the pancreatic duct. The distended pancreases were removed and incubated at 37° C. for 13-17 min. The islets were purified by centrifugation on Eurocollin-Ficoll gradients that comprised four different densities (1.108, 1.096, 1.069, and 1.037). After centrifugation, the tissue fragments at 1.069/1.096 were collected and washed. Thereafter, to obtain single cells, islets cells were dissociated by non-enzymatic cell dissociation solution (Sigma, St. Louis, Mo.).

Immunofluorescence, Flow Cytometry and Microscopy

For detection of NKG2D, cells (~1×10$^6$) were stained with 0.25 μg biotinylated or PE-labeled anti-NKG2D mAb (clone 191004). Cells were co-stained with FITC-conjugated anti-CD8, APC-conjugated anti-CD8, FITC-conjugated anti-CD44, or FITC-conjugated anti-Ly-6C. To detect RAE-1, cells were stained with a biotinylated anti-pan RAE-1 mAb that recognizes all five known RAE-1 proteins (Lodoen et al., *J Exp Med*, 197:1245-1253, 2003) or anti-RAE-1 mAb (clone CX1) (Ogasawara et al., supra, 2003). PE-conjugated streptavidin or APC-conjugated streptavidin was used to detect biotinylated mAbs. The cells were incubated with mAbs for 20 min and washed with PBS containing 0.01% $NaN_3$. Cells were analyzed by using a BD FACSCALIBUR flow cytometer (Becton Dickinson, San Jose, Calif.) or a small desktop GUAVA personal cell analysis system with GUAVA VIACOUNT and GUAVA EXPRESS software (Guava Technologies, Inc., Hayward, Calif.). Viable lymphocyte populations were gated based on forward and side scatter profiles and by lack of propidium iodide staining. For immunohistochemistry, organs were snap frozen in OCT media and sections were prepared and stained by conventional techniques. The images were acquired using a DELTAVISION microscope (Applied Precision, Issaquah, Wash.) and the computational deconvolution was carried out using SOFTWORX software (Applied Precision).

Quantitative RT-PCR

Quantitative (real-time) PCR was carried out using an ABI 7700 (Applied Biosystems) instrument, according to the manufacturer's instructions. Probes were purchased from Applied Biosystems. RAE-1 specific probes and primers were described previously (Ogasawara et al., supra, 2003). The universal primers used to detect all known RAE-1 transcripts were: sense, 5'-ctagtgccac ctgggaattc a-3' (SEQ ID NO:6); anti-sense 5'-catcattagc tgatctccag ctca-3' (SEQ ID NO:7), and the probe was 5'-6-FAM-catcagtgac agttacttct tcaccttcta cacagaga-Tamra-3' (SEQ ID NO:8). Total RNA was treated with DNase I, and then first-strand cDNA was synthesized using random hexamer primers. The cycling conditions for real-time PCR were: 50° C. for 10 min, followed by 50 cycles at 95° C. for 30 sec, and 60° C. for 2 min. Data were analyzed by using the Sequence Detector v1.7 Analysis Software (Applied Biosystems). Statistical analysis was performed using a two-sample t-test.

Adoptive Transfer Studies—NOD T Cells Transferred into NOD.Scid Mice

T cells were isolated from spleens and lymph nodes of diabetic 16-week old NOD mice by magnetic cell sorting using MACS (Miltenyi Biotec Inc., Germany). T cells (purity >98%) were enriched by negative selection with depletion of CD19+, CD24+, and MHC class II+ cells. About 7.5×10$^6$ T cells were transferred into 4-5 week-old NOD.scid mice by injection into the tail vain. Blood glucose levels in adoptively transferred mice were examined weekly.

Adoptive Transfer Studies—8.3 TcR-Transgenic T Cells into NOD Mice

Adoptive T cell transfer was performed as previously described (Serra et al., *Proc Natl Acad Sci USA*, 99:15566-15571, 2002). Briefly, 8.3 TcR-transgenic lymphocytes were isolated from the lymph nodes and spleens. T cells (purity >95%) were enriched by negative selection by magnetic sorting using a MACS. Approximately $1 \times 10^7$ T cells labeled with CFSE (5 µM) were transferred into 10 week-old NOD mice by injection in the tail vain on day 0. Anti-NKG2D mAb (CX5) or cIg (200 µg/injection) was injected into the recipient NOD mice on days −1, +1 and +5.

Expression of RAE-1 in the Pancreas of Pre-Diabetic NOD Mice

Figure 1B:
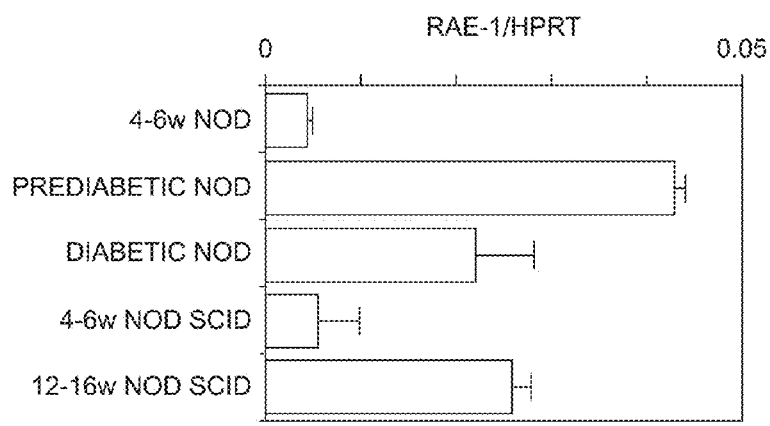
FIG. 1(b) shows RAE-1 mRNA measured by quantitative RT-PCR in pancreatic tissue from NOD and NOD.scid mice 4-6 weeks and 12-16 weeks of age.
Figure 1C:
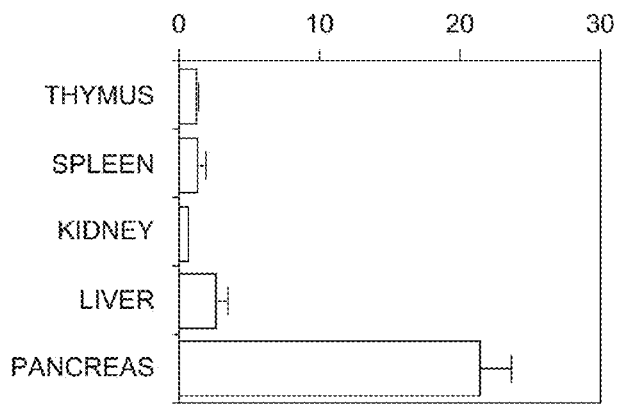
FIG. 1(c) shows RAE-1 mRNA measured by quantitative RT-PCR in different tissues of pre-diabetic NOD. Representative data are shown and expressed as fold-induction of RAE-1 transcription. Fold-induction was calculated according to the formula: Fold induction=amount of RAE-1 transcript in the pre-diabetic NOD organ normalized to HPRT divided by the amount of RAE-1 transcript in the young NOD organ normalized to HPRT.

To investigate whether interactions between NKG2D and RAE-1 are involved in the development of autoimmune diabetes, a quantitative RT-PCR assay was developed to detect transcripts of all known RAE-1 genes. Abundant RAE-1 transcripts were detected in the pancreases of late stage pre-diabetic NOD mice (12-16 weeks-old), but not in the pancreases of age-matched BALB/c mice (FIG. 1a). Although comparatively less pronounced, RAE-1 transcripts were also detected in the pancreases of 4-6 week-old NOD mice. RAE-1 was also detected in the pancreases of adult NOD.scid mice (that lack B and T cells) (FIG. 1b). Together, these results indicated that RAE expression is independent of an ongoing autoimmune response. To examine whether RAE-1 is selectively up regulated in the pancreas with age, the levels of RAE-1 transcripts in a particular organ from young NOD mice were compared with those in the same organ in late-stage pre-diabetic NOD mice. By this criterion, RAE-1 was increased relatively more in the pancreas of the pre-diabetic mice with age, compared with the liver, spleen, kidney and thymus (FIG. 1c).

Figure 1D:
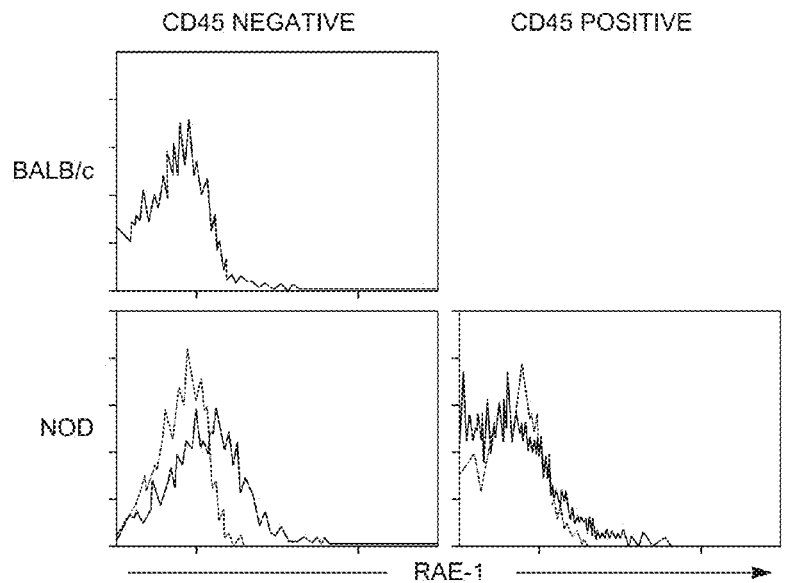
FIG. 1(d) shows RAE-1 expression on CD45⁻ NOD pancreatic cells analyzed by flow cytometry using anti-CD45 and anti-RAE-1 mAb.
Figure 1E:
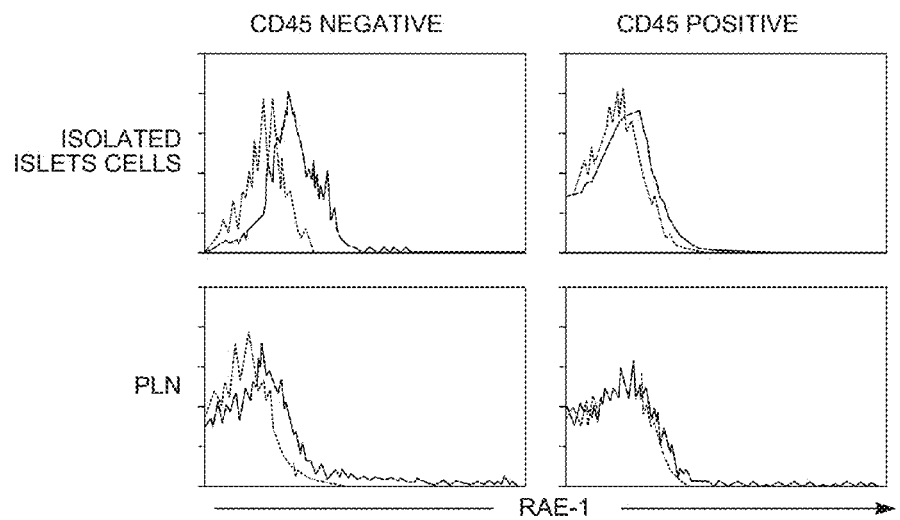
FIG. 1(e) shows RAE-1 expression on CD45– islet cells isolated from pancreas (upper panel) and draining pancreatic lymph nodes (PLN) (lower panel) in NOD mice stained with anti-CD45 and anti-RAE-1 mAb.

To determine whether RAE-1 proteins were expressed on the cell surface, pancreatic cells were isolated from pre-diabetic NOD and non-diabetic BALB/c mice. Cells isolated by enzymatic digestion of the pancreas were stained with anti-RAE-1 and anti-CD45 mAb (which distinguishes infiltrating $CD45^+$ hematopoietic cells from $CD45^-$ non-hematopoietic pancreatic islet cells). CD45-positive hematopoietic lineage cells were detected infiltrating the pre-diabetic NOD pancreas, but not the non-diabetic BALB/c pancreas (FIG. 1d). RAE-1 proteins were detected predominantly on the CD45-negative non-hematopoietic pancreatic cells in NOD mice, but were not found on the pancreatic cells in BALB/c mice. Using density gradient separation techniques, the islets were isolated from NOD pancreases and also harvested from the pancreatic lymph nodes (PLN) of these mice. Single-cell suspensions from the isolated islets and PLN were stained with anti-RAE-1 and anti-CD45 mAb and were analyzed by flow cytometry. RAE-1 was present at low levels on most $CD45^-$ islet cells, but not on $CD45^+$ hematopoietic cells in the pancreas or PLN (FIG. 1d, e). These results indicated that RAE-1 transcripts and proteins were present in the pancreas of pre-diabetic NOD mice, but not non-diabetic BALB/c mice, and indicated that expression of RAE-1 may precede disease onset and contribute to disease progression in NOD mice.

$CD8^+$ T Cells Infiltrating the NOD Pancreas Express NKG2D

Figure 2B:
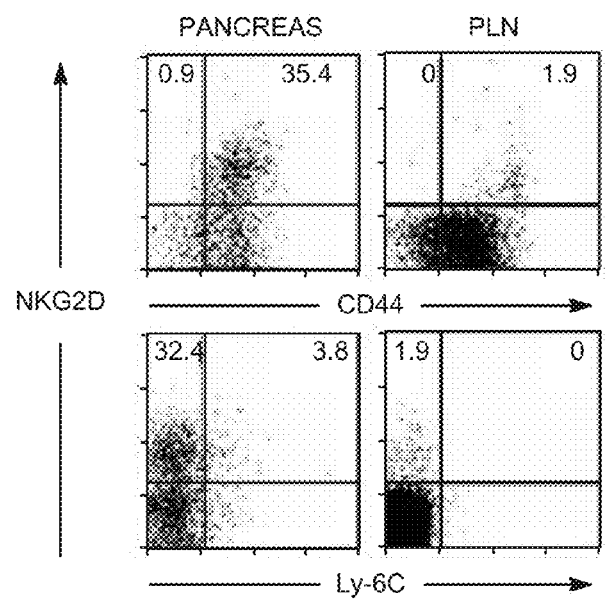
FIG. 2(b) is a graphic illustration of expression of CD44 and Ly-6C on pancreatic and PLN $NKG2D^+$ $CD8^+$ T cells. Cells were stained with monoclonal antibodies against CD8, NKG2D, and CD44 or Ly6C and the results are shown for gated CD8+ T cells.

Since the development of diabetes in NOD mice requires both $CD4^+$ and $CD8^+$ T cells, NKG2D expression was analyzed on T cells isolated from the peripheral immune tissues and on the infiltrating leukocytes in the pancreases of NOD mice. As shown in FIG. 2a, NKG2D was detected on a subset of the $CD8^+$ T cells infiltrating the pancreas in 10 and 25 week-old NOD mice. The percentages of pancreas-infiltrating $NKG2D^+$ $CD8^+$ T cells increased with disease progression (FIG. 2a). A smaller fraction of $NKG2D^+$ $CD8^+$ T cells was detected in the PLN and spleen (FIG. 2a, b). Furthermore, $NKG2D^+$ $CD8^+$ T cells in the pancreas and PLN were found to express high levels of CD44, but not Ly-6C (FIG. 2b). A population of $CD8^-$ $NKG2D^+$ leukocytes (which did not express CD3) was also observed in the leukocytes infiltrating the NOD pancreas (FIG. 2a) and many of these cells co-expressed NK cell and myeloid cell antigens. As reported for normal non-diabetic mouse strains (Jamieson et al., *Immunity*, 17:19-29, 2002), NKG2D was not detected on $CD4^+$ T cells or on $B220^+$ B cells in the pancreas or peripheral lymphoid tissues of either 10 week or 25 week-old NOD mice.

Figure 2C:
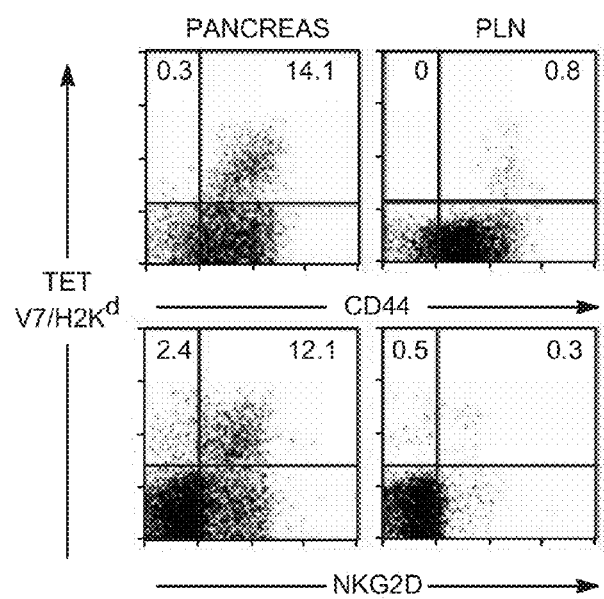
FIG. 2(c) is a graphic illustration of expression of NKG2D and CD44 on pancreatic and PLN NRP-V7/H-2K$^d$ tetramer-positive $CD8^+$ T cells. Cells were stained with NRP-V7/H-2K$^d$ tetramer and with monoclonal antibodies against CD8 and CD44 or NKG2D. The indicated percentages of NRP-V7/H-2K$^d$ tetramer-positive $CD8^+$ T cells (gated on $CD8^+$ T) cells are shown.
Figure 2D:
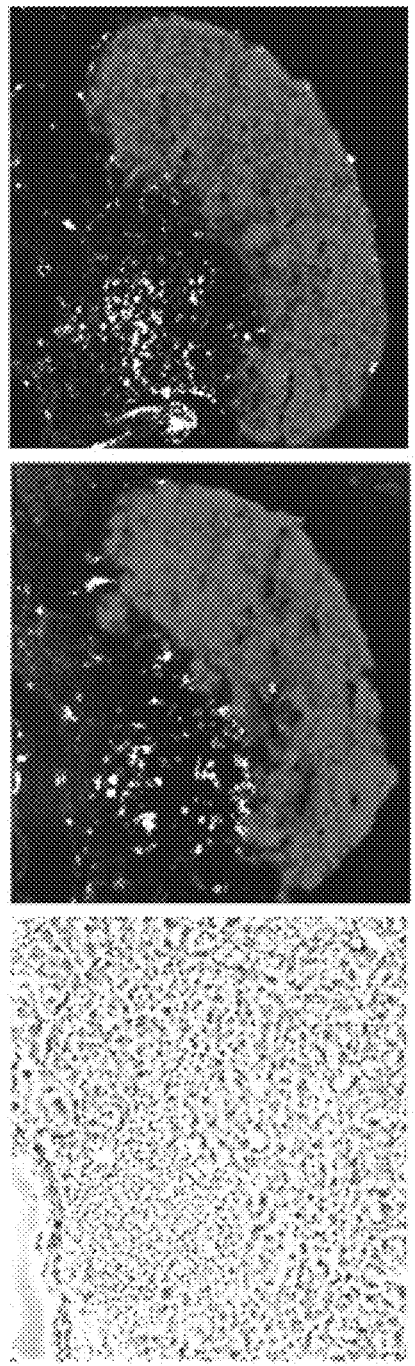
FIG. 2(d) shows micrographs of $NKG2D^+$ $CD8^+$ T cells accumulated near the islets. Sequential frozen sections of pancreas isolated from pre-diabetic NOD mice 16 weeks of age were stained with anti-CD8, anti-CD68 (macrophage marker), anti-NKG2D and anti-insulin antibodies. Left: phase-contrast differential image, Center: CD8 (red), NKG2D (green), and insulin (blue); Right: CD68 (red), NKG2D (green), and insulin (blue). Double-positive $CD8^+$ $NKG2D^+$ T cells and $CD68^+$ $NKG2D^+$ macrophages are yellow.

Recent studies revealed that a substantial proportion of autoreactive $CD8^+$ T cells in NOD mice recognize a peptide from the glucose-6-phosphatase catalytic subunit-related protein (IGRP) that is presented by $H-2K^d$. A mimotope peptide, NRP-V7 (KYNKANVFL, set forth as SEQ ID NO:5), functions as a super-agonist in NOD mice expressing the 8.3 TcR. NRP-V7-reactive $CD8^+$ T cells accumulate in the pancreas of NOD mice and play a critical role in diabetogenesis. $CD8^+$ T cells in the pancreas and PLN were co-stained with NRP-V7/$H-2K^d$ tetramers and anti-NKG2D. Almost all NRP-V7/$H-2K^d$ tetramer-positive $CD8^+$ T cells infiltrating the pancreas expressed NKG2D and $CD44^{high}$ (FIG. 2c). Similarly, $NKG2D^+$ $CD8^+$ T cells in the pancreas were $CD44^{high}$, but Ly-$6C^-$ (FIG. 2b), a phenotype consistent with effector $CD8^+$ T cells (Cerwenka et al., *J Immunol*, 161:97-105, 1998). Notably, few NRP-V7/$H-2K^d$ tetramer-positive $CD8^+$ T cells were detected in the PLN (FIG. 2c). Immunohistochemistry revealed that $NKG2D^+$ $CD8^+$ T cells accumulated in the islets of pre-diabetic NOD mice, near insulin-producing beta cells (FIG. 2d). In addition to $CD8^+$ T cells, a subset of the CD68-positive cells (macrophages) in the pancreas also expressed NKG2D (FIG. 2d).

Treatment with Neutralizing Anti-NKG2D mAb In Vivo Prevents Autoimmune Diabetes

Figure 3A:
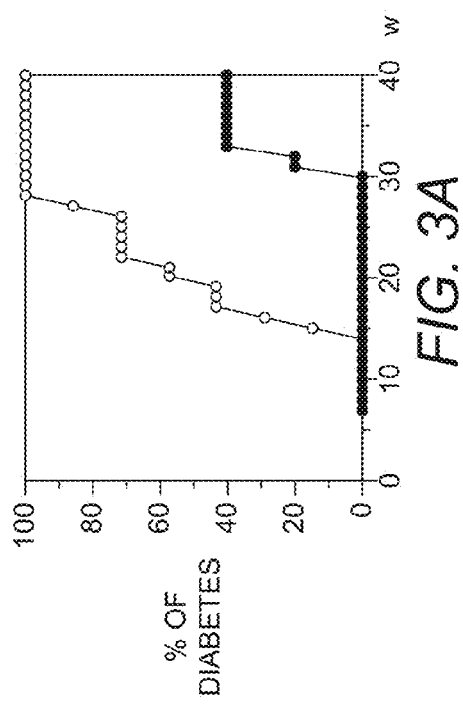
FIG. 3(a) is a graphic illustration of the effect of treatment with anti-NKG2D mAb from 7-25 weeks of age on the proportion of NOD mice who developed diabetes. Dark circles: NOD mice treated with anti-NKG2D mAb (n=7) (bi-weekly at 200 μg/mouse IP); light circles, NOD mice treated with sterile non-pyrogenic PBS (n=7). Diabetes was diagnosed when the blood glucose level was greater than 300 mg/dL on two consecutive measurements.
Figure 3B:
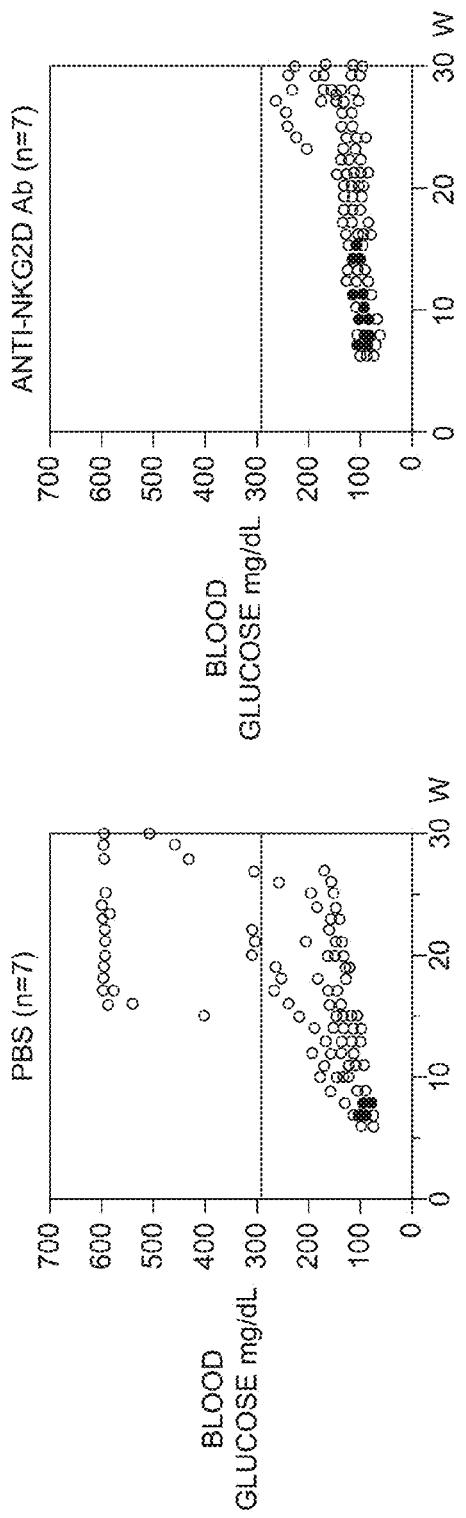

The expression of NKG2D on the infiltrating $CD8^+$ T cells and NKG2D ligands on the pre-diabetic islets indicated a role for these molecules in diabetogenesis. This hypothesis was tested, by treating pre-diabetic NOD mice with a neutralizing anti-NKG2D mAb. The CX5 anti-mouse NKG2D mAb blocks binding of NKG2D to its ligands, and incubation of NKG2D-bearing cells with CX5 resulted in modulation and internalization of the receptor. Importantly, treatment of mice in vivo with CX5 did not deplete $NKG2D^+$ NK cells or $CD8^+$ T cells. NOD mice were treated with anti-NKG2D mAb from 7-25 weeks of age. Mice treated with diluent only developed diabetes beginning at 15 weeks of age and all (n=7) had disease by 28 weeks (FIG. 3a, b). In contrast, none of the NOD mice treated with anti-NKG2D (n=7) developed diabetes at 30 weeks of age, although antibody treatment was halted 5 weeks earlier (FIG. 3a, b).

As a more stringent analysis, anti-NKG2D mAb treatment was tested for prevention of disease onset in 13 week-old pre-diabetic mice with established insulitis. Mice given control IgG developed diabetes beginning at 15 weeks of age. By contrast, no diabetes occurred in any of the NOD mice during the 12 weeks of anti-NKG2D treatment (FIG. 3c, d). Remarkably, most of the anti-NKG2D treated mice remained disease-free 7 weeks after halting therapy (FIG. 3c, d). Thus, NKG2D blockade prevented the progression of diabetes not only in young mice with insulitis, but also in mice at a late pre-diabetic stage with the imminent onset of islet destruction.

Side effects of anti-NKG2D mAb treatment were not observed either by gross examination or histological analysis. Thus, anti-NKG2D mAb treatment is an efficient therapy to prevent diabetes, at least as long as antibody is administered continuously.

Figure 4B:
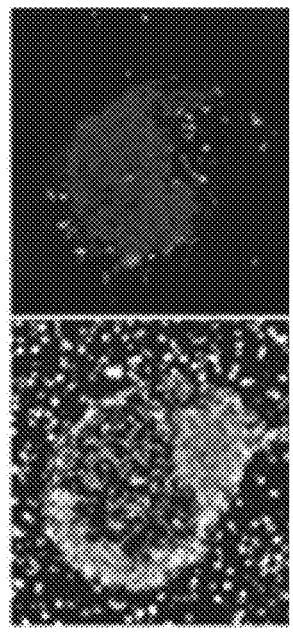
FIG. 4(b) represents photomicrographs of pancreatic islets of 16 week-old NOD mice treated with control Ig from 7 weeks of age. Frozen pancreas sections were prepared and stained from 16 week-old NOD mice treated with control Ig. Left: DAPI (nuclei) staining; Right: CD8 (red), NKG2D (green) and insulin (blue).
Figure 4C:
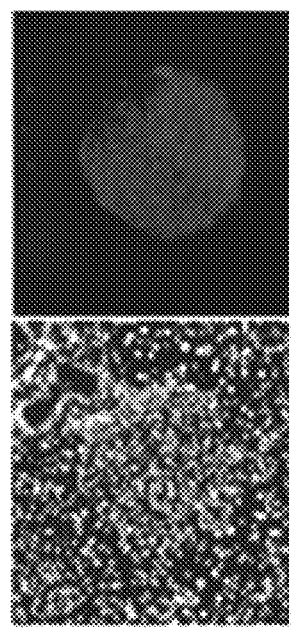
FIG. 4(c) represents photomicrographs of pancreatic islets of 16-week old NOD mice treated with anti-NKG2D mAb treatment (200 μg/mouse IP bi-weekly) from 7 weeks of age that were prepared and stained as in panel (b).
Figure 4A:
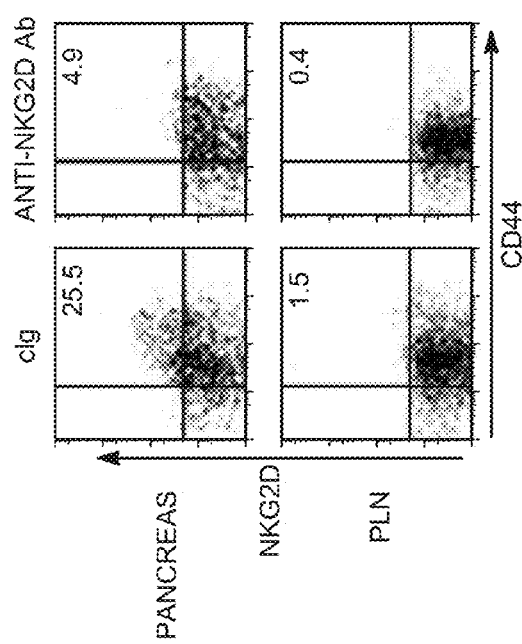
FIG. 4(a) is a graphic illustration of the analysis of leukocytes infiltrating the pancreas and pancreatic lymph nodes of 11 week old NOD mice treated with control Ig (cIg) or anti-NKG2D mAb (200 μg/mouse IP bi-weekly beginning at 7 weeks of age) that had been stained with anti-CD8, anti-NKG2D, and anti-CD44 and subjected to flow cytometry. Results shown are gated on CD8+ T cells.

To examine the mechanism of anti-NKG2D mAb-mediated therapy, leukocytes isolated from the pancreas and PLN of control Ig and anti-NKG2D mAb-treated NOD mice were analyzed. $CD8^+$ T cells co-expressing NKG2D and high levels of CD44 were present in the pancreas of control Ig-treated mice. As expected, NKG2D expression was significantly reduced on $CD8^+$ T cells, but CD44 expression was identical in the pancreas of mice treated with anti-NKG2D mAb compared to that of mice treated with control Ig (FIG. 4a). By contrast, $CD8^+$ T cells expressing NKG2D were relatively infrequent in the PLN of both control and anti-NKG2D mAb treated mice, indicative of preferential localization of the $NKG2D^+$ $CD8^+$ T cells in the pancreas (consistent with the results presented in FIG. 2 for untreated NOD mice). Immunohistochemical analysis of frozen sections of pancreas from control Ig treated mice indicated abundant $CD8^+$ T cells expressing NKG2D in the pancreas of 16 week-old NOD mice treated with control Ig (FIG. 4b). In contrast, many fewer $CD8^+$ T cells were present in the healthy pancreas of 16 week-old mice that had been treated for nine weeks with anti-NKG2D (FIG. 4c).

Figure 7:
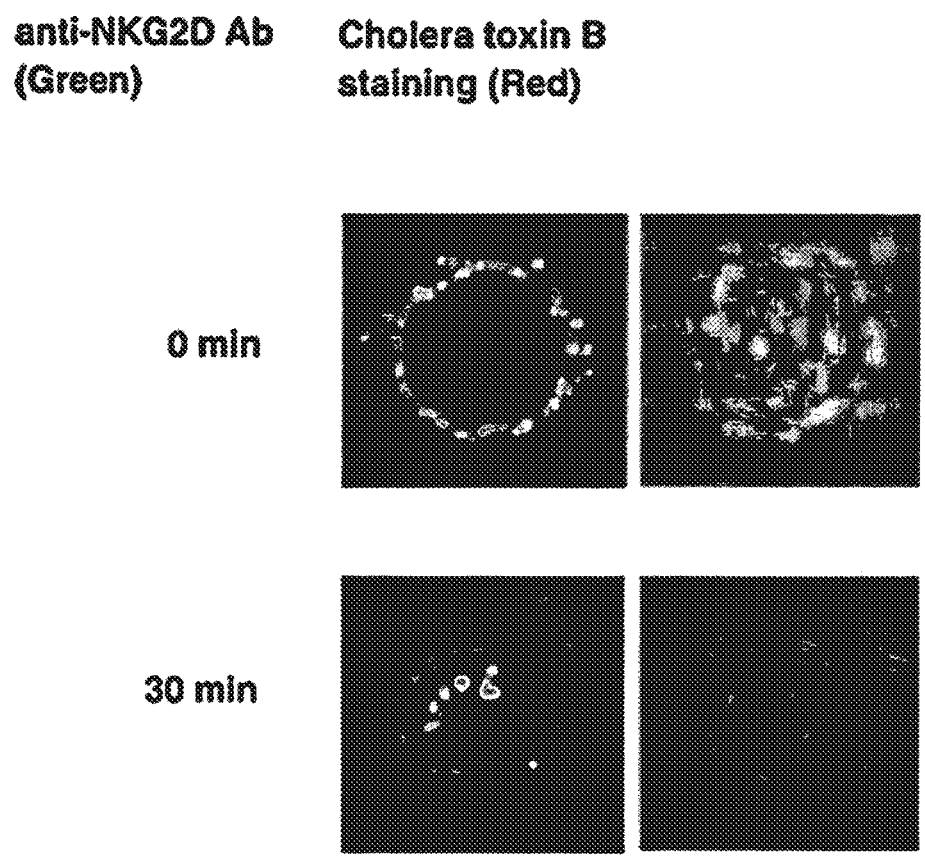
FIG. 7 represents photomicrographs of 8.3 TcR-transgenic NOD lymphocytes cultured with 100 nM IGRP (glucose-6-phosphatase catalytic subunit-related protein) peptide for 3 days and then grown in the presence of 200 U/ml human recombinant IL-2 and 4 ng/ml IL-7 for an additional 5 days. Activated 8.3 TcR-transgenic CD8$^+$ T cells were stained on ice with anti-NKG2D mAb CX5 and counterstained with cholera toxin B to label the cell surface membrane. An aliquot of these stained cells was incubated for 30 minutes at 37° C. and another aliquot was kept on ice. Cells were analyzed by using a fluorescent microscope. In the photomicrograph, NKG2D expression is displayed as green fluorescence and red fluorescence indicates cholera toxin B (membrane) staining. Note that NKG2D was present on the cell surface of cells incubated on ice, but was modulated and internalized in cells cultured at 37° C.
Figure 8:
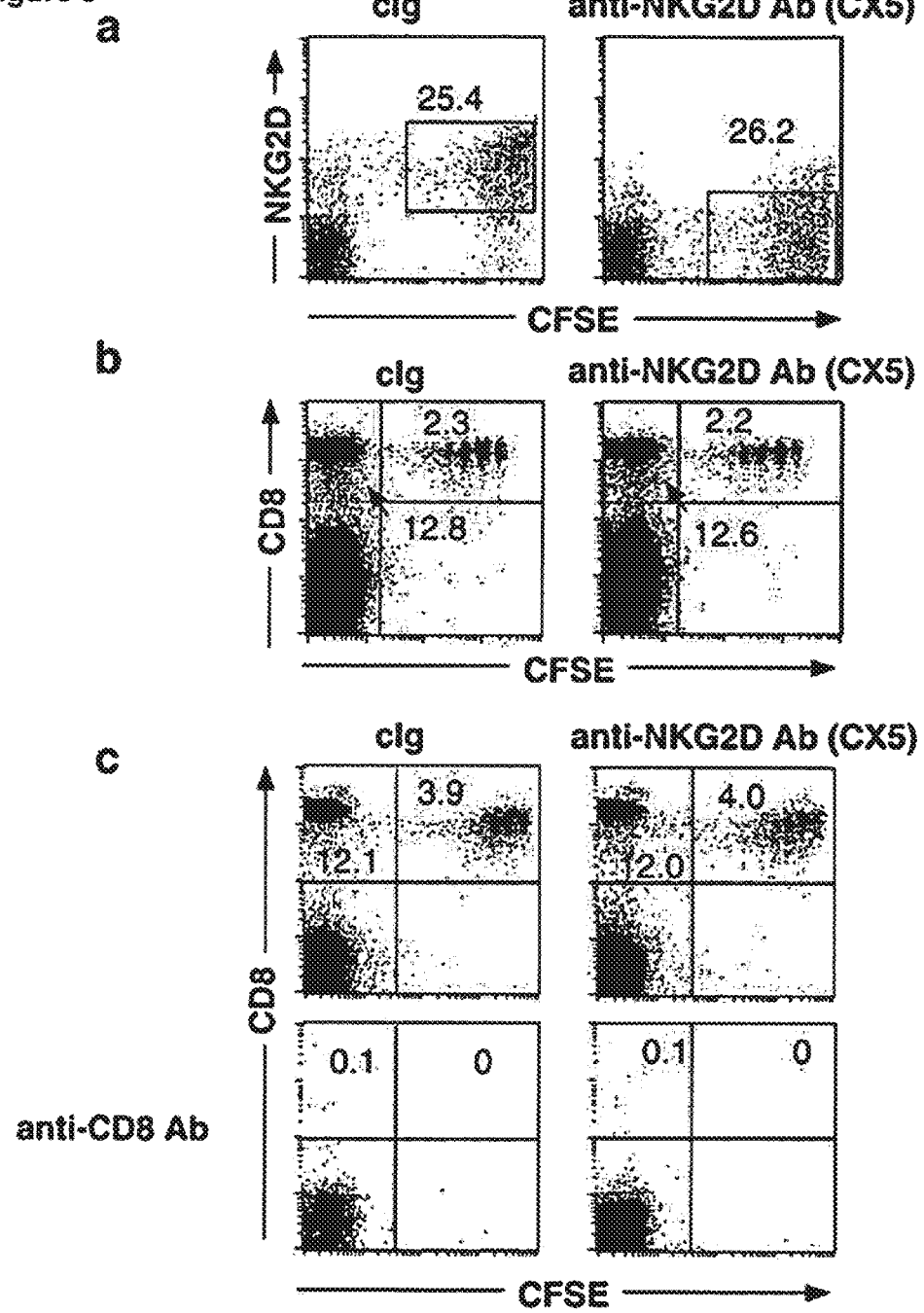
FIG. 8 is a graphic illustration of the effect of anti-NKG2D mAb on NKG2D-bearing CD8$^+$ T cells in vivo. OT-1 ovalbumin (OVA)-specific TcR-transgenic CD8$^+$ T cells were activated with 100 nM OVA peptide for 3 days and then cultured with 200 U/ml human recombinant IL-2 and 4 ng/ml IL-7 for an additional 5 days. NKG2D was expressed on the activated OT-1 T cells (>95%), which were labeled with CFSE and adoptively transferred ($2 \times 10^7$ cells) into C57BL/6 mice. Mice receiving transferred CD8$^+$ NKG2D$^+$OT-1 TcR-transgenic T cells were treated with anti-NKG2D mAb or control rat Ig at −2, 0, and +2 days (200 µg per intraperitoneal injection).
Figure 9:
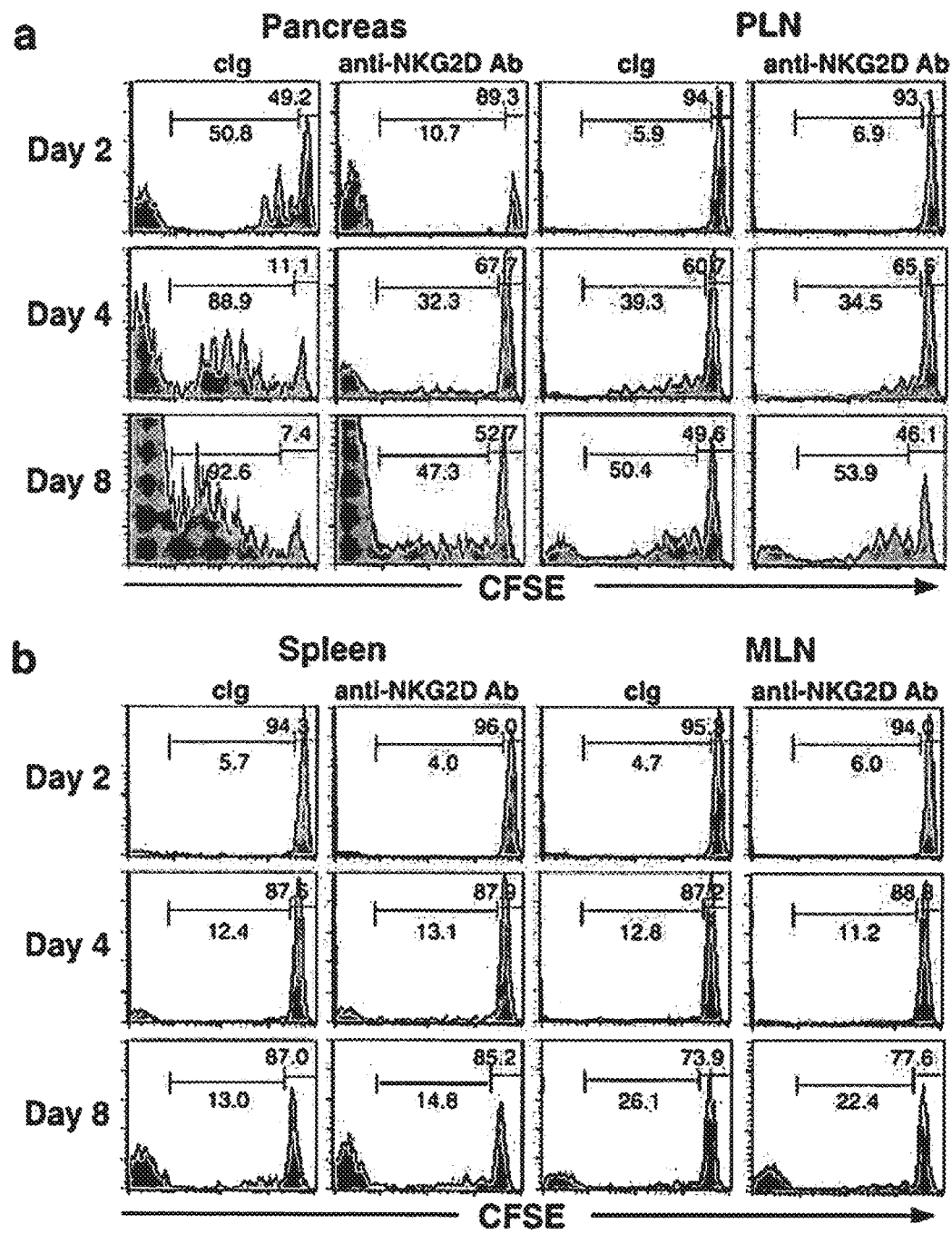
FIG. 9 is a graphic illustration of the effect of anti-NKG2D mAb on autoreactive CD8$^+$ T cell proliferation. 8.3 TcR-transgenic NOD T cells were labeled with CSFE and transferred into wild-type NOD mice, which were treated with control Ig or anti-NKG2D mAb CX5 as described in FIG. 6. Cells harvested from the pancreas, pancreatic lymph nodes, mesenteric lymph nodes and spleen were stained with NRP-V7/H-2K$^d$ tetramer and anti-CD8 mAb and analyzed by flow cytometry. Histograms of lymphocytes gated on CD8-positive NRP-V7/H-2K$^d$ tetramer positive cells are shown. The percentages of proliferating (more than one division) and non-proliferating cells (gated on CFSE$^+$ CD8$^+$ NRP-V7/H-2K$^d$ tetramer$^+$ T cells) are indicated in each histogram. Cells stained with isotype-matched control Ig or controls for tetramer staining demonstrated the specificity of binding of the reagents.
Figure 10:
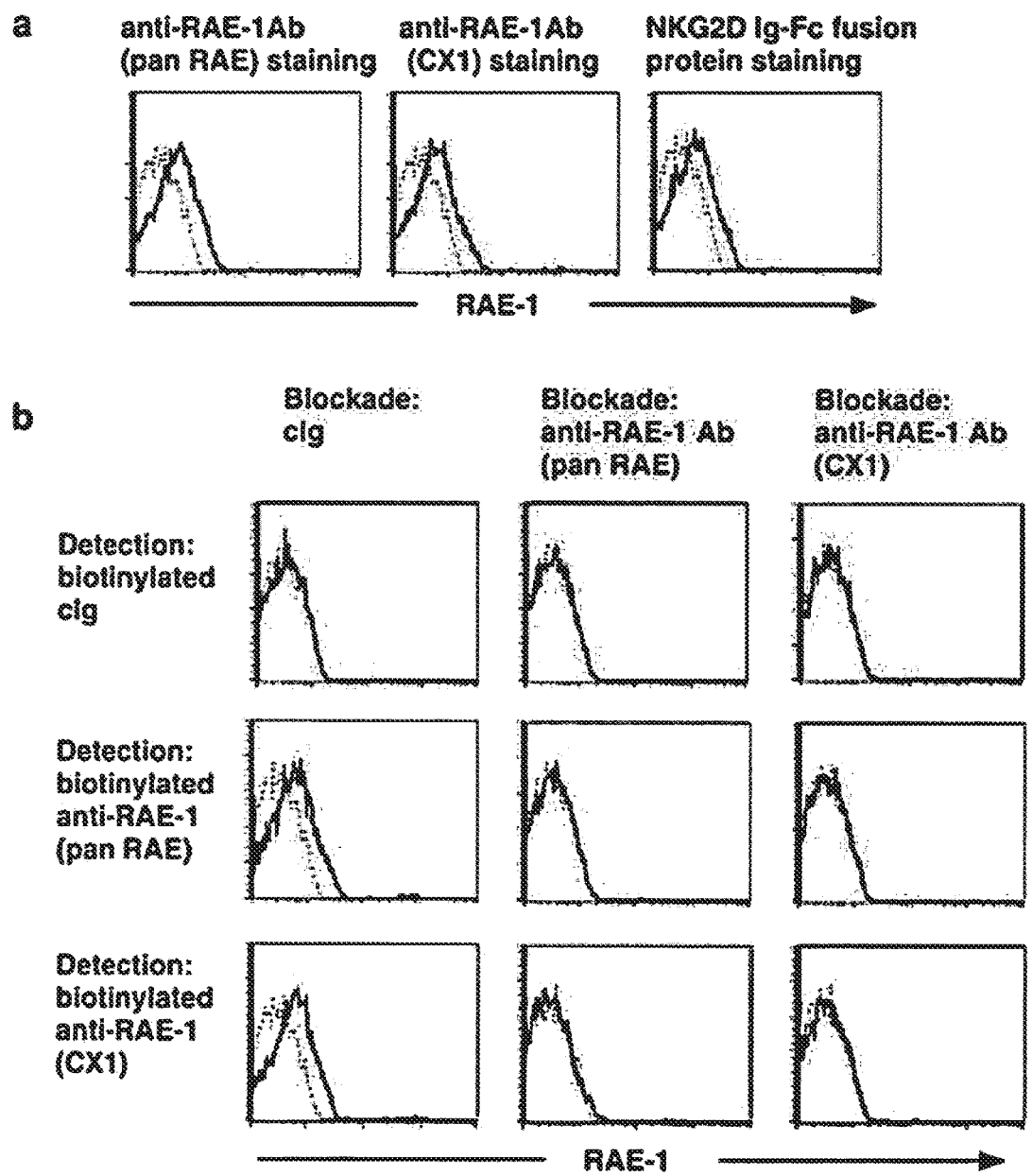
FIG. 10 illustrates the specificity of the staining for NKG2D ligands on NOD pancreas cells.

The leukocytes isolated from the pancreas and PLN of NOD mice treated with control Ig or anti-NKG2D mAb were also analyzed for presence of antigen-specific autoreactive $CD8^+$ T cells. Strikingly, infiltration of autoreactive NRP-V7/H-$2K^d$ tetramer-positive $CD8^+$ T cells into the pancreas was dramatically decreased (~75%) in mice treated with anti-NKG2D mAb (FIG. 4d). The frequency of NRP-V7/H-$2K^d$ tetramer-positive $CD8^+$ T cells was also decreased in the PLN, spleen and peripheral blood of anti-NKG2D mAb-treated mice, compared with control Ig-treated mice (FIG. 4d, e). NKG2D was not detected on $CD8^+$ T cells in mice treated with anti-NKG2D mAb. Because CX5 is a non-depleting anti-NKG2D mAb (See, FIG. 8), the therapy is contemplated to work by modulation of the receptor (See, FIG. 7) and/or inhibition of ligand binding. IFN-γ production by $CD8^+$ T cells isolated from the PLN of mice treated in vivo with control Ig or anti-NKG2D mAb was also examined. Upon stimulation with PMA and ionomycin in vitro, IFN-$γ^+$ $CD8^+$ T cells were detected in cIg-treated NOD mice, whereas fewer IFN-$γ^+CD8^+$ T cells were observed in mice undergoing anti-NKG2D mAb therapy (FIG. 4f). Nonetheless, an understanding of the mechanism(s) is not necessary in order to make and use the present invention.

Figure 5A:
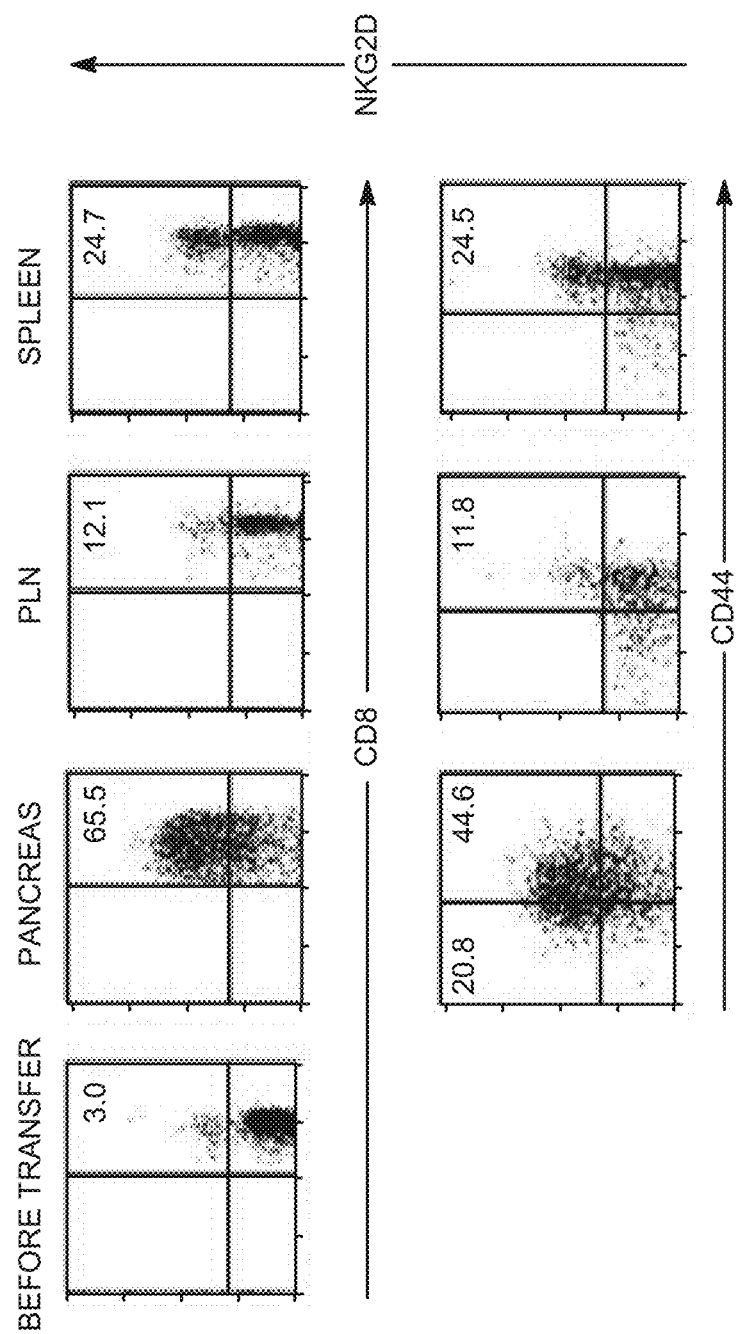
FIG. 5(a) shows $NKG2D^+$ $CD8^+$ T cells in the pancreas, PLN and spleen of NOD.scid mice transplanted with NOD T cells. Prior to adoptive transfer, purified T cells from a diabetic NOD donor were stained with anti-CD8 and anti-NKG2D (a, top left panel). Five weeks after transfer, cells harvested from the pancreas, PLN and spleen were stained with anti-CD8 and anti-NKG2D (a, upper panels) or anti-NKG2D and anti-CD44 (a, lower panels). The percentages of $NKG2D^+$ $CD8^+$T cells (gated on $CD8^+$T cells) are shown.
Figure 5B:
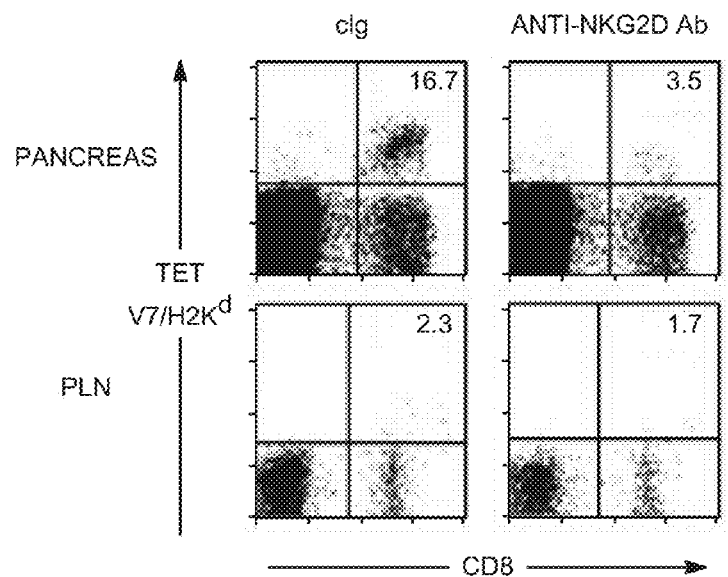
FIG. 5(b) shows accumulation of autoreactive NRP-V7/H-2K$^d$ tetramer-positive $CD8^+$T cells in NOD.scid mice receiving adoptively transferred T cells from diabetic NOD mice treated with anti-NKG2D mAb (200 μg/mouse IP bi-weekly) or control Ig, beginning at the time of transfer and analyzed 10 weeks after transfer. The indicated percentages of autoreactive NRP-V7/H-2K$^d$ tetramer-positive CD8$^+$ T cells were detected gated on live cells.
Figure 5C:
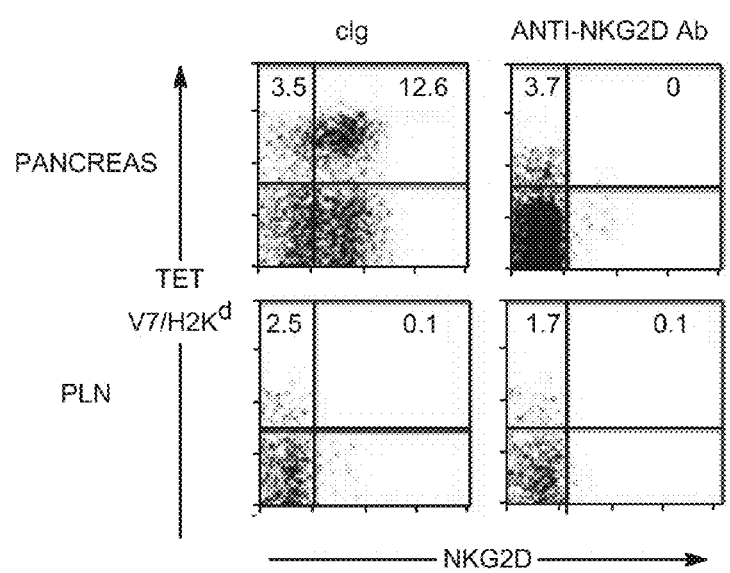
FIG. 5(c) shows the detection of NKG2D on NRP-V7/H-2K$^d$ tetramer-positive T cells from these same treated mice, gated on CD8$^+$ T cells.
Figure 5D:
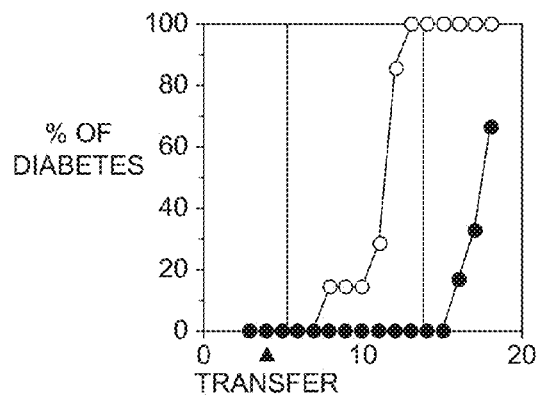
FIG. 5(d) is a graphic illustration of the proportion of NOD-.scid mice transplanted with T cells from diabetic NOD mice that developed diabetes. Five week-old NOD.scid mice that received adoptively transferred T cells from diabetic NOD mice were treated with anti-NKG2D mAb (dark circles; n=6) or control Ig (light circles; n=7) from 5 weeks to 14 weeks of age. Mice were injected intraperitoneally with 200 µg anti-NKG2D mAb CX5, twice weekly. Diabetes was diagnosed when the blood glucose level was greater than 300 mg/dL on two consecutive measurements.

NKG2D Blockade Prevents Diabetes in NOD.scid Mice Receiving Adoptively Transferred T Cells from Diabetic NOD Mice To address whether NKG2D blockade affects effector $CD8^+$ T cells, T cells isolated from diabetic 16 week-old NOD mice were adoptively transferred into NOD.scid recipients (which lack T cells and do not develop diabetes). At the time of transfer, only a small percentage of the $CD8^+$ T cells expressed NKG2D (FIG. 5a). However, 5 weeks post-transfer a substantial number of $NKG2D^+$ $CD8^+$ T cells were detected in the pancreas, PLN, and spleen in the recipient mice (FIG. 5a), suggesting expansion of pre-existing $NKG2D^+$ T cells or acquisition of NKG2D on the transferred $CD8^+$ T cells. Approximately 15% of the $CD8^+$ T cells infiltrating the pancreas in cIg-treated recipient mice were NRP-V7/H-$2K^d$ tetramer-positive, whereas significantly fewer were found in anti-NKG2D mAb-treated mice (FIG. 5b, c). NKG2D was present on most NRP-V7/H-$2K^d$ tetramer-positive autoreactive $CD8^+$ T cells in the control Ig-treated NOD mice, but was not detected on the mice receiving anti-NKG2D mAb therapy (FIG. 5c). Although diabetes developed in all control Ig-treated NOD.scid mice receiving T cells from diabetic NOD mice, none of the anti-NKG2D mAb-treated mice developed diabetes while undergoing therapy (FIG. 5d).

Figure 5E:
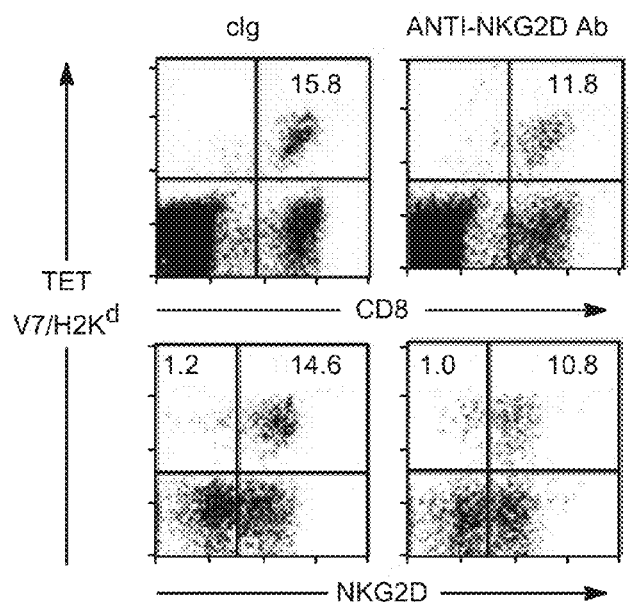
FIG. 5(e) is a graphic illustration of the expansion of autoreactive NRP-V7/H-2K$^d$ tetramer-positive CD8$^+$ T cells after stopping treatment with anti-NKG2D mAb. Four weeks after anti-NKG2D mAb treatment was ceased in NOD.scid mice transplanted with T cells from diabetic NOD mice, animals were sacrificed and the pancreases were analyzed for infiltrating NRP-V7/H-2K$^d$ tetramer-positive, NKG2D$^+$ CD8$^+$ T cells. For comparison, mice treated with control Ig that developed diabetes were also analyzed.

To determine whether anti-NKG2D treatment blocked expansion of pathogenic $CD8^+$ T cells in the NOD.scid recipient mice, anti-NKG2D mAb treatment was stopped after 8 weeks, when all control Ig-treated mice had succumbed to disease. Four weeks after halting anti-NKG2D therapy, diabetes developed in the majority of NOD.scid mice that had received T cells from diabetic NOD donors (FIG. 5d). Furthermore, at this time there was evidence for expansion of NRP-V7/H-$2K^d$ tetramer-positive $NKG2D^+$ $CD8^+$ T cells in the NOD.scid mice (FIG. 5e). These results indicated that anti-NKG2D mAb treatment inhibited the expansion and/or accumulation of $NKG2D^+$ $CD8^+$ T cells in the pancreas. The rapid progression to diabetes shortly after halting therapy indicated that the effector T cells were controlled, rather than depleted, during the period of antibody treatment.

Figure 6A:
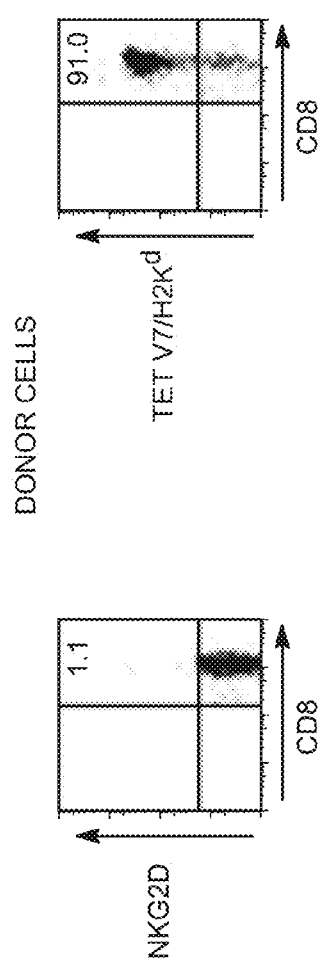
FIG. 6(a) is a graphic illustration of the lack of expression of NKG2D on 8.3 TcR-transgenic NOD T cells before adoptive transfer. Lymphocytes were isolated from the lymph nodes and spleen of young 8.3 TcR-transgenic NOD mice. The 8.3 TcR-transgenic NOD T cells were then purified, by magnetic cell sorting. Prior to T cell transfer, 8.3 TcR-transgenic NOD T cells were stained with anti-CD8 and NRP-V7/H-2K$^d$ tetramers or anti-NKG2D and analyzed by flow cytometry, as shown.
Figure 6B:
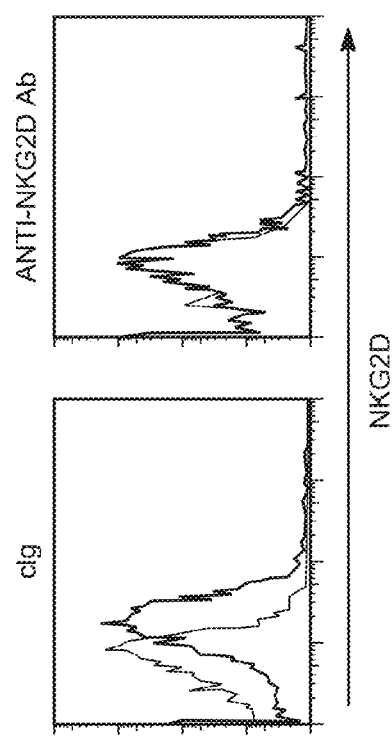
FIG. 6(b) is a graphic illustration of NKG2D expression on 8.3 TcR-transgenic NOD T cells in the pancreas two days after adoptive transfer of 8.3 TcR-transgenic NOD T cells. Two days after adoptive transfer of 8.3 TcR-transgenic NOD T cells, leukocytes were isolated from the pancreas of mice that were treated with control Ig or anti-NKG2D mAb CX5 at the time of cell transfer. Cells were stained with NRP-V7/H-2K$^d$ tetramers and anti-NKG2D and were analyzed by flow cytometry. Expression of NKG2D on the adoptively transferred T cells (identified by gating on NRP-V7/H-2K$^d$ tetramer-positive cells) is shown.
Figure 6C:
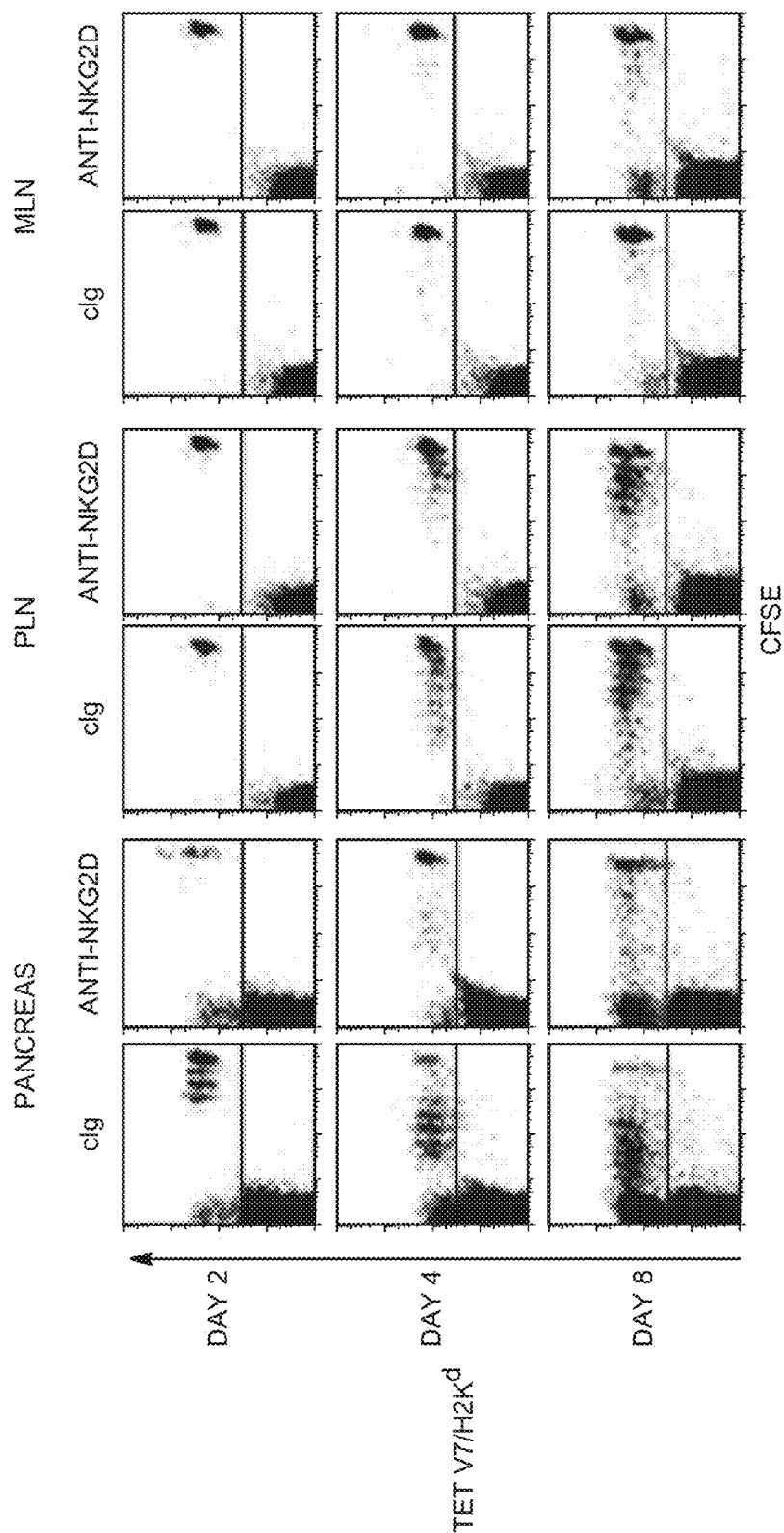
FIG. 6(c) is a graphic illustration of the effect of anti-NKG2D mAb CX5 on the proliferation of 8.3 TcR-transgenic CD8$^+$ NOD T cells in the pancreas. CFSE-labeled 8.3 TcR-transgenic NOD T cells ($1 \times 10^7$) were transferred into 10 week-old wild type NOD mice (day 0). Recipient NOD mice were treated with cIg or anti-NKG2D mAb CX5 (200 µg) on day −1, day 1, and day 5. After transfer, recipient NOD mice were sacrificed and leukocytes were isolated and analyzed from the pancreas, pancreatic lymph node (PLN), and mesenteric lymph node (MLN). Cells shown in (c) were gated on viable CD8-positive lymphocytes.
Figure 6D:
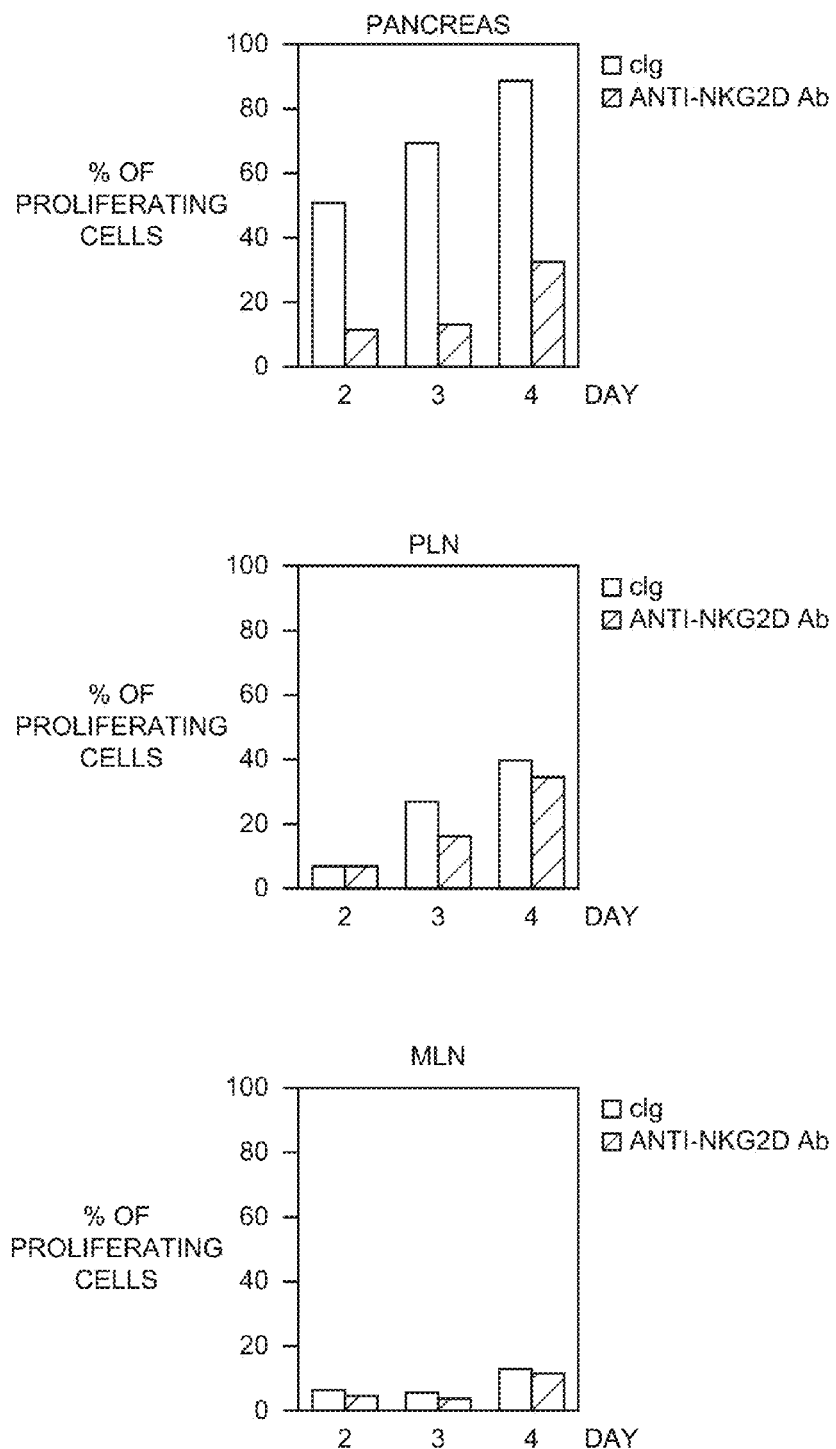
FIG. 6(d) is a graphic illustration of the percentages of CSFS-labeled cells in the control Ig (open bars) and anti-NKG2D mAb (closed bars)-treated mice that had undergone one or more divisions (i.e. proliferating cells) on days 2, 3 and 4 post transfer, calculated by the following formula: % proliferating cells=(Total CFSE$^+$ NRP-V7/H-2K$^d$ tetramer$^+$ CD8$^+$ cells minus non-dividing CFSE$^+$ NRP-V7/H-2K$^d$ tetramer$^+$ CD8$^+$ cells)×100/Total CFSE$^+$ NRP-V7/H-2K$^d$ tetramer$^+$ CD8$^+$ cells.

Anti-NKG2D mAb Therapy Prevents Expansion of Autoreactive $CD8^+$ T Cells in the Pancreas The finding of fewer NRP-V7/H-$2K^d$ tetramer-positive $CD8^+$ T cells in the pancreas of anti-NKG2D treated mice was consistent with the possibility that mAb therapy blocked expansion of the autoreactive T cells. To directly test this hypothesis, 8.3 TcR-transgenic T cells were labeled with CSFE, adoptively transferred into 10 week-old NOD recipients and treated with either control Ig or anti-NKG2D mAb (FIG. 6). Before transfer, donor $CD8^+$ T cells from the lymph nodes and spleens of 8.3 TcR-transgenic NOD mice were >90% NRP-V7/H$2K^d$ tetramer positive but did not express NKG2D (FIG. 6a). Two days later, the transferred CSFE-labeled 8.3 TcR-transgenic NOD $CD8^+$ T cells infiltrating the pancreas of mice treated with control Ig expressed NKG2D (FIG. 6b) and were already proliferating; however, no dilution of CSFE was observed in the transferred T cells present in the pancreatic or mesenteric lymph nodes (FIG. 6c). At days 4 and 8 post transfer, the CFSE-labeled 8.3 TcR-transgenic T cells in the pancreas and pancreatic lymph nodes, but not the mesenteric lymph nodes, of mice treated with control Ig showed extensive proliferation (FIG. 6c). In striking contrast, NKG2D was not detected on the cell surface of the transferred CSFE-labeled 8.3 TcR-transgenic $CD8^+$ T cells in the pancreas of NOD mice treated with anti-NKG2D mAb (FIG. 6b). Furthermore, the expansion of these cells in the pancreas was substantially inhibited compared with the mice treated with control Ig (FIG. 6c). Interestingly, treatment with anti-NKG2D mAb had a much more profound effect on the proliferation of CSFE-labeled 8.3 TcR-transgenic T cells infiltrating the pancreas compared with cells in the lymph nodes. Expansion of the endogenous CSFE-unlabeled T cells in the pancreas detected with the NRP-V7/H$2K^d$ tetramer was also diminished by treatment with anti-NKG2D mAb, compared with control Ig treated mice. Quantitation of the proliferation of the adoptively transferred 8.3 TcR-transgenic T cells infiltrating the pancreas in control Ig and anti-NKG2D mAb treated NOD mice indicated a profound effect of anti-NKG2D therapy on expansion of the autoreactive antigen-specific $CD8^+$ T cells (FIG. 6d).

The data indicate that RAE-1 is present in pre-diabetic pancreas islets of NOD mice and that autoreactive $CD8^+$ T cells infiltrating the pancreas express NKG2D. Treatment with a non-depleting anti-NKG2D monoclonal antibody (mAb) during the pre-diabetic stage completely prevented disease by impairing the expansion and function of autoreactive CD8+ T cells. These findings demonstrate that NKG2D is essential for disease progression and provide a new therapeutic target for autoimmune type I diabetes. These data directly implicate the NKG2D receptor in the functional development of effector functions of the pathogenic CD8+ T cells and indicate that the anti-NKG2D mAb functions therapeutically to block receptor-mediated signals in the absence of frank cell depletion.

EXAMPLE 4

Modulation of Cell Surface Expression of NKG2D by shRNA

The following experiment was performed to examine the effect of inhibitory RNA on NKG2D expression. DNA encoding human NKG2D in a vector containing an IRES-eGFP element was stably transfected into CHO cells. The stably-transfected NKG2D-expressing cells were then transfected (using Lipofectamine and standard methods) with a cDNA encoding mouse CD8 (mCD8) and with a plasmid (the pCR2.1-TOPO vector from InVitroGen) that contained a 22 base pair (bp) cDNA (5'-ggatgggact agtacacatt cc-3' set forth as SEQ ID NO:10) homologous to a segment of human NKG2D (designated shDNA03). As a control to demonstrate specificity, NKG2D-expressing CHO cells were also doubly transfected with mCD8 and with a 22 bp cDNA similar to human NKG2D but with 3 mutated nucleotides (5'-ggatgg-gatt agtatagatt cc-3' set forth as SEQ ID NO:13). Cells in the left panels were transfected only with the plasmid containing the mouse CD8 cDNA (mCD8). The transfected cells were stained with monoclonal antibodies against mouse CD8 and against human NKG2D and were analyzed by flow cytometry. Bivariate dot plots were obtained displaying fluorescence representing (i) mouse CD8 versus human NKG2D and (ii) eGFP (intrinsic green fluorescence resulting from expression of the human NKG2D-IRES-eGFP vector) versus human NKG2D.

The results indicated, first, that cells that expressed mouse CD8 on the cell surface could be easily detected, revealing that they were transfected with the plasmids introduced into the CHO cells. Furthermore, the expression of human NKG2D on the mouse CD8-expressing cells was unaffected by co-transfection with the mouse CD8 plasmid alone or with the plasmid contain the mutant NKG2D construct. By contrast, co-transfection with the homologous NKG2D sequence substantially prevented expression of NKG2D.

EXAMPLE 5

Modulation of Cell Surface NKG2D by Use of an Anti-NKG2D Monoclonal Antibody

The following experiments were performed to evaluate the ability of a monoclonal antibody directed against NKG2D to modulate cell-surface expression of NKG2D.

A human NK cell line (NKL) was stained for 30 min on ice with a biotin-conjugated control IgG (cIg bio) or with biotin conjugated mouse anti-human NKG2D mAb (R&D Systems clone 149810), washed, and an aliquot was incubated overnight at 37° C. The cells were stained with allophycocyanine-conjugated streptavidin either before culture (0 h) or after (16 h) culture, and were subsequently analyzed by flow cytometry. The mean fluorescence intensity (arbitrary units) of anti-NKG2D stained cells before culture was 186 compared with 61 after culture, indicating a 67% decrease in expression of NKG2D on the cell surface of the NK cells treated with anti-NKG2D mAb for 16 hrs.

Figure 12:
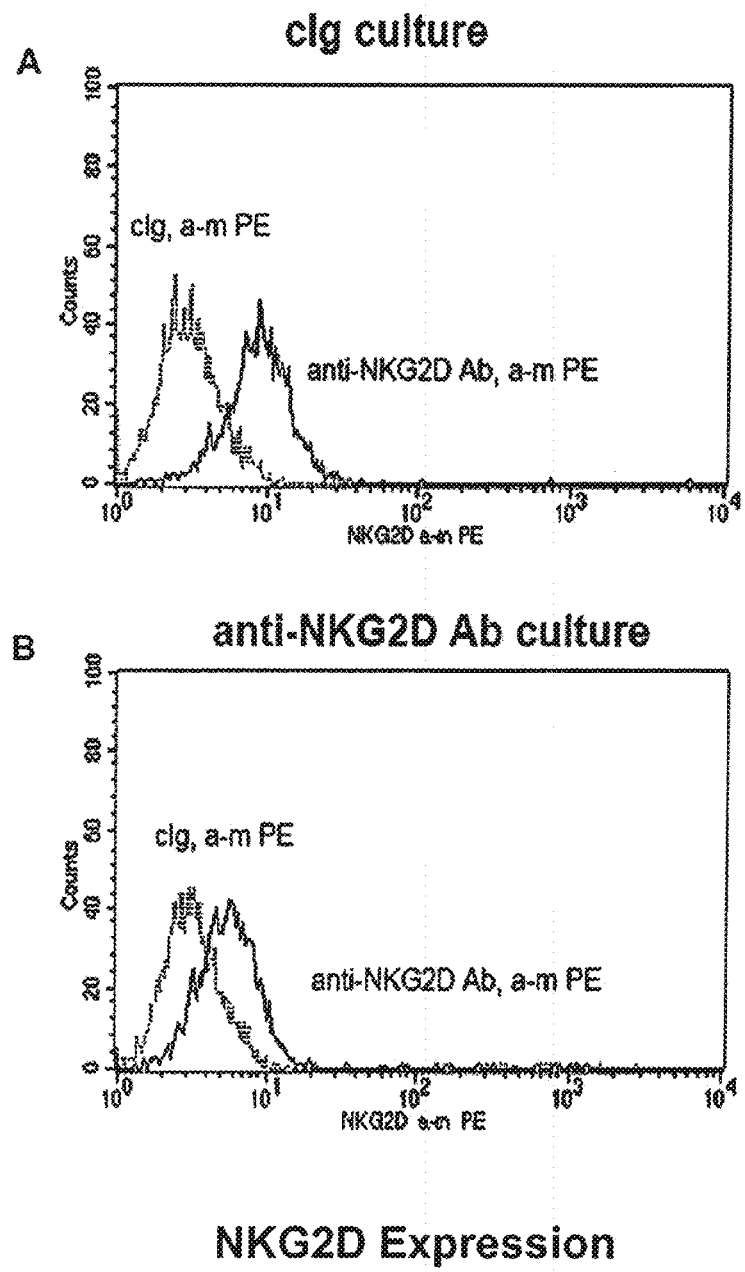
FIG. 12 is a graphic representation of a flow cytometric analysis of NKL cells (a human NK leukemia cell line) that had been incubated with a mouse anti-human NKG2D antibody (clone 149810) for 16 h to stimulate NKG2D internalization (right panel). The left panel shows cells that had been incubated with a control antibody for 16 h. In each case, the cells were briefly washed in an acidic buffer (pH 3.5) to remove any residual bound antibody and then stained with control Ig or anti-NKG2D mAb, followed by phycoerythrin-conjugated goat anti-mouse IgG antibody. The experiment shows that the anti-human NKG2D monoclonal antibody induced internalization (modulation) of NKG2D, whereas incubation with the control Ig did not cause internalization of NKG2D.

NKL cells were cultured for 16 h at 37° C. with either control IgG or with mouse anti-human NKG2D IgG (R&D Systems clone 149810). At the end of the incubation, the cells were washed and treated with acid medium at pH 3.5 for 15 min to remove surface antibody. The cells were then stained with anti-NKG2D antibody followed by PE-labeled goat anti-mouse IgG secondary antibody to detect surface NKG2D. FIG. 12 shows that this anti-NKG2D antibody is effective at stimulating internalization of surface NKG2D on these human cells.

EXAMPLE 6

NKG2D Blockage Prevents Parental Bone Marrow Graft Rejection in F1 Mice

The following experiments were performed to test the effect of NKG2D blockade on development of hybrid resistance (rejection of parental bone marrow grafts by F1 recipients) in an animal model system, (C57BL/6×BALB/c) F1 (CB6F1) mice.

Mice

Approximately 6-8 week old C57BL/6, BALB/c, and CB6F1 mice were purchased from the National Cancer Institute Animal Program (Frederick, Md.). RAE-1ε transgenic mice were generated and backcrossed onto the C57BL/6 background (Ehrlich et al., unpublished observations). DAP12−/− mice on the C57BL/6 background (backcrossed 9 generations) were described previously (Bakker et al., *Immunity*, 13:345-353, 2000), and DAP10−/− were generated from C57BL/6 embryonic stem cells (Phillips et al., unpublished observations). All experiments were performed according to the guidelines of the UCSF Committee on Animal Research.

Reagents, Cytokines and Antibodies

Anti-mouse NKG2D mAb, clone CX5 (rat IgG1 isotype), was generated by immunizing rats with purified mouse NKG2D protein, as described previously (Ogasawara et al., *Immunity*, 18:41-51, 2003). Anti-mouse NKG2D, clone 191004 (rat IgG2a isotype), was produced from a hybridoma resulting from the fusion of a mouse myeloma with B cells from a rat immunized with recombinant mouse NKG2D extracellular domain (R&D Systems, Minneapolis, Minn.). All anti-NKG2D mAbs recognize the NKG2D extracellular domain and efficiently block the binding of NKG2D to its ligands. For in vivo injection, purified anti-NKG2D mAb CX5 and anti-NK1.1 mAb PK136 that did not contain detectable endotoxin (<0.3 pg/injection) were used. The anti-NKG2D mAb CX5 is a blocking antibody that does not deplete NKG2D-bearing NK cells or T cells when injected in vivo (Ogasawara et al., *Immunity*, 20, 757-7567, 2004; Lodoen et al., *J Exp Med*, 197:1245-1253, 2003; and Lodoen et al., *J Exp Med*, 200:1075-108, 2004). Control rat IgG was purchased from Sigma (St. Louis, Mo.). Anti-mouse pan-RAE-1 mAb (clone 186107, rat IgG2b isotype), anti-mouse H60 mAb (clone 205310) and anti-mouse MULT1 mAb (clone 237104) were generated as described (Lodoen et al., supra, 2003; and Lodoen et al., supra, 2004). Other antibodies were purchased from BD PharMingen or eBiosocience (San Diego, Calif.).

Bone Marrow Transplantation

Murine bone marrow was transplanted as described previously (George et al., J Immunol, 163:1859-1867, 1999). Briefly, mAb treatments (200 µg/mouse) were performed 2 days before bone marrow transfer, and recipients were treated with poly I:C (Sigma, 200 µg/mouse) to boost NK cell-mediated graft rejection one day before injection of bone marrow cells (Murphy et al., *J Exp Med,* 166:1499-1509, 1987). On day 0, mice were irradiated by exposure to lethal doses (11Gy) of $^{137}$Cs gamma irradiation, and then 4×10$^6$ BM cells were injected intravenously. Five days after transfer, the mice were given 26 µg of 5-fluoro-2'-deoxyuridine (Sigma, St. Louis, Mo.) intravenously to suppress endogenous thymidine synthesis (George et al., supra, 1999). Thirty min later, the mice were given 3 µCi of 5-[$^{125}$I]iodo-2'-deoxyuridine (Amersham Life Science, Arlington Heights Ill.) intravenously. On day 6, the spleens were removed from recipient mice and counted with a gamma counter.

Generation of BM Chimeric Mice

Briefly, 1×10$^7$ Ly5.2 B6 BM cells were transferred intravenously into NK cell-depleted and irradiated recipient mice (absorbed dose of radiation=11 Gy), as described previously (Ogasawara et al., *Nature,* 391:701-703, 1998). During reconstitution, mice were maintained on antibiotics.

Preparation of NK Cells

NK cells were enriched as described previously (Ogasawara et al., *J Immunol,* 169:3676-3685, 2002). Briefly, spleen cells were incubated with anti-mouse CD4 mAb (clone GK1.5) and anti-mouse CD8 mAb (clone 53-6.7), and thereafter these cells were mixed with magnetic beads coated with goat anti-mouse Ig and goat anti-rat Ig (Advanced Magnetic, Inc, Cambridge, Mass.). CD4, CD8, and surface Ig (sIg)-positive cells were removed by magnetic cell sorting.

Flow Cytometric Analysis

A fusion protein containing the extracellular domain of mouse NKG2D fused to human IgG1 Fc (mNKG2D-Ig) was used to detect NKG2D ligands (Cerwenka et al., *Immunity,* 12:721-727, 2000). A PE-conjugated goat anti-human IgG Fcγ fragment (Jackson ImmunoResearch, West Grove, Pa.) was used as a second step reagent. The cells (1×10$^6$) were stained with 0.5 µg of mNKG2D-Ig and with 0.25 µg of other mAbs. To determine which NKG2D ligands were expressed, cells were stained with a biotinylated anti-pan RAE-1 mAb, which recognizes all five known RAE-1 proteins (i.e. RAE-1α, β, γ, δ and ε), biotinylated anti-H60 mAb or anti-MULT1 mAb. PE-conjugated streptavidin or APC-conjugated streptavidin was used to detect biotinylated mAbs. For detection of NKG2D, cells (~1×10$^6$) were stained with 0.25 µg biotinylated or PE-labeled anti-NKG2D mAb (clone 191004). Cells were co-stained with anti-CD43, anti-Ly6C/G, anti-CD11c, anti-B220, anti-CD3, anti-TER119, anti-NK1.1 and anti-CD49d (DX5) mAbs. The cells were incubated with mAbs for 20 min and washed with PBS containing 0.01% NaN$_3$. Cells were analyzed by using a FACS Calibur (Becton Dickinson, San Jose, Calif.) flow cytometer. Viable lymphocyte populations were gated based on forward and side scatter profiles and by lack of propidium iodide staining.

Cytotoxic Assay

Monoclonal antibody-mediated redirected cytotoxicity assays were performed as described previously (Lanier et al., *J Immunol,* 141:3478-3485, 1988). Target cells were labeled with 50 µCi of Na$_2$($^{51}$Cr)O$_4$ for 2 h at 37° C. in RPMI-1640 medium containing 10% FCS, washed three times with medium, and used in cytotoxicity assays. $^{51}$Cr-labeled target cells (5×10$^3$) and effector cells were mixed in U-bottomed wells of a 96-well microtiter plate at the indicated effector/target (E/T) ratios, in triplicate. After a 4 h incubation period, the cell-free supernatants were collected and radioactivity was measured in a Micro-beta counter (Wallac, Turku, Finland). The spontaneous release was less than 15% of the maximum release. The percentage of specific $^{51}$Cr release was calculated according to the following formula: % Specific lysis=(experimental−spontaneous)release×100/(maximal−spontaneous) release.

Expression of NKG2D Ligands on Mouse BM Cells

Figure 13:
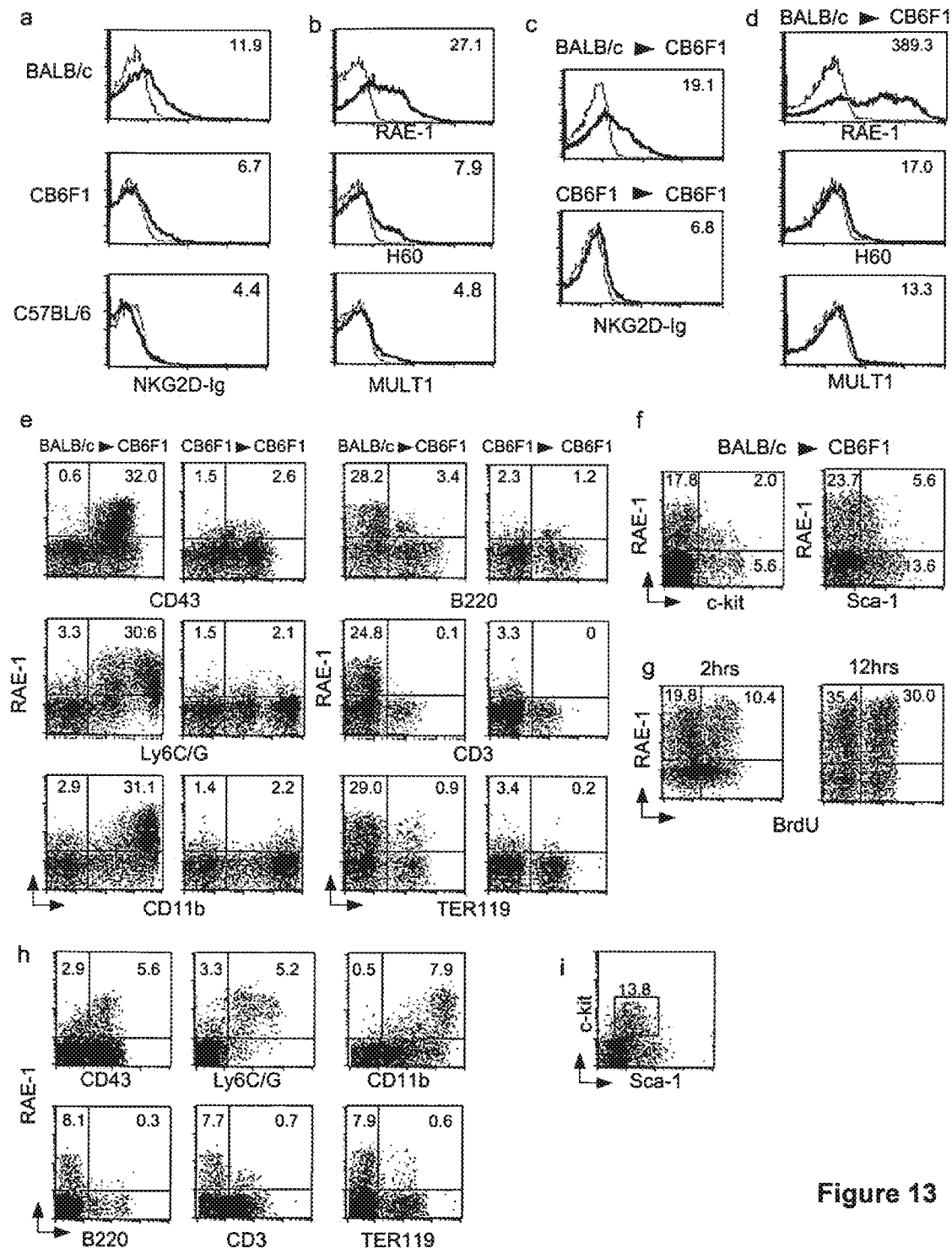
FIG. 13 shows that RAE-1 is expressed on B/c BM cells but not on B6 BM cells.

The genes encoding NKG2D ligands are polymorphic; BALB/c (B/c) mice have RAE-1α, β, and γ genes, whereas C57BL/6 (B6) mice possess RAE-1δ and ε genes (Cerwenka and Lanier, *Tissue Antigens,* 61:335-343, 2003). Similarly, B/c but not B6 mice express H60 (Malarkannan et al., *J Immunol,* 161:3501-3509, 1998). BM cells isolated from B/c, B6 and (BALB/c×C57BL/6) F1 (CB6F1) mice were analyzed to determine whether NKG2D ligands are expressed on BM cells. Cells were stained with a mouse NKG2D-IgG Fc fusion protein and analyzed by flow cytometry. Low levels of NKG2D ligands were detected on the surface of freshly isolated B/c BM cells, but not on B6 BM cells (FIG. 13*a*). In order to determine which NKG2D ligands were expressed, BM cells were stained with anti-pan RAE-1, anti-H60 and anti-MULT1 monoclonal antibodies (mAbs). RAE-1 and H60 were expressed at low levels on freshly isolated B/c BM cells, whereas MULT1 was not detected (FIG. 13*b*). By contrast, RAE-1 was not detected on freshly isolated splenocytes from B/c, B6 or CB6F1 mice.

Prior studies have established that NK cells in F1 recipients are able to reject parental bone marrow grafts (Kiessling et al., *Eur J Immunol,* 7:655-663, 1977; Lotzova et al., *Transplantation,* 35:490-494, 1983; Murphy et al., *J Exp Med,* 165, 1212-1217, 1987; and Murphy et al., *Eur J Immunol,* 20:1729-1734, 1990). The inventors contemplated that the B/c BM cells that repopulate the spleen in an irradiated CB6F1 recipient express NKG2D ligands. Thus during development of the present invention, the recipient CB6F1 mice were pre-treated with an anti-NK1.1 mAb to deplete the resident NK cells and thereby prevent rejection of the transplanted B/c BM cells. As a control, a group of irradiated CB6F1 mice were reconstituted with syngeneic CB6F1 BM cells. Seven days after grafting, the hematopoietic cells repopulating the spleens of the CB6F1 mice were isolated and analyzed for expression of NKG2D ligands. As shown in FIG. 13*c*, NKG2D ligands were detected on the hematopoietic cells isolated from the spleens of B/c BM→CB6F1 mice, but not on cells isolated from the spleens of CB6F1 BM→CB6F1 mice. The B/c hematopoietic cells reconstituting the spleens of the irradiated CB6F1 recipients predominantly expressed RAE-1, and not H60 or MULT1 (FIG. 13*d*).

In order to identify the population of hematopoietic cells that expressed RAE-1, cells isolated from the spleens of CB6F1 BM→CB6F1 and B/c BM→CB6F1 recipients were stained with mAbs against hematopoietic lineage markers. At day 7 post-transplantation, RAE-1 was detected on the majority of cells isolated from the spleens of CB6F1 BM→CB6F1 recipients. In contrast, RAE-1 was not detected on a substantial proportion of cells from the spleens of CB6F1 BM→CB6F1 recipients. Essentially all RAE-1-positive cells isolated from the B/c BM→CB6F1 recipients expressed CD43 (FIG. 13*e*). RAE-1 was also present on most cells expressing the granulocyte-associated Gr-1 (Ly-6C/G) protein and the myeloid cell-associated marker CD11b (Mac-1). Only a minor fraction of B220 (B cell-associated marker)-positive cells and Ter119 (an erythrocyte-associated marker)-positive cells expressed RAE-1, and RAE-1 was not detected on CD3$^+$ T cells (FIG. 13*e*). It is contemplated that the B cells and T cells detected in the spleens were residual radioresistant cells of host origin, because it is unlikely that T cells or B cells would have developed from the donor bone marrow cells in less than a week post-transplantation. RAE-1 was detected on a small subset of cells expressing c-kit and Sca-1, although most RAE-1-positive cells did not have these markers (FIG. 13*f*). The proliferation status of cells expressing RAE-1 in the B/c BM→CB6F1 recipients was evaluated by injecting BrdU into these mice at 2 hr and 12 hr before harvesting the spleen cells on day 7 post-transplantation. As shown in FIG. 13*g*, RAE-1 was readily detected on a large fraction (but not all) of the proliferating progenitor cells in the spleens of the transplant recipients.

In initial experiments, CB6F1 mice were transplanted with whole bone marrow isolated from B/c donors. In order to address whether RAE-1 is expressed on the progeny of hematopoietic stem cells (HSC), donor B/c mice were treated with 5-fluorouracil (5-FU) before bone marrow harvest to enrich for HSC, and bone marrow from 5-FU-treated donors was then transplanted into CB6F1 recipients that were pretreated with anti-NK1.1 mAb to deplete resident host NK cells. The bone marrow cells harvested from the 5-FU-treated donors did not express RAE-1. When cells in the spleens of B/c 5-FU BM→CB6F1 recipients were analyzed on day 8 post-transplantation, essentially all RAE-1-positive cells expressed Ly-6C/G, CD11b and CD43, but not CD3, Ter119, or B220. A small population of RAE-1-positive cells expressed low levels of c-kit and Sca-1, although a majority of the RAE-1-positive cells lacked both of these markers (FIG. 13*i*). These results indicated that the majority of proliferating B/c progenitor cells in the NK cell-depleted CB6F1 recipients expresses RAE-1.

Since development of the present invention, the expression of NKG2D ligands on proliferating human bone marrow cells has been reported (Nowbakht et al., *Blood*, published electronically on Jan. 18, 2005). Thus, the inventors contemplate that experiments described herein in mice, are also relevant to humans (and other mammals).

NKG2D is Involved in Hybrid Resistance

Figure 14:
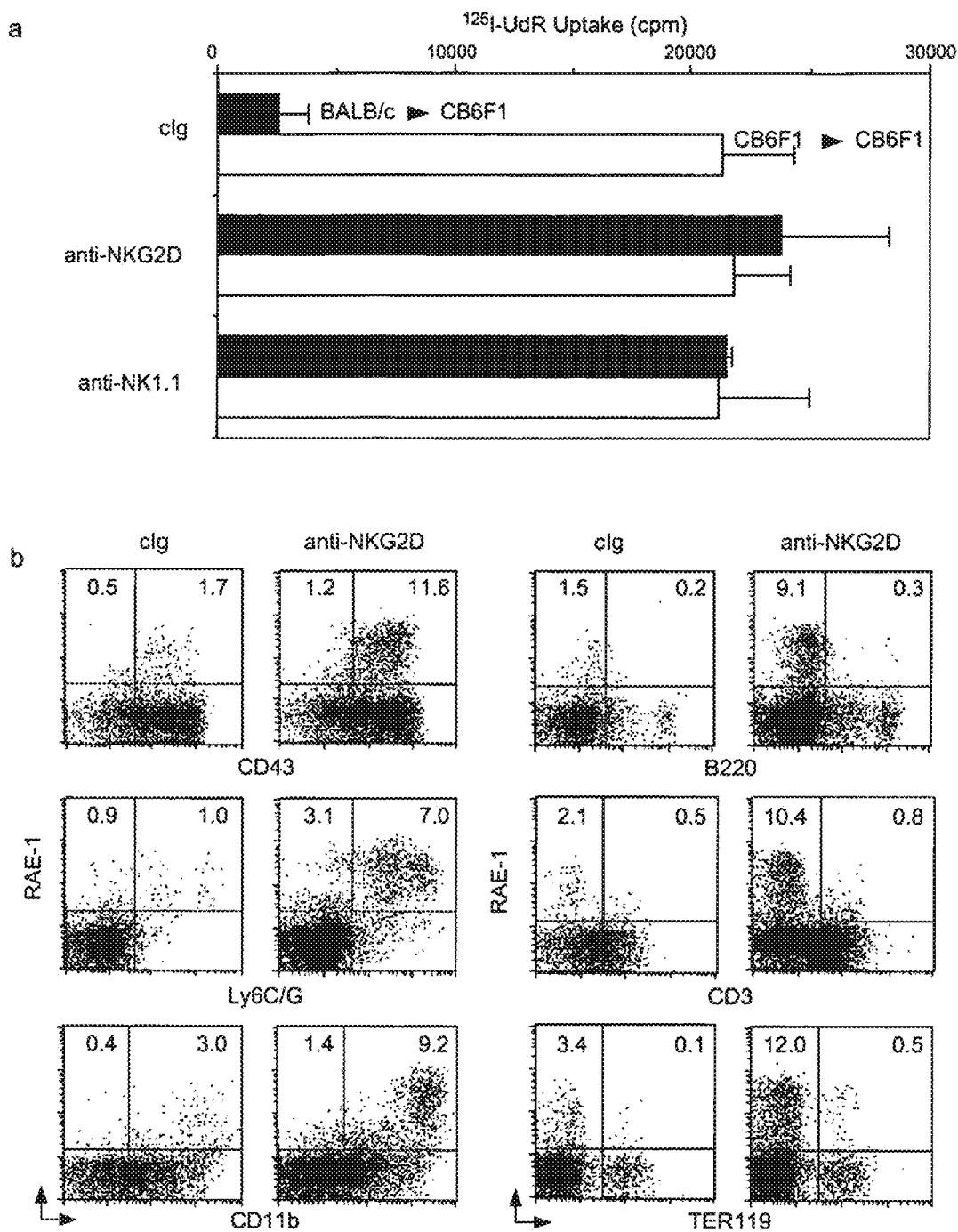
FIG. 14 (a): illustrates that Anti-NKG2D mAb blocks rejection of B/c BM in CB6F1 hybrid mice. Approximately 4×10⁶ BM cells were transferred into irradiated CB6F1 recipients. Recipient mice were injected with ¹²⁵IUdR on day 5, and spleens were harvested and counted on day 6. Black bars show ¹²⁵IUdR uptake of spleens in B/c BM→CB6F1 mice and white bars show uptake of radiolabel in CB6F1 BM→CB6F1 recipients. Mice were treated with the non-depleting, neutralizing anti-NKG2D mAb or the NK cell-depleting anti-NK1.1 mAb (200 µg/mouse on day −2), as indicated. Results are shown as the mean±S.D. cpm (5 mice per group). The experiment was performed twice with comparable results.

During development of the present invention, the finding that RAE-1 was expressed on the proliferating progenitor cells in the spleens of CB6F1 mice reconstituted with B/c bone marrow suggested to the inventors that NKG2D is involved in hybrid resistance. This was confirmed by transfer of B/c BM cells into irradiated CB6F1 mice pre-treated with a control antibody (cIg), a neutralizing, non-depleting anti-NKG2D mAb (CX5) (Ogasawara et al., *Immunity*, 20:757-767, 2004), or the NK cell-depleting anti-NK1.1 mAb (PK136). Hematopoietic cell reconstitution of recipient mice was evaluated by injecting $^{125}$IUdR twelve hours prior to harvesting spleens on day 7. cIg-treated mice rejected the B/c BM cells, and consistent with earlier reports (Lotzova et al., *Transplantation*, 35:490-494, 1983), depletion of NK cells in CB6F1 mice efficiently prevented rejection of the B/c bone marrow cells, which resulted in a substantial increase in incorporation of radiolabel in the spleens (FIG. 14*a*). The non-depleting, neutralizing anti-NKG2D mAb also dramatically increased incorporation of $^{125}$IUdR, comparable to the effects of depleting NK cells.

The ability of anti-NKG2D mAb treatment to prevent rejection of B/c bone marrow cells was confirmed by examining the cells repopulating the spleens on day 8 post-transplantation. As shown in FIG. 14*b*, RAE-1-positive cells predominately co-expressing CD43, Ly-6C/G, and CD11b were detected in the spleens of CB6F1 mice treated with anti-NKG2D mAb. In contrast, far fewer cells were recovered from the cIg-treated mice and very few of these cells expressed RAE-1. These data indicated that rejection of RAE-1-positive B/c BM cells in CB6F1 mice is efficiently prevented by either the depletion of NK cells or by blocking the NKG2D receptor.

NK Cells Eliminate Syngeneic BM Cells Expressing High Levels of RAE-1

Figure 15:
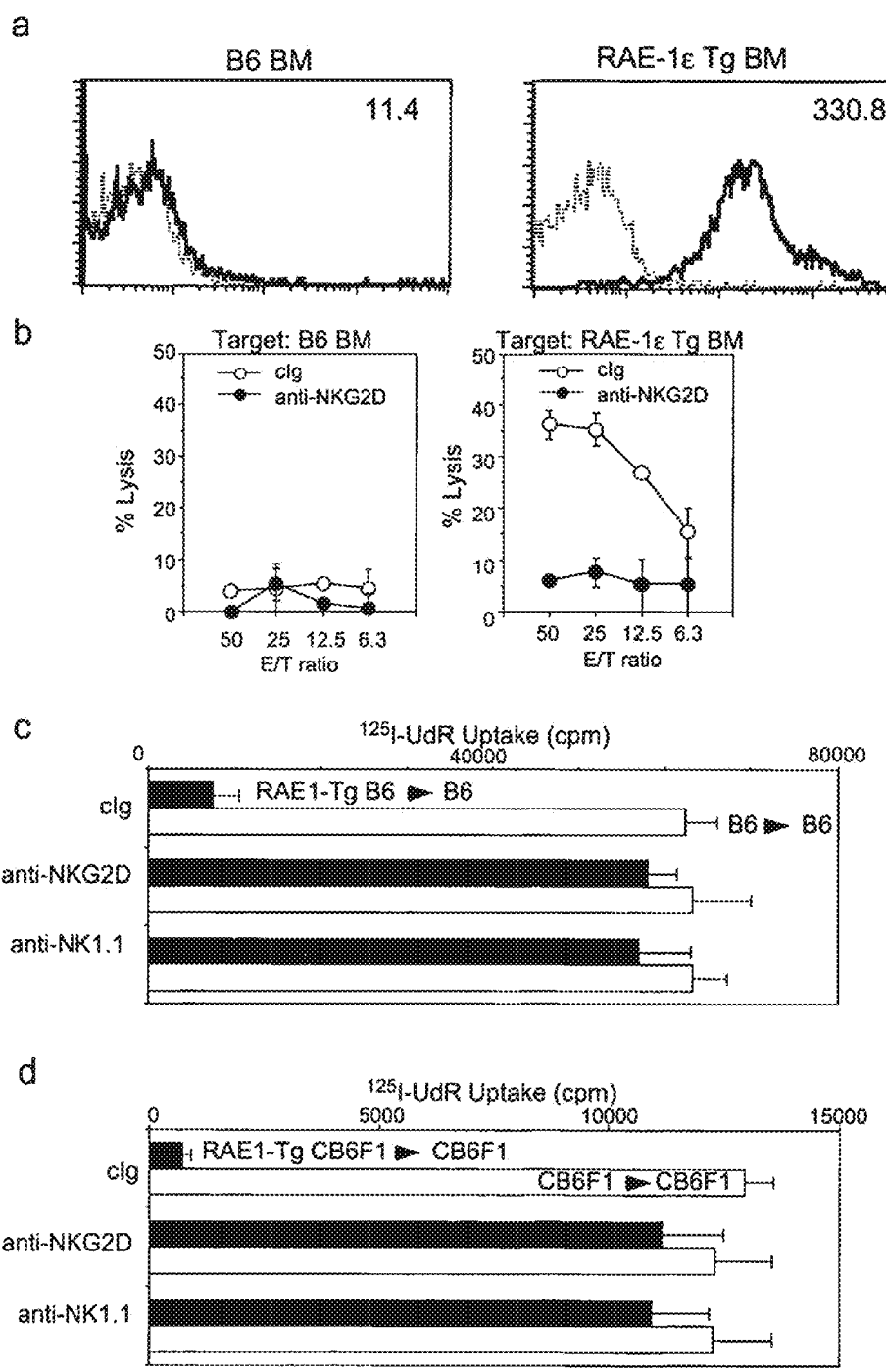
FIG. 15 illustrates the rejection of syngeneic BM cells expressing RAE-1.

The ability of anti-NKG2D mAb treatment to block rejection of parental bone marrow engraftment in F1 recipients raised the question of whether recognition of parental H-2 by the F1 NK cells is required for the NKG2D-dependent rejection or if NK cells can also reject syngeneic bone marrow cells provided that RAE-1 is expressed at sufficiently high levels. CB6F1 bone marrow cells repopulating syngeneic irradiated CB6F1 recipients (FIGS. 13*c, e*) and B6 bone marrow cells repopulating syngeneic irradiated B6 recipients expressed only very low levels of RAE-1 compared with B/c repopulating bone marrow cells (FIG. 13*d, e*). Therefore, in order to evaluate whether or not expression of RAE-1 on B6 or CB6F1 bone marrow cells would cause rejection of syngeneic bone marrow grafts, transgenic mice were generated that express RAE-1ε driven by a human β-actin promoter, resulting in RAE-1ε expression in all tissues. As shown in FIG. 15*a* the level of expression of RAE-1ε on freshly isolated bone marrow cells from B6 RAE-1ε transgenic mice, is similar to the levels of RAE-1 present on the repopulating B/c bone marrow cells (FIG. 13*d,e*).

Freshly isolated bone marrow cells from the RAE-1ε transgenic B6 mice were tested as targets for IL-2-activated syngeneic, non-transgenic NK cells in a standard in vitro cytotoxicity assay. As shown in FIG. 15*b*, activated NK cells killed freshly isolated RAE-1ε transgenic B6 bone marrow cells, but not RAE-1-negative non-transgenic B6 bone marrow cells. Cytotoxicity was blocked by an anti-NKG2D mAb, demonstrating that the killing is NKG2D-dependent. In accordance with the in vitro results, irradiated non-transgenic B6 mice rejected bone marrow cells from RAE-1ε transgenic B6 donors. Importantly, rejection was prevented in mice treated with the neutralizing anti-NKG2D mAb, but not in mice treated with a control Ig (FIG. 15*c*). Similar results were obtained when the RAE-1ε transgenic B6 were crossed with B/c mice and RAE-1ε transgenic CB6F1 bone marrow was grafted into non-transgenic CB6F1 recipients. The RAE-1ε transgenic CB6F1 bone marrow cells, unlike non-transgenic CB6F1 bone marrow cells (FIG. 13*c,e*), expressed high levels of RAE-1ε and were rejected by the syngeneic non-transgenic CB6F1 recipients (FIG. 15*d*). Rejection was prevented by administration of the neutralizing, non-depleting anti-NKG2D mAb or by depletion of NK cells with anti-NK1.1 mAb. Collectively, these findings demonstrate that B6 and CB6F1 NK cells can reject H-2 identical bone marrow cells, provided that the bone marrow cells express RAE-1.

DAP10 and DAP12 in NKG2D-Mediated BM Rejection

Figure 16:
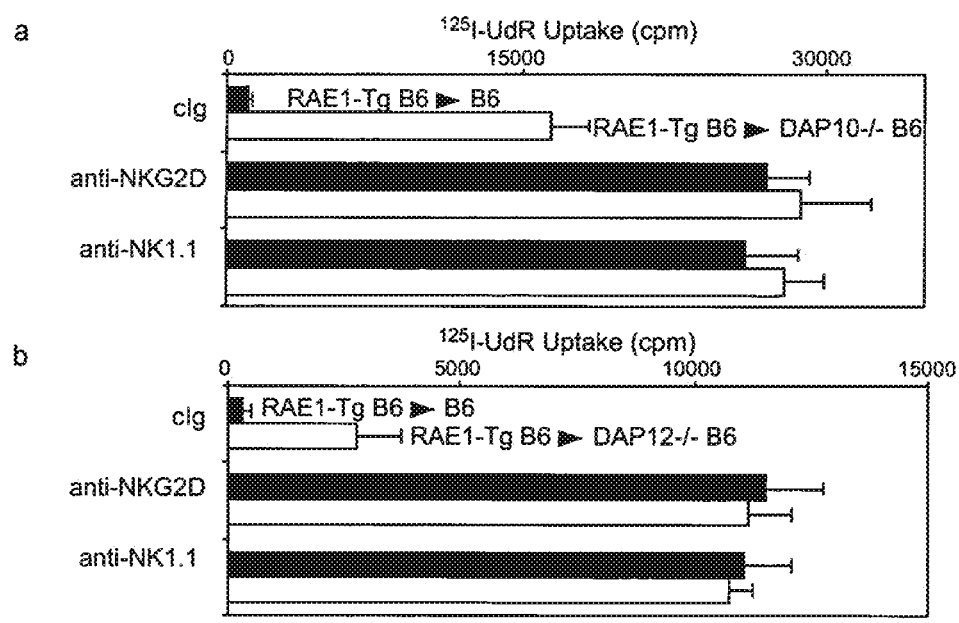

In mice, alternative RNA splicing of NKG2D transcripts generates two protein isoforms called NKG2D-S and NKG2D-L. NKG2D-L is expressed predominantly in resting NK cells and associates with the DAP10 adapter protein, whereas NKG2D-S is induced by activation of NK cells and associates with either DAP10 or DAP12 (Diefenbach et al., *Nat Immunol*, 3:1142-1149, 2002). Bone marrow cells from RAE-1ε transgenic B6 mice were transplanted into irradiated wild-type, DAP10−/−, and DAP12−/− C57BL/6 recipients, in order to determine whether DAP10 or DAP12 or both adapters are involved in NKG2D-mediated rejection. Mice were injected with $^{125}$IUdR on day 5 and spleens were harvested and counted on day 6. Compared with wild-type B6 mice, DAP10−/− B6 mice demonstrated a significant deficiency in rejecting the RAE-1ε transgenic B6 bone marrow graft (FIG. 16*a*). By contrast, DAP12−/− B6 recipients rejected the RAE-1ε transgenic B6 bone marrow more efficiently than the DAP10−/− B6 mice, although slightly less well than wild-type B6 mice (FIG. 16*b*). Wild-type, DAP10−/− and DAP12-/- B6 mice all failed to reject the RAE-1ε transgenic B6 bone marrow graft when treated with the depleting anti-NK1.1 mAb or with the non-depleting, neutralizing anti-NKG2D mAb. These results indicate a predominant role of DAP10, and a lesser role of DAP12, in NKG2D-dependent bone marrow rejection. Nonetheless, an understanding of the mechanism is not necessary in order to make and use the invention.

Defective Hybrid Resistance in RAE-1ε Transgenic Mice

Activation of NK cells from NOD mice induces expression of RAE-1, which results in ligand-dependent modulation of NKG2D on the NK cells (Ogasawara et al., *Immunity*, 18, 41-51, 2003). Analysis of the expression of NKG2D on the surface of NK cells from the RAE-1ε transgenic B6 mice revealed a reduced expression of NKG2D as compared to NK cells from wild-type mice (FIG. 17a). Although the amount of NKG2D on the RAE-1ε transgenic B6 was substantially diminished, the number of NK cells in the spleens and the expression of NK1.1, Ly-49D, Ly-49A, Ly-49C/I, Ly-49F/I/C/H, and Ly-49G2 on the NK cells were similar to wild-type NK cells. To examine whether NKG2D function is impaired in RAE-1ε transgenic NK cells, an antibody-redirected cytotoxicity assay was performed using cIg, anti-NKG2D mAb and anti-NK1.1 mAbs. Although NK1.1-dependent cytotoxic activity of RAE-1ε transgenic NK cells was identical to that of wild-type B6 NK cells, NKG2D-dependent cytotoxicity was impaired in RAE-1ε transgenic NK cells (FIG. 17b).

The RAE-1ε transgene is driven by a β-actin promoter in these transgenic mice, and therefore, the NK cells of these animals co-express both ligand and receptor. In order to determine whether wild-type (non-transgenic) NK cells are inactivated in vivo by constant exposure to NKG2D ligands, bone marrow chimeras were generated by transplanting wild-type Ly5.2 congenic B6 bone marrow into lethally-irradiated RAE-1ε B6 (Ly5.1) transgenic recipients. Three months after transplantation, the number of NK cells in the spleens and the expression of NK1.1 (FIG. 17c), Ly-49D, Ly-49A, Ly-49 C/I, Ly-49F/I/C/H and Ly-49G2 in Ly5.2 BM→RAE-1ε transgenic mice were similar to that in Ly5.2 BM→wild-type B6 mice. In contrast, NKG2D expression on NK cells was dramatically diminished in Ly-5.2 BM→RAE-1ε transgenic mice (FIG. 17c). Consistent with the diminished levels of NKG2D on the NK cells, NKG2D-dependent cytotoxic activity was impaired in Ly-5.2 BM→RAE-1ε transgenic mice, as determined by an in vitro antibody-redirected cytotoxicity assay (FIG. 17d). The inventors also investigated whether RAE-1ε transgenic B6 BM cells were rejected in Ly-5.2 B6 BM→RAE-1ε B6 transgenic recipients. As expected, NK cells in the wild-type Ly5.2 B6→wild-type B6 mice rejected RAE-1ε transgenic BM cells efficiently (FIG. 17e). In contrast, NK cells that developed in the Ly-5.2 B6 BM→RAE-1ε transgenic mice failed to reject RAE-1ε transgenic BM cells (FIG. 17). These findings indicated that NKG2D modulation of NK cells is caused by the interaction with irradiation-resistant recipient RAE-1 expressing cells in vivo, and that this results in impairment of NKG2D function in vivo. Nonetheless, an understanding of the mechanism is not necessary in order to make and use the invention.

To investigate whether F1 hybrid resistance is affected by the diminished levels of NKG2D on NK cells in the RAE-1ε transgenic B6 mice, the transgenic mice were crossed with B/c mice, and the RAE-1ε transgenic CBF1 mice were tested for their ability to reject parental B/c BM cells. Unlike wild-type CB6F1 mice, the RAE-1ε transgenic CB6F1 mice failed to reject B/c BM cells (FIG. 17f). Moreover, treatment with anti-NK1.1 mAb or anti-NKG2D mAb did not affect the $^{125}$IUdR incorporation of B/c BM cells in the RAE-1ε transgenic CB6F1 recipients. However, depleting NK cells or blocking NKG2D allowed engraftment of B/c bone marrow cells in wild-type CB6F1 recipients. Thus as demonstrated herein, NKG2D is implicated as an important component in F1 hybrid resistance.

EXAMPLE 7

NKG2D Blockage for the Prevention and Treatment of Rheumatoid Arthritis

This can be tested in a chronic animal model of arthritis where NKG2D can be demonstrated to be present at the site of inflammation. An example of such a model is the chronic collagen induced arthritis (Malfait et al., *Arthritis and Rheumatism* 44:1215-1224, 2001).

Recently, CD4+CD28– T cells in the peripheral blood and synovial tissues of human rheumatoid arthritis patients were found to express NKG2D, whereas inflamed synoviocytes were found to aberrantly express the MIC ligands of NKG2D (Groh et al., *Proc Natl Acad Sci USA*, 100:9452-9457, 2003). Thus, the inventors contemplate that the compositions and methods for blocking NKG2D described herein are also suitable for prevention and treatment of rheumatoid arthritis. The following experiments are performed to test the effect of NKG2D blockade on development of rheumatoid arthritis (RA) in an animal model system, the DBA/1 mouse.

Briefly, collagen type II (CII)-induced arthritis (CIA) is induced in 6- to 7-week-old male DBA/1 mice by intradermal tail base injection of 100 μg bovine collagen II supplemented with 2.0 mg/ml *Mycobacterium tuberculosis* H37RA emulsified in complete Freund's adjuvant, as described (Seo et al., *Nat Med*, 10:1088-1094, 2004). Joint inflammation is scored from 1 to 4, with a maximum score of 16 per mouse. The clinical severity of arthritis is graded as follows: 0, normal; 1, slight swelling and/or erythema; 2, substantial edematous swelling; 3, substantial edematous swelling plus light joint rigidity; or 4, laxity (See, e.g., Williams et al., *Proc Natl Acad Sci USA*, 89:9784-9788, 1992). Each limb is graded, allowing a maximum clinical score of 16 for each animal. Swelling of hind paws is measured with a pair of calipers.

Mice are injected with 200 μg of an anti-NKG2D mAb or a control isotype-matched mAb IP, on days 0, 2, 4, 6 and 8 or days 0, 3, 7 and 10 after immunization. The inventors contemplate that control IgG treatment results in development of severe arthritis beginning approximately 28 d after immunization (e.g., severity greater than 10; incidence greater than 80%, and paw thickness greater than 3.5 mm). In contrast, anti-NKG2D mAb treatment is expected to result in suppression of disease, which manifests as a decrease in arthritis severity, and incidence, as well as a reduced paw thickness and reduced joint histopathology relative to the control mAb-treated animals (e.g., severity less than 10, preferably less than 5 and most preferably less than 2; incidence less than 80%, preferably less than 50%, and most preferably less than 20%; and paw thickness less than 3.5 mm, preferably less than 3.0 mm, and most preferably less than 2.5 mm).

To treat established CIA, mice are injected on days 28, 30, 32, 34 and 36 or days 28, 31, 35 and 38 after immunization. The mice are then divided into two groups with equal mean arthritis scores on day 28 after immunization, and treated with control mAb, or anti-NKG2D mAb on days 28, 30, 32, 34 and 36 after immunization. It is contemplated that arthritis is reversed only in the anti-NKG2D mAb-treated group (e.g., reduction in disease severity, incidence, paw thickness and joint histopathology). Moreover, the inventors contemplate that anti-NKG2D mAb treatment will result in a reduction in numbers of NKG2D-expressing cells present in the joints of arthritic subjects, as well as a reduction in levels of inflammatory cytokines (e.g., TNF-α, IL-15, etc.) in the synovial fluid.

EXAMPLE 8

NKG2D Blockage for the Prevention and Treatment of Celiac Disease

MIC is strongly expressed at the gut epithelial surface in Celiac disease (CD) patients, which in turn co-activated intraepithelial T lymphocytes (IEL) via NKG2D, leading to cytolysis of epithelial cell targets (Meresse et al., *Immunity*, 21:357-366, 2004; and Hue et al., *Immunity*, 21:367-377, 2004). The inventors contemplate that the compositions and methods for blocking NKG2D described herein are also suitable for prevention and treatment of Celiac disease. The effect of NKG2D blockade on development of inflammatory bowel disease (IBD) will be tested in an suitable small animal model, such as, e.g., either one of the following two mouse models of colitis: TNB induced (Chin et al., *Digestive Diseases and Sciences* 39:513-525, 1994) or T-cell transferred model (Powrie et al., *Int Immunol* 5:1461 et seq., 1993) in SCID mice.

EXAMPLE 9

NKG2D Blockage for the Prevention and Treatment of Viral Hepatitis

The following experiments were performed to test the effect of NKG2D blockade on development of acute hepatitis in murine models of hepatitis B virus (HBV) infection (Baron et al., *Immunity*, 16:583-594, 2002, herein incorporated by reference).

Mice and Disease Model.

HBV-Env: mouse lineage 107-5D (official designation Tg[Alb-1.HBV] Bri66; inbred B10.D2, H-2$^d$) (Chisari et al., *Proc Natl Acad Sci USA*, 84:6909-6913, 1987). HBV-Replication: lineage 1.3.46 (official designation, Tg[HBV 1.3 genome] chi46) (Guidotti et al., *J Virol*, 69:6158-6169, 1995). Both strains were crossed to recombinase-activating gene-1 (RAG-1) knock-out (KO) animals. The HBV-Env transgenic mice contain the entire HBV envelope coding region (subtype ayw) under the constitutive transcriptional control of the mouse albumin promoter. These mice express the HBV small, middle and large envelope proteins in their hepatocytes. The HBV-Replication mice contain a terminally redundant HBV DNA construct (Guidotti et al, supra, 1995). These mice have high-level viral replication in their hepatocytes and in proximal convoluted tubules of their kidneys. The replication level seen in these animals are comparable to that observed in the infected livers of patients with chronic persistent HBV hepatitis, but the mice show no evidence of cytopathology (Guidotti et al, supra, 1995). Various HBV-Env$^+$ Rag$^{-/-}$ and HBV-Replication Rag$^{-/-}$ mice (8-10 weeks of age) were intravenously injected with donor splenocytes from wild type B10.D2 male mice of 6-10 weeks of age (Jackson Laboratory, Bar Harbor, Me.). Mice were bled by tail vein at described intervals and serum was collected. Other mice were sacrificed at the indicated time points and livers were collected for histological examination. All mice were kept in a pathogen-free facility at UCSF.

Alanine Aminotransferase (ALT) Assay.

Serum alanine aminotransferase (ALT) was measured by the standard photometric method using a COBAS MIRA plus auto-analyzer.

Isolation of Intrahepatic Immune Cells.

Mice livers were perfused via the thoracic portion of the inferior vein cava with digestion media (RPMI medium, containing 0.2 mg/mL collagenase and 0.02 mg/mL DNAse and 5% FCS) for 5 minutes. The livers were then homogeneized by forcing them through a metal strainer. The cell preparation was centrifuged to remove hepatocytes (30 RCF for 3 min), and the remaining cells were centrifuged in a Percoll gradient to collect the immune cells in the interface.

Isolation of Hepatocytes.

Livers were perfused via the thoracic portion of the inferior vein cava with a commercial liver perfusion medium (GIBCO, cat no. 17701-038) for 5 minutes, followed by a digestion media (DMEM Low Glucose 50%/F-12 50% mix, with NEAA, Medium, containing 0.12-0.2 mg/mL collagenase) for 8 minutes. Livers were cut in very small pieces and filtered trough a 70 μm nylon cell strainer. The filtered solution was centrifuged at 30 RCF for 3 minutes and the cells were counted using trypan blue.

Flow Cytometer.

Intrahepatic immune cells were stained first with Fc-block 1:5 and then with PE-labeled anti-NKG2D, anti-TCRβ biotin and APC-labeled anti-NK1.1 antibodies and their isotype controls. Streptavidin-Qdot605 was used as the secondary antibody for anti-TCRβ biotin antibody and its isotype control. Hepatocytes were stained with purified anti-pan-RAE-1, anti-Mult-1 and anti-ratIgG2a antibodies, and gated on the DAPI negative population. Goat anti-rat PE was used as the secondary antibody. FACS analysis was done on a LSR II, using different settings for FIG. 18D to get the brightest TCRβ surface staining in activated NK T cells. Analysis of data was done using Flowjo software.

Quantitative PCR.

Quantitative (real-time) PCR was carried out using the ABI 7300 (Applied Biosystems) according to the manufacture's instructions. Specific probes: FAM-CATCAGTGAC AGT-TACTTCT TCACCTTCTA CACA (pan-RAE-1 set forth as SEQ ID NO:14) and CAAACTTTGC TTTCCCTGGT TAAGCAGTAC AGC-FAM-TAMRA (HPRT set forth as SEQ ID NO:15). Primers: pan-RAE-1 sense CTAGTGCCAC CTGGGAATTC A (SEQ ID NO:6); pan-RAE-1 antisense CATCATTAGC TGATCTCCAG CTCA (SEQ ID NO:7); HPRT sense AGCTTGCAAC CTTAACCATT TTG (SEQ ID NO:16), and HPRT antisense TGGAAAGAAT GTCT-TGATTG TTGAA (SEQ ID NO:17). Total RNA was treated with Dnase I. The cycling conditions for real-time PCR were: 2 min at 50° C., 10 min at 95° C., followed by 40 cycles of 95° C. for 15 s and 1 min at 60° C.

In Vivo Antibody Treatment.

Anti-mouse NKG2D mAb, clone CX5 (Rat IgG1), generated as described (Ogasawara et al., supra 2003), recognizes the NKG2D extracellular domain and efficiently blocks the binding of NKG2D to its ligands. Two hundred μg of CX5 or Rat IgG (Sigma, ST. Louis, Mo.) per mouse were injected into the peritoneal cavity one day before and four days after the adoptive transfer of syngeneic naïve splenocytes.

ELISpot Assay.

Intra-hepatic immune cells were eluted from various mice at day 3 and/or 4 post adoptive transfer (AT). Cells were counted and immediately plated in an anti-cytokine pre-coated 96-well microplate (BD, ELISpot mouse IFN-gamma and IL-4 kits). Eight serial 2 or 3-fold dilutions were tested in duplicate, per condition. Spots were counted automatically using an AID ELISpot Reader.

Histology.

Liver pieces, placed in 10% formalin in tissue cassettes, were embedded in paraffin and stained with hematoxylin and eosin according to a standard protocol.

Statistical Analysis.

Two-sample Student's t test was performed and P<0.05 was considered significant.

The Majority of Interferon Gamma-Secreting Cells Present in the Livers of Mice with Acute Hepatitis are NK and NK T Cells.

Although activation of non-classical NK T cells is necessary for development of acute hepatitis, NK cells alone do not initiate anti-hepatic immune responses. (Baron et al, supra 2002). As described herein, the cellular profile of IFN-gamma producing cells present in the livers of HBV-Env$^+$ Rag$^{-/-}$ mice 3 days after the adoptive transfer of syngeneic splenocytes has now been determined. Approximately 41% and 43% of NK and NK T cells in HBV-Env$^+$ Rag$^{-/-}$ mice, respectively, secrete IFN-gamma, in contrast to 19% and 29% of NK and NK T cells, respectively, in HBV-Env$^-$ Rag$^{-/-}$ mice. In both strains, the production of IFN-gamma by intra-hepatic T cells; and by NK1.1 negative, TCR negative intra-hepatic immune cells was undetectable. Thus, IFN-gamma production is accounted for by NK and NKT cells, despite the fact that NK cells alone are insufficient for the development of hepatitis.

NKG2D Expression is Increased on Intra-Hepatic Immune Cells and Peripheral Blood Cells from HBV$^+$ Rag$^{-/-}$ Transgenic Mice with Acute Hepatitis.

Figure 18D:
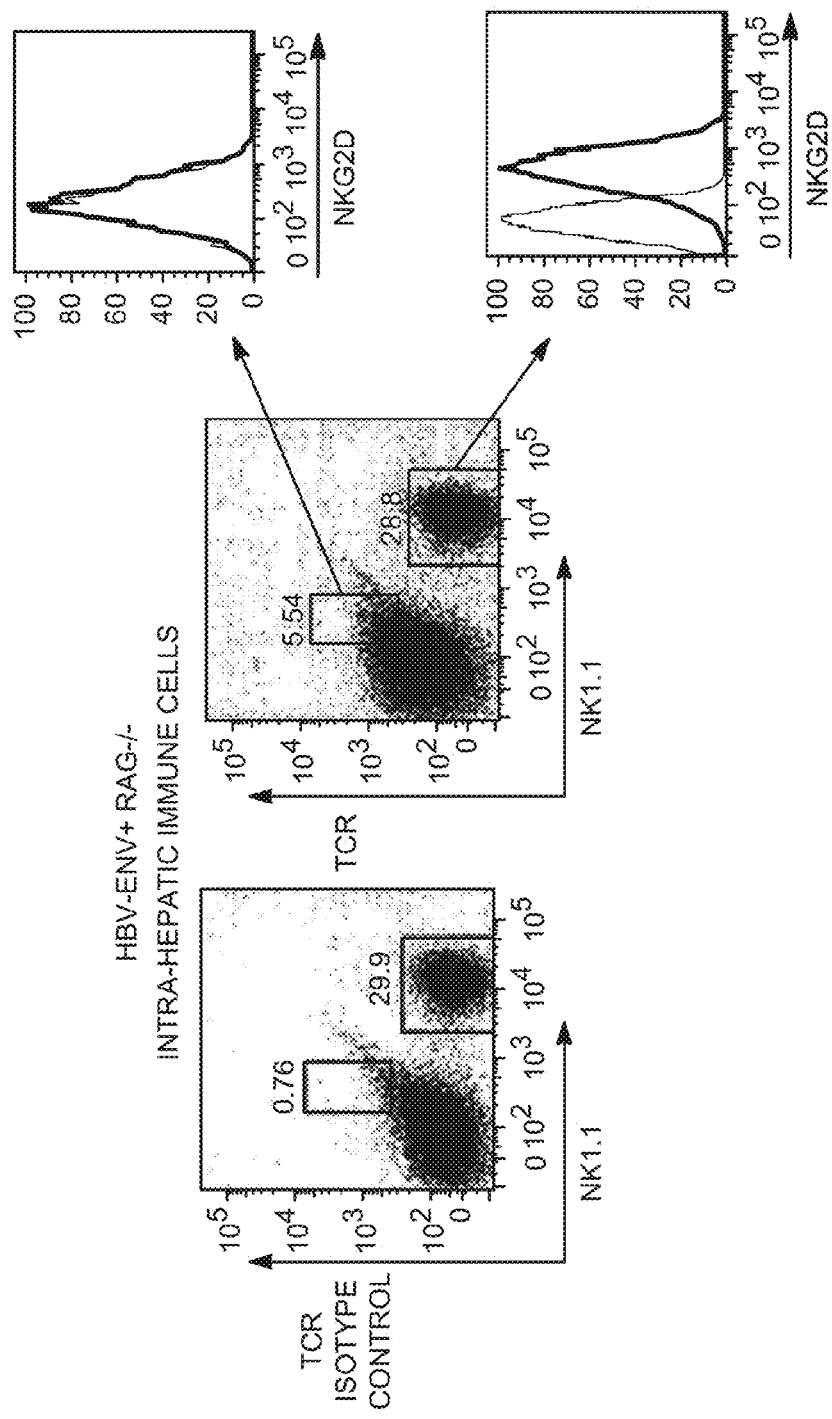
FIG. 18 illustrates that NKG2D is up-regulated during acute hepatitis. NKG2D expression levels are shown on the surface of NK1.1 positive cells from HBV-Env$^+$ Rag$^{-/-}$ (black line) and HBV-Env$^-$ Rag$^{-/-}$ (dashed line) mice before (FIG. 18A), and 3 days after (FIG. 18C), adoptive transfer of syngeneic naïve splenocytes. Hepatic necrosis in these animals was assessed by the measurement of alanine aminotransferase (ALT) in the serum of HBV-Env$^-$ Rag$^{-/-}$ mice (open circles) or HBV-Env$^+$ Rag$^{-/-}$ (closed circles) (FIG. 18B). Surface expression of NKG2D in intra-hepatic NK (FIG. 18D, left histogram) and NK T cells (FIG. 18D, right histogram) from HBV-Env$^+$ Rag$^{-/-}$ mice 3 days after adoptive transfer. Tinted histograms depict staining using an isotype control (rat IgG1).

NK and NK T cells are central players in the clearance of virus-infected or tumor cells, and NKG2D is an activating and/or co-stimulatory receptor expressed on all NK cells, and on most NK T cells. The level of NKG2D expressed on the surface of NK1.1 positive cells in the liver and in the blood of HBV-Env$^+$ Rag$^{-/-}$ and HBV-Env$^-$ Rag$^{-/-}$ mice was analyzed. NK1.1+ cells from both mice expressed similar amounts of NKG2D (FIG. 18A). However, the surface levels of NKG2D vary according to the activation state of the NK or NK T cell. Thus, the expression of NKG2D was assessed during the acute immune response against HBV-antigen positive hepatocytes. Syngeneic splenocytes were adoptively transferred into HBV-Env$^+$ Rag$^{-/-}$ and HBV-Env$^-$ Rag$^{-/-}$ mice. The development of acute hepatitis was determined by measuring the release of alanine amino transferase (ALT) into the blood (FIG. 18B). At the peak of the immune response, around day 3, the expression of NKG2D in cells eluted from the livers of HBV-Env$^+$ Rag$^{-/-}$ and HBV-Env$^-$ Rag$^{-/-}$ was determined by FACS. NK and NK T cells from HBV-Env$^+$ Rag$^{-/-}$ mice were found to express higher levels of NKG2D than the same populations eluted from HBV-Env$^-$ Rag$^{-/-}$ mice (FIG. 18C). Circulating NK cells also expressed higher levels of NKG2D (FIG. 18D) in HBV-Env$^+$ Rag$^{-/-}$ mice. This indicates that NKG2D plays a role in the activation of NK and NK T cells in the HBV-Env$^+$ Rag$^{-/-}$ mice, and consequently in the development of acute hepatic injury.

Elevated RAE-1 Surface Expression Specifically on HBV-Env$^+$ Hepatocytes.

Figure 19A:
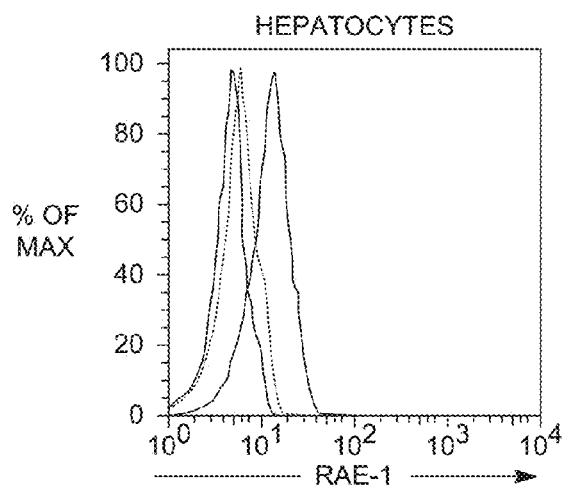
FIG. 19 illustrates that RAE-1 is up-regulated exclusively on HBV-Env-expressing hepatocytes, before adoptive transfer of syngeneic naïve splenocytes. Surface expression of RAE-1 (FIG. 19A) and Mult-1 (FIG. 19C) on hepatocytes from HBV-Env$^+$ Rag$^{-/-}$ (black line) and HBV-Env$^-$ Rag$^{-/-}$ (dashed line) mice is shown. The fold induction of RAE-1 mRNA expression in hepatocytes from HBV-Env$^+$ Rag$^{-/-}$ (black bar) and HBV-Env$^-$ Rag$^{-/-}$ (open bar) mice is shown in comparison with HPRT expression (FIG. 19B). Tinted histograms depict staining using an isotype control (Rat IgG2a).
Figure 19B:
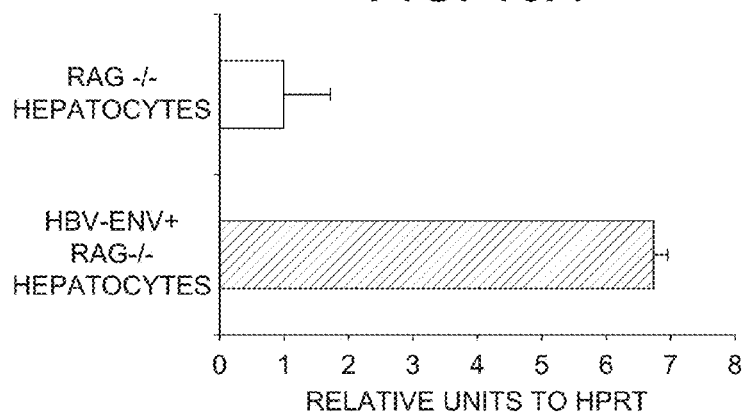
Figure 19C:
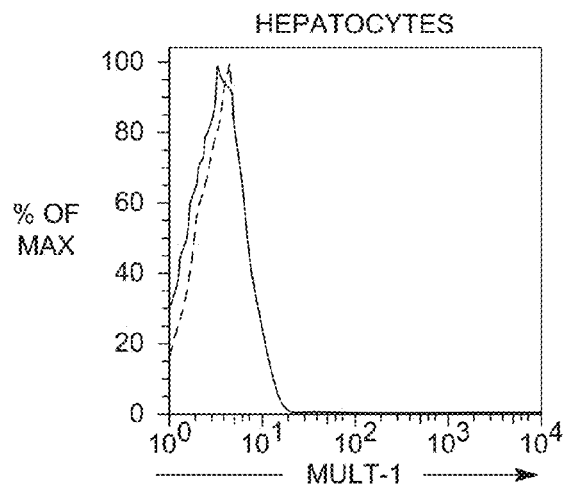

Circulating and resident NK and NKT cells expressed higher amounts of NKG2D during development of acute hepatitis. In mice, NKG2D recognizes the RAE-1 family and Mult-1 family of genes that are up-regulated in virally infected cells or transformed, malignant, cells. The expression of NKG2D ligands in perfused hepatocytes and intra-hepatic immune cells of HBV-Env$^+$ Rag$^{-/-}$ and HBV-Env$^-$ Rag$^{-/-}$ mice was assessed. An increased level of expression of RAE-1 was found on the surface of HBV$^+$ hepatocytes, as compared to HBV$^-$ hepatocytes. This increase was only detected in cells expressing the HBV-Env protein since intra-hepatic immune cells from the livers of HBV-Env$^+$ Rag$^{-/-}$ and HBV-Env$^-$ Rag$^{-/-}$ mice showed similar lower levels of surface RAE-1 (FIG. 19A). In contrast, Mult-1 surface expression was not detected in any of the cells analyzed (FIG. 19C). This indicates that expression of HBV antigens in hepatocytes induces the expression of RAE-1 family of proteins on its surface. Thus, as described herein for the first time an HBV-expressing hepatocyte (reminiscent of an HBV infected liver) is capable of alerting the host, innate-like, immune system, through interactions with the activating NKG2D receptor expressed in NK and NKT cells.

Blocking of RAE-1 Recognition by NKG2D In Vivo Prevents Acute Hepatitis in Our Transgenic Mouse Model of Primary HBV Infection.

Liver necrosis in HBV-Env$^+$ Rag$^{-/-}$ transgenic mice is caused by the acute immune response of the adoptively transferred syngeneic naïve non-classical NK T cells against HBV antigens expressed by the hepatocytes (Baron et al. supra 2002). However, the mechanism of NK T cell activation was not known prior to development of the present invention. Infection by CMV results in increased expression of NKG2D ligands, and activation of this signaling pathway is necessary for cytotoxicity and cytokine production (Groh et al, supra 2001). Likewise, RAE-1 was up-regulated exclusively in hepatocytes that also expressed HBV antigens. The effects of neutralization of the NKG2D receptor during the onset of the acute hepatitis B was tested using a blocking monoclonal antibody (CX5) (Ogasawara et al., supra 2003). Briefly, HBV-Env$^+$ Rag$^{-/-}$ mice were treated with 200 µg of CX5 mAb or an isotype control (rat IgG1) the day prior to and four days after the adoptive transfer of syngeneic naive splenocytes. As shown in FIG. 20A, blocking the NKG2D receptor prevented liver injury in all HBV-Env$^+$ Rag$^{-/-}$ mice, whereas the rat IgG isotype control had no effect and all mice showed signs of massive acute hepatitis, as revealed by the serum ALT values at days three and four after the adoptive transfer. In addition, all mice treated with rat IgG had yellow serum at day 6 after adoptive transfer, which correlates with increased levels of serum total bilirubin. In contrast, none of the HBV-Env$^+$ mice treated with anti-NKG2D mAb showed elevated amounts of serum bilirubin. Histological analyses also showed that only the mice treated with rat IgG developed a severe hepatitis, pathologically characterized by lobular inflammation, hepatocellular damage, and portal inflammation and necrotic hepatocytes at day 4 after adoptive transfer (FIG. 20B). These histological abnormalities were absent in all mice treated with anti-NKG2D mAb (FIG. 20B), at the same time point. These results demonstrate a fundamental role played by NKG2D in the acute immune response against HBV-expressing hepatocytes and on development of necrotic hepatic injuries. Thus, an increased expression of RAE-1 by the "infected" cell is contemplated to act as an activation signal thereby alerting the immune system.

Intra-Hepatic Cytokine Production by Innate Effector Cells in Response to HBV is Greatly Diminished by Blocking NKG2D In Vivo.

The cytokine profile of anti-NKG2D and rat IgG treated mice was also investigated. The number of IFN-gamma (FIG. 20C), TNF-alpha and IL-4 (FIG. 20D) producing intra-hepatic immune cells was quantified by Elispot at day 3 and 4 after adoptive transfer of syngeneic wild type splenocytes. Three days after the adoptive transfer, the number of IFN-gamma, TNF-alpha and IL-4 producing cells increased by eight, ten and seven fold, respectively, in mice that received rat IgG as compared to anti-NKG2D mAb-treated mice. The number of cytokine-producing cells in mice treated with anti-NKG2D was very low and of the same order of magnitude as HBV-Env$^+$ Rag$^{-/-}$ CD1d$^{-/-}$ mice that received syngeneic wild type splenocytes (Baron et al., supra 2002). Four days after the adoptive transfer, the difference in cytokine production by intrahepatic immune cells of anti-NKG2D mAb or rat IgG treated mice is still evident. Thus blocking NKG2D also severely impaired the production of cytokines by intra-hepatic immune cells, in mice expressing HBV antigens.

Up-Regulation of NKG2D on Intra-Hepatic NK1.1 Positive Immune Cells from HBV-Replication$^+$ Rag$^{-/-}$ Transgenic Mice During Acute Hepatitis.

Figure 21:
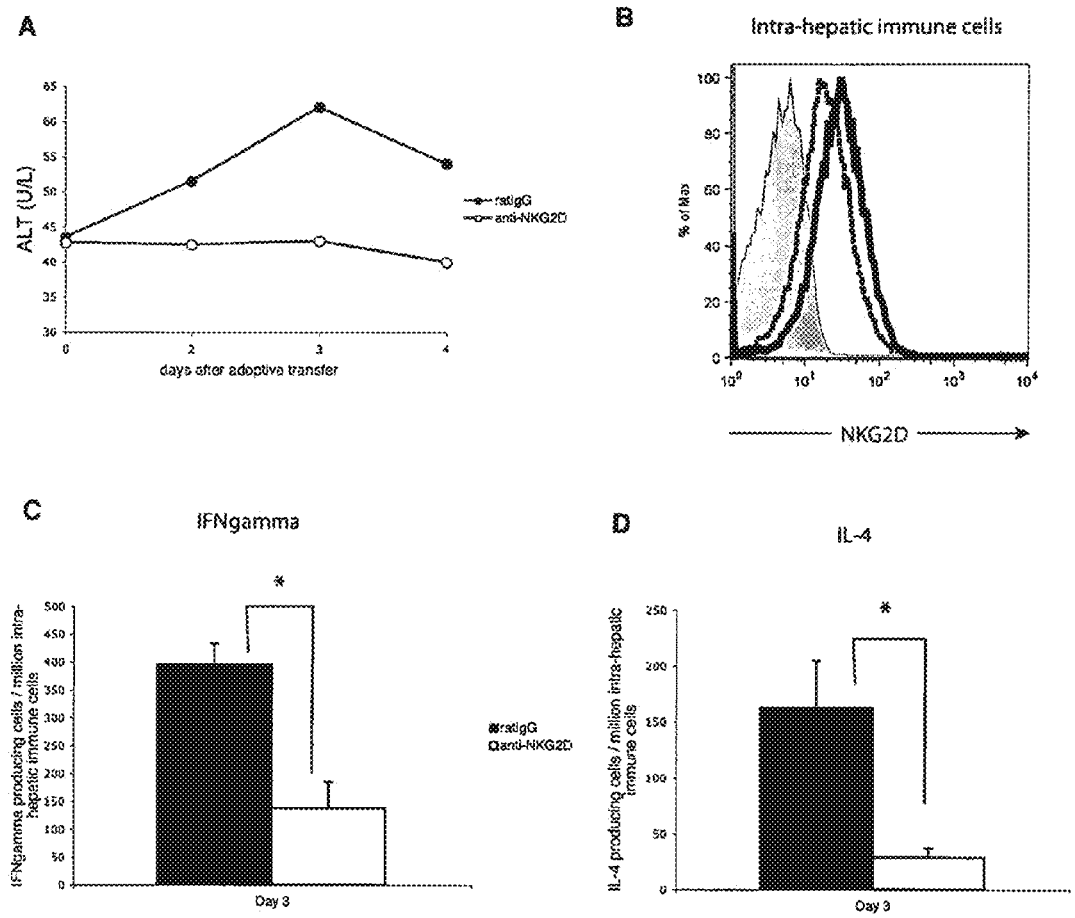
FIG. 21 illustrates the role of NKG2D in HBV-Replication Rag$^{-/-}$ mice during acute hepatitis.

HBV-Replication Rag$^{-/-}$ mice, which display intra-hepatic HBV replication by expressing all viral proteins at their proper stoichiometry were also examined. The amounts of NKG2D expressed on the surface of NK1.1 positive intra-hepatic immune cells from HBV-Replication$^+$ Rag$^{-/-}$ were determined 2 and 3 days after adoptive transfer of syngeneic splenocytes. As shown in FIG. 21B, increased expression of NKG2D in NK1.1+ cells of HBV-Replication$^+$ Rag$^{-/-}$ mice was observed. In addition as was observed in the HBV-Env$^+$ Rag$^{-/-}$ mice, HBV-Replication$^+$ Rag treated with anti-NKG2D mAb had reduced levels of liver damage, and IFN-gamma and IL-4 producing hepatic immune cell infiltrates as compared to rat IgG treated controls (FIGS. 21A, 21C and 21D).

Liver Pathogens.

Hepatitis B virus (HBV) and hepatitis C virus (HCV) are noncytopathic, hepatotropic members of the hepadnavirus (HBV) and flavivirus (HCV) families that cause acute and chronic necroinflammatory liver disease and hepatocellular carcinoma (HCC) (Chisari and Ferrari, *Annu Rev Immunol*, 13:29-60, 1995; Ferrari et al., *B J Hepatol*, 39(S1):S36-S43, 2003; and Lauer and Walker, *N Engl J Med*, 345: 41-52, 2001). It is widely believed that the outcome of both infections and the pathogenesis of the associated liver diseases are determined by host-virus interactions mediated by the immune response. Thus, a role for NKG2D and its ligands in acute and chronic hepatitis C viral infection is contemplated. Accordingly, the present invention also provides methods for treating or preventing viral hepatitis associated with acute and/or chronic HCV infection. Also contemplated are methods for treating or preventing hepatitis associated with other microbial infections.

Adjunct Therapies.

In some preferred embodiments of the present invention, NKG2D blocking antibodies are used in combination with other antiviral therapies, including but not limited to nucleotide and nucleoside analogues (Epivir, Adefovir dipivoxil, Tenofevir, and Entecovir Baraclude-lamivudine) and other immune modulatory drugs (interferon-alpha-2b and pegylated interferon-alpha-2a).

EXAMPLE 10

NKG2D Blockage for the Prevention and Treatment of Cardiac Allograft Rejection

The following experiments were performed to test the effect of NKG2D blockade on development of solid organ rejection in an animal model of cardiac allograft transplantation (McNerney et al., *Am J Transplant*, 6:505-513, 2006, herein incorporated by reference).

Heart and Skin Transplantation.

Figure 22:
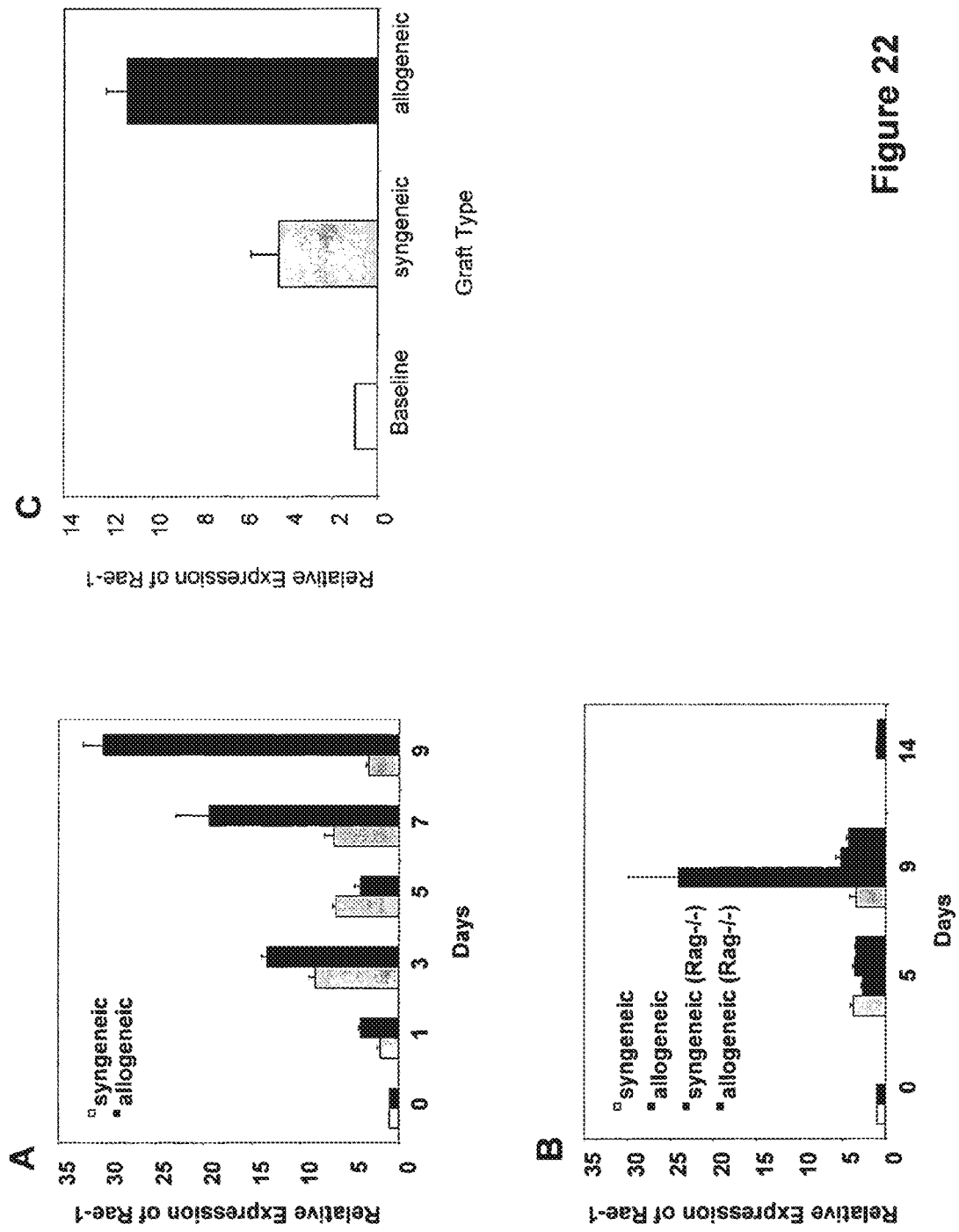
FIG. 22 illustrates that Rae-1 (NKG2D-ligand) is expressed in transplants, as analyzed by RT-PCR. Representative data shown are the means of normalized Rae-1 expression±SD done in triplicates.

To assess the induction of NKG2D ligands after transplantation, Balb/C and C57B1/6 skin or heart grafts were transplanted onto C57BL/6 recipients and tissues were harvested at various time points. Total RNA was isolated and evaluated for expression of NKG2D ligands by using real-time quantitative PCR. The expression of NKG2D ligands (RAE-1) was upregulated in both syngeneic and allogeneic transplants at early time points. Expression levels returned to baseline in the syngeneic group, whereas the ligands were vastly upregulated by day 7 in the allogeneic group (FIG. 22A), likely due to additional injury caused by alloreactive T cells. This late upregulation was strictly dependent on the adaptive immune response as NKG2D ligand levels returned to baseline in T cell-deficient hosts (FIG. 22B). Rae-1 expression was also upregulated on cardiac allografts at day 7, with higher levels seen in the allogeneic grafts compared to syngeneic grafts (FIG. 22C).

Figure 23:
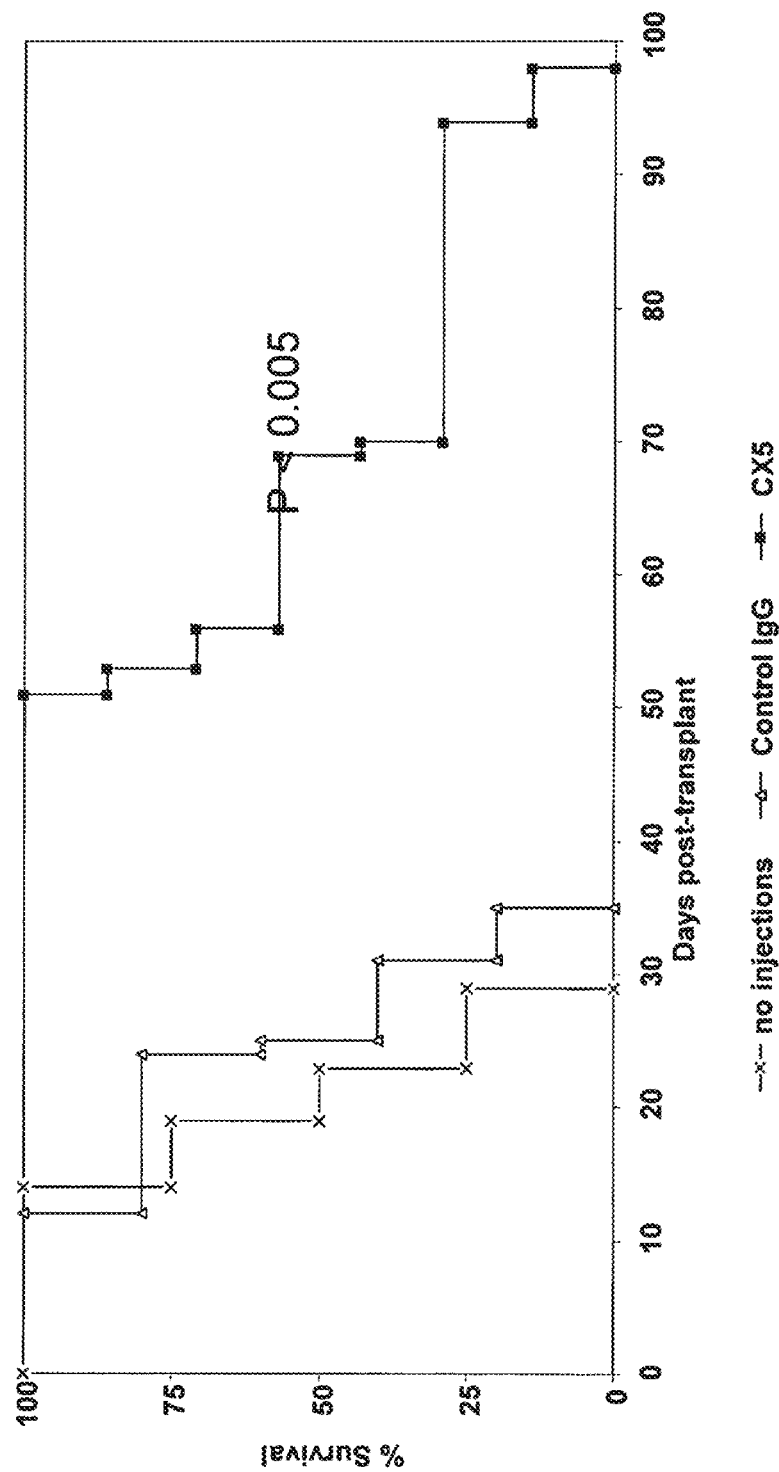
FIG. 23 illustrates that treatment in vivo with anti-NKG2D mAb (CX5) prolongs cardiac allograft survival in CD28−/− mice. Kaplan-Meier curve demonstrating distribution of survival in days for CD28−/− mice injected with CX5 (n=7) compared with control groups with no treatment (n=4) or injected with control rat IgG (n=5).

To determine the role of NKG2D in allograft rejection, the CD28 deficient heart transplant rejection model (Balb/C heart into B6 CD28 KO host) was employed. In this model, allograft rejection was previously found to require NK cells and CD8+ T cells (Maiere et al., *Nat Med*, 7:557-562, 2001, herein incorporated by reference in its entirety). Recipient mice were treated twice/week with a neutralizing non-depleting anti-NKG2D mAb (CX5) or control rat IgG starting one day prior to transplantation. Treatment was continued for up to 28 days or until graft rejection. As illustrated in FIG. 23, allograft survival in mice treated with anti-NKG2D mAb was 72.8±22.4 days as compared to 25.4±8.7 days in the control group (P=0.002). As previously shown in other models, anti-NKG2D mAb administration down-modulated NKG2D receptor expression levels on NK cells and CD8+ T cells, but did not result in depletion of NK cells or CD8+ T cells.

In summary, transplantation induces expression of NKG2D ligands and elevated expression of these ligands was sustained in immunocompetent allogeneic recipients. Blockade of the NKG2D receptor prolongs allograft survival in the setting of co-stimulation impaired allograft rejection. Thus a clinical role for NKG2D inhibition in the setting of solid organ transplantation is contemplated.

Solid Organ Grafts.

A role for NKG2D and its ligands in acute and chronic rejection of other types of allografts (e.g., donor tissue mismatched at one or more MHC class I and class II loci as compared to the recipient) is contemplated. Accordingly, the present invention also provides methods for treating or preventing rejection of additional allografts including but not limited to kidney, pancreas, kidney/pancreas, liver, intestine, lung and heart/lung.

Adjunct Therapies.

In some preferred embodiments of the present invention, NKG2D blocking antibodies are used in combination with other immunomodulatory therapies, including but not limited to azathioprine, basiliximab, cyclosporine A, daclizumab, muromondab-CD3, myocophenolic acid, mycophenolate mofetil, prednisone, sirolimus, and tacrolimus. In some embodiments of the present invention, an agent that reduces ligand-induced NKG2D activation is administered to a subject as part of an induction immunosuppression regimen. This approach includes all medications given immediately after transplantation in intensified doses for the purpose of preventing acute rejection. Although the drugs may be continued after discharge for the first 30 days after transplant, they are not used long-term for immunosuppressive maintenance. Associated medications can include methylprednisolone, atgam, thymoglobulin, OKT3, basiliximab or daclixumab. Rapamycin has also been used for induction immunosuppression.

In some embodiments of the present invention, an agent that reduces ligand-induced NKG2D activation is administered to a subject as part of an anti-rejection immunosuppression regimen. This approach includes all immunosuppressive medications given for the purpose of treating an acute rejection episode during the initial post-transplant period or during a specific follow-up period, usually up to 30 days after the diagnosis of acute rejection. Associated medications can include methylprednisolone, atgam, OKT3, thymoglobulin, basiliximabor daclixumab. In further embodiments of the present invention an agent that reduces ligand-induced NKG2D activation is administered to a subject along with one or more of an antibiotic, an anti-fungal medication, an anti-ulcer medication and a diuretic.

All references, including publications, patent applications, and patents, cited herein are hereby incorporated by reference to the same extent as if each reference were individually and specifically indicated to be incorporated by reference and were set forth in its entirety herein (to the maximum extent permitted by law). All headings and sub-headings are used herein for convenience only and should not be construed as limiting the invention in any way. Any combination of the above-described elements in all possible variations thereof is encompassed by the invention unless otherwise indicated herein or otherwise clearly contradicted by context.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents. A description herein of an aspect or embodiment of the invention using terms such as "comprising", "having," "including," or "containing" a particular element is intended to provide support for an aspect or embodiment of the invention that "consists of", "consists essentially of", or "substantially comprises" that particular element, unless otherwise stated or clearly contradicted by context. This invention includes all modifications and equivalents of the subject matter recited in the claims appended hereto as permitted by applicable law.

The invention claimed is:

1. A method for prolonging survival of a hematopoietic graft, the method comprising:
   administering an agent that reduces ligand-induced NKG2D activation of cells to a mammalian subject in need thereof, under conditions suitable for prolonging survival of a hematopoietic graft,
   wherein the agent is an antibody that binds NKG2D or an NKG2D-binding fragment thereof.

2. The method of claim 1, wherein the administering is done prior to transplantation of the graft.

3. The method of claim 1, wherein the cells are selected from the group consisting of NKG2D+ CD8+ T cells, NKG2D+ CD4+ T cells, NKG2D+γδ T cells, NKG2D+ NK cells, and macrophages.

4. The method of claim 1, wherein the antibody reduces the interaction of NKG2D with DAP10.

5. The method of claim 1, wherein the antibody reduces the amount of NKG2D on the surface of the cells.

6. The method of claim 1, wherein the antibody increases the rate at which cell-surface NKG2D is internalized.

7. The method of claim 1, wherein the antibody is a monoclonal antibody.

8. The method of claim 7, wherein the monoclonal antibody is a human antibody, a humanized antibody, or a chimeric antibody.

9. The method of claim 1, further comprising administering an adjunct therapy to the subject.

10. The method of claim 9, wherein the adjunct therapy comprises at least one hematopoietic growth factor.

11. The method of claim 10, wherein the hematopoietic growth factor is selected from the group consisting of erythropoietin, granulocyte-colony stimulating factor (G-CSF), granulocyte macrophage-colony stimulating factor (GM-CSF), interleukin-13 (IL-3), interleukin (IL-11), thrombopoietin, and combinations thereof.

12. The method of claim 9, wherein the adjunct therapy comprises one or more of an antibiotic, an anti-viral and an anti-fungal medication.

13. The method of claim 1, wherein the hematopoietic graft is a bone marrow graft or a peripheral blood stem cell (PBSM) graft.

14. The method of claim 1, wherein the hematopoietic graft is a bone marrow graft.

15. The method of claim 1, wherein the hematopoietic graft is an allograft.

16. The method of claim 1, wherein the antibody or fragment thereof binds to an extracellular epitope of NKG2D with a Kd of less than 11 mM.

17. The method of claim 1, wherein the administering is done prior to and after transplantation of the graft.

* * * * *

SEQUENCE LISTING

```
<160> NUMBER OF SEQ ID NOS: 17

<210> SEQ ID NO 1
<211> LENGTH: 699
<212> TYPE: DNA
<213> ORGANISM: Mus musculus

<400> SEQUENCE: 1
atggcattga ttcgtgatcg aaagtctcat cactcagaga tgagcaaatg ccataattac      60
gacctcaagc cagcaaagtg ggatacttct caagaacaac agaaacaaag attagcacta     120
actaccagtc aacctggaga aaatggtatc ataagaggaa gatacctat agaaaaactc      180 aaaatatctc caatgttcgt tgttcgagtc cttgctatag ccttggcaat tcgattcacc     240
cttaacacat tgatgtggct tgccattttc aaagagacgt ttcagccagt attgtgcaac     300
aaggaagtcc cagtttcctc aagagagggc tactgtggcc catgccctaa caactggata     360
tgtcacagaa acaactgtta ccaattttt aatgaagaga aacctggaa ccagagccaa      420 gcttcctgtt tgtctcaaaa ttccagcctt ctgaagatat acagtaaaga agaacaggat     480
ttcttaaagc tggttaagtc ctatcactgg atgggactgg tccagatccc agcaaatggc     540
tcctggcagt gggaagatgg ctcctctctc tcatacaatc agttaactct ggtggaaata     600
ccaaaaggat cctgtgctgt ctatggctca agctttaagg cttacacaga agactgtgca     660
aatctaaaca cgtacatctg catgaaaagg gcggtgtaa                             699

<210> SEQ ID NO 2
<211> LENGTH: 232
<212> TYPE: PRT
<213> ORGANISM: Mus musculus
```

<400> SEQUENCE: 2

```
Met Ala Leu Ile Arg Asp Arg Lys Ser His His Ser Glu Met Ser Lys
1               5                   10                  15

Cys His Asn Tyr Asp Leu Lys Pro Ala Lys Trp Asp Thr Ser Gln Glu
            20                  25                  30

Gln Gln Lys Gln Arg Leu Ala Leu Thr Thr Ser Gln Pro Gly Glu Asn
        35                  40                  45

Gly Ile Ile Arg Gly Arg Tyr Pro Ile Glu Lys Leu Lys Ile Ser Pro
    50                  55                  60

Met Phe Val Val Arg Val Leu Ala Ile Ala Leu Ala Ile Arg Phe Thr
65                  70                  75                  80

Leu Asn Thr Leu Met Trp Leu Ala Ile Phe Lys Glu Thr Phe Gln Pro
                85                  90                  95

Val Leu Cys Asn Lys Glu Val Pro Val Ser Ser Arg Glu Gly Tyr Cys
            100                 105                 110

Gly Pro Cys Pro Asn Asn Trp Ile Cys His Arg Asn Asn Cys Tyr Gln
        115                 120                 125

Phe Phe Asn Glu Glu Lys Thr Trp Asn Gln Ser Gln Ala Ser Cys Leu
    130                 135                 140

Ser Gln Asn Ser Ser Leu Leu Lys Ile Tyr Ser Lys Glu Glu Gln Asp
145                 150                 155                 160

Phe Leu Lys Leu Val Lys Ser Tyr His Trp Met Gly Leu Val Gln Ile
                165                 170                 175

Pro Ala Asn Gly Ser Trp Gln Trp Glu Asp Gly Ser Ser Leu Ser Tyr
            180                 185                 190

Asn Gln Leu Thr Leu Val Glu Ile Pro Lys Gly Ser Cys Ala Val Tyr
        195                 200                 205

Gly Ser Ser Phe Lys Ala Tyr Thr Glu Asp Cys Ala Asn Leu Asn Thr
    210                 215                 220

Tyr Ile Cys Met Lys Arg Ala Val
225                 230
```

<210> SEQ ID NO 3
<211> LENGTH: 651
<212> TYPE: DNA
<213> ORGANISM: Homo sapiens

<400> SEQUENCE: 3

```
atggggtgga ttcgtggtcg gaggtctcga cacagctggg agatgagtga atttcataat     60
tataacttgg atctgaagaa gagtgatttt tcaacacgat ggcaaaagca agatgtcca    120
gtagtcaaaa gcaaatgtag agaaaatgca tctccatttt ttttctgctg cttcatcgct    180
gtagccatgg gaatccgttt cattattatg gtagcaatat ggagtgctgt attcctaaac    240
tcattattca accaagaagt tcaaattccc ttgaccgaaa gttactgtgg cccatgtcct    300
aaaaactgga tatgttacaa aaataactgc taccaatttt ttgatgagag taaaaactgg    360
tatgagagcc aggcttcttg tatgtctcaa aatgccagcc ttctgaaagt atacagcaaa    420
gaggaccagg atttacttaa actggtgaag tcatatcatt ggatgggact agtacacatt    480
ccaacaaatg gatcttggca gtgggaagat ggctccattc tctcacccaa cctactaaca    540
ataattgaaa tgcagaaggg agactgtgca ctctatgcct cgagctttaa aggctatata    600
gaaaactgtt caactccaaa tacatacatc tgcatgcaaa ggactgtgta a             651
```

```
<210> SEQ ID NO 4
<211> LENGTH: 216
<212> TYPE: PRT
<213> ORGANISM: Homo sapiens

<400> SEQUENCE: 4
```

Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
            20                  25                  30

Arg Trp Gln Lys Gln Arg Cys Pro Val Val Lys Ser Lys Cys Arg Glu
        35                  40                  45

Asn Ala Ser Pro Phe Phe Phe Cys Cys Phe Ile Ala Val Ala Met Gly
    50                  55                  60

Ile Arg Phe Ile Ile Met Val Ala Ile Trp Ser Ala Val Phe Leu Asn
65                  70                  75                  80

Ser Leu Phe Asn Gln Glu Val Gln Ile Pro Leu Thr Glu Ser Tyr Cys
                85                  90                  95

Gly Pro Cys Pro Lys Asn Trp Ile Cys Tyr Lys Asn Asn Cys Tyr Gln
            100                 105                 110

Phe Phe Asp Glu Ser Lys Asn Trp Tyr Glu Ser Gln Ala Ser Cys Met
        115                 120                 125

Ser Gln Asn Ala Ser Leu Leu Lys Val Tyr Ser Lys Glu Asp Gln Asp
    130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
                165                 170                 175

Asn Leu Leu Thr Ile Ile Glu Met Gln Lys Gly Asp Cys Ala Leu Tyr
            180                 185                 190

Ala Ser Ser Phe Lys Gly Tyr Ile Glu Asn Cys Ser Thr Pro Asn Thr
        195                 200                 205

Tyr Ile Cys Met Gln Arg Thr Val
    210                 215

```
<210> SEQ ID NO 5
<211> LENGTH: 9
<212> TYPE: PRT
<213> ORGANISM: Artificial Sequence
<220> FEATURE:
<223> OTHER INFORMATION: Synthetic Construct

<400> SEQUENCE: 5
```

Lys Tyr Asn Lys Ala Asn Val Phe Leu
1               5

```
<210> SEQ ID NO 6
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
```
ctagtgccac ctgggaattc a                                            21

```
<210> SEQ ID NO 7
<211> LENGTH: 24
<212> TYPE: DNA
<213> ORGANISM: Artificial Sequence
```

```
<220> FEATURE:
<223> OTHER INFORMATION: Synthetic Construct

<400> SEQUENCE: 7
catcattagc tgatctccag ctca                                            24

<210> SEQ ID NO 8
<211> LENGTH: 38
<212> TYPE: DNA
<213> ORGANISM: Artificial Sequence
<220> FEATURE:
<223> OTHER INFORMATION: Synthetic Construct

<400> SEQUENCE: 8
catcagtgac agttacttct tcaccttcta cacagaga                             38

<210> SEQ ID NO 9
<211> LENGTH: 4
<212> TYPE: PRT
<213> ORGANISM: Artificial Sequence
<220> FEATURE:
<223> OTHER INFORMATION: Synthetic Construct

<400> SEQUENCE: 9

Tyr Ile Asn Met
1

<210> SEQ ID NO 10
<211> LENGTH: 22
<212> TYPE: DNA
<213> ORGANISM: Artificial Sequence
<220> FEATURE:
<223> OTHER INFORMATION: Synthetic Construct

<400> SEQUENCE: 10
ggatgggact agtacacatt cc                                              22

<210> SEQ ID NO 11
<211> LENGTH: 21
<212> TYPE: DNA
<213> ORGANISM: Artificial Sequence
<220> FEATURE:
<223> OTHER INFORMATION: Synthetic Construct

<400> SEQUENCE: 11
tggcagtggg aagatggctc c                                               21

<210> SEQ ID NO 12
<211> LENGTH: 29
<212> TYPE: DNA
<213> ORGANISM: Artificial Sequence
<220> FEATURE:
<223> OTHER INFORMATION: Synthetic Construct

<400> SEQUENCE: 12
cagaagggag actgtgcact ctatgcctc                                       29

<210> SEQ ID NO 13
<211> LENGTH: 22
<212> TYPE: DNA
<213> ORGANISM: Artificial Sequence
<220> FEATURE:
<223> OTHER INFORMATION: Synthetic Construct

<400> SEQUENCE: 13
ggatgggatt agtatagatt cc                                              22
```

```
<210> SEQ ID NO 14
<211> LENGTH: 34
<212> TYPE: DNA
<213> ORGANISM: Artificial Sequence
<220> FEATURE:
<223> OTHER INFORMATION: Synthetic Construct

<400> SEQUENCE: 14
catcagtgac agttacttct tcaccttcta caca                              34

<210> SEQ ID NO 15
<211> LENGTH: 33
<212> TYPE: DNA
<213> ORGANISM: Artificial Sequence
<220> FEATURE:
<223> OTHER INFORMATION: Synthetic Construct

<400> SEQUENCE: 15
caaactttgc tttccctggt taagcagtac agc                               33

<210> SEQ ID NO 16
<211> LENGTH: 23
<212> TYPE: DNA
<213> ORGANISM: Artificial Sequence
<220> FEATURE:
<223> OTHER INFORMATION: Synthetic Construct

<400> SEQUENCE: 16
agcttgcaac cttaaccatt ttg                                          23

<210> SEQ ID NO 17
<211> LENGTH: 25
<212> TYPE: DNA
<213> ORGANISM: Artificial Sequence
<220> FEATURE:
<223> OTHER INFORMATION: Synthetic Construct

<400> SEQUENCE: 17
tggaaagaat gtcttgattg ttgaa                                        25
```